US012458639B2

(12) United States Patent
Huang et al.

(10) Patent No.: US 12,458,639 B2
(45) Date of Patent: Nov. 4, 2025

(54) TUBULIN BINDING COMPOUNDS AND THERAPEUTIC USE THEREOF

(71) Applicant: BeyondSpring Pharmaceuticals, Inc., New York, NY (US)

(72) Inventors: Lan Huang, New York, NY (US); Santosh Ambadas Khedkar, Lexington, MA (US); Michel O. Steinmetz, Villigen (CH)

(73) Assignee: BeyondSpring Pharmaceuticals, Inc., New York, NY (US)

(*) Notice: Subject to any disclaimer, the term of this patent is extended or adjusted under 35 U.S.C. 154(b) by 0 days.

(21) Appl. No.: 18/306,191

(22) Filed: Apr. 24, 2023

(65) Prior Publication Data

US 2024/0082243 A1 Mar. 14, 2024

Related U.S. Application Data

(62) Division of application No. 16/476,242, filed as application No. PCT/US2018/012668 on Jan. 5, 2018, now Pat. No. 11,633,393.

(60) Provisional application No. 62/443,247, filed on Jan. 6, 2017.

(51) Int. Cl.

| | |
|---|---|
| ***C07D 403/06*** | (2006.01) |
| ***A61K 31/495*** | (2006.01) |
| ***A61K 31/496*** | (2006.01) |
| ***A61P 35/00*** | (2006.01) |
| ***C07D 411/06*** | (2006.01) |

(52) U.S. Cl.
CPC .......... *A61K 31/496* (2013.01); *A61K 31/495* (2013.01)

(58) Field of Classification Search
CPC .. C07D 403/06; C07D 411/06; A61K 31/496; A61P 35/00
See application file for complete search history.

(56) References Cited

U.S. PATENT DOCUMENTS

| | | | |
|---|---|---|---|
| 4,410,537 | A | 10/1983 | Kneen |
| 4,535,183 | A | 8/1985 | Kneen |
| 5,607,934 | A | 3/1997 | Tone et al. |
| 5,733,888 | A | 3/1998 | Bryans et al. |
| 5,852,018 | A | 12/1998 | Bryans et al. |
| 5,872,151 | A | 2/1999 | Rhodes |
| 5,874,443 | A | 2/1999 | Kiely et al. |
| 5,886,210 | A | 3/1999 | Rayle et al. |
| 5,891,877 | A | 4/1999 | Brocchini et al. |
| 5,922,683 | A | 7/1999 | Or et al. |
| 5,939,098 | A | 8/1999 | Reidenberg et al. |
| 5,958,980 | A | 9/1999 | Rhodes |
| 6,069,146 | A | 5/2000 | Fenical et al. |
| 6,096,786 | A | 8/2000 | Rhodes |
| 6,350,759 | B1 | 2/2002 | Casara et al. |
| 6,358,957 | B1 | 3/2002 | Fukumoto et al. |
| 6,500,825 | B2 | 12/2002 | Lan et al. |
| 6,506,787 | B2 | 1/2003 | Fujishita et al. |
| 6,509,331 | B1 | 1/2003 | Audia et al. |
| 6,583,143 | B2 | 6/2003 | Haddach |
| 6,713,480 | B2 | 3/2004 | Fukumoto et al. |
| 6,808,710 | B1 | 10/2004 | Wood et al. |
| 6,972,289 | B1 | 12/2005 | Kanzaki et al. |
| 7,026,322 | B2 | 4/2006 | Hayashi et al. |
| 7,064,201 | B2 | 6/2006 | Hayashi et al. |
| 7,488,802 | B2 | 2/2009 | Collins et al. |
| 7,629,380 | B2 | 12/2009 | McMorris et al. |
| 7,635,757 | B2 | 12/2009 | Freeman et al. |
| 7,674,903 | B2 | 3/2010 | Hayashi et al. |
| 7,700,615 | B2 | 4/2010 | Edwards et al. |
| 7,919,497 | B2 | 4/2011 | Palladino et al. |
| 7,935,704 | B2 | 5/2011 | Palladino et al. |
| 7,943,743 | B2 | 5/2011 | Korman et al. |
| 7,956,058 | B2 | 6/2011 | Hayashi et al. |
| 8,008,449 | B2 | 8/2011 | Korman et al. |
| 8,129,527 | B2 | 3/2012 | Palladino et al. |
| 8,168,757 | B2 | 5/2012 | Finnefrock et al. |
| 8,217,149 | B2 | 7/2012 | Irving et al. |
| 8,247,552 | B2 | 8/2012 | Palladino et al. |
| 8,618,292 | B2 | 12/2013 | Palladino et al. |
| 9,358,289 | B2 | 6/2016 | Korman et al. |
| 9,394,368 | B2 | 7/2016 | Brogdon et al. |
| 10,076,518 | B2 | 9/2018 | Huang |
| 10,155,748 | B2 | 12/2018 | Huang et al. |
| 10,238,630 | B2 | 3/2019 | Cox et al. |
| 10,238,650 | B2 | 3/2019 | Huang |
| 10,357,491 | B2 | 7/2019 | Huang |
| 10,550,104 | B2 | 2/2020 | Huang et al. |
| 10,569,169 | B2 | 2/2020 | Li et al. |

(Continued)

FOREIGN PATENT DOCUMENTS

| | | |
|---|---|---|
| CN | 110240592 | 9/2017 |
| EA | 010198 B1 | 6/2008 |

(Continued)

OTHER PUBLICATIONS

"Definition of 'within'". [Online] [2015 Archived version accessed on Aug. 13, 2020 from |https://web.archive.org/web/20151030162428/https://dictionary.cambridge.org/us/dictionary/english/within. Cambridge English Dictionary. (Year: 2015).

Abels, Christoph, Targeting of the Vascular System of Solid Tumours by Photodynamic Therapy (PDT), Photochem Photobiol Sci., (Mar. 2004) 3: 765-771.

Abolhasani et al., Jan. 2015, In-silico investigation of tubulin binding modes of a series of novel antiproliferative spiroisoxazoline compounds using docking studies, Iranian Journal of Pharmaceutical Research, 14(1):141-147.

Abstracts of The 1999 Joint Chubu and Kansai Branch Conference and Symposia of Japan Society for Bioscience, Biotechnology, and Agrochemistry, (1999) p. 48.

Acquaviva et al., "Targeting KRAS-Mutant Non-Small Cell Lung Cancer with the Hsp90 Inhibitor Ganetespib", Mol Cancer Ther, Dec. 2012, 11(12), pp. 2633-2643.

(Continued)

*Primary Examiner* — Bruck Kifle

(74) *Attorney, Agent, or Firm* — Knobbe Martens Olson & Bear LLP

(57) ABSTRACT

Disclosed herein are compounds that can bind to tubulin and activate GEF-H1. Methods of using these compounds for treating cancer are also disclosed.

2 Claims, 3 Drawing Sheets

(56) References Cited

U.S. PATENT DOCUMENTS

| | | | |
|---|---|---|---|
| 10,596,169 | B2 | 3/2020 | Huang |
| 10,668,063 | B2 | 6/2020 | Huang |
| 10,912,748 | B2 | 2/2021 | Mohanlal |
| 11,045,467 | B2 | 6/2021 | Huang |
| 11,229,642 | B2 | 1/2022 | Huang et al. |
| 11,254,657 | B2 | 2/2022 | Huang |
| 11,400,086 | B2 | 8/2022 | Mohanlal et al. |
| 11,633,393 | B2 | 4/2023 | Huang |
| 11,786,523 | B2 | 10/2023 | Huang |
| 11,857,522 | B2 | 1/2024 | Mohanlal et al. |
| 11,918,574 | B2 | 3/2024 | Huang |
| 12,024,501 | B2 | 7/2024 | Huang et al. |
| 2002/0028819 | A1 | 3/2002 | Teng et al. |
| 2002/0143021 | A1 | 10/2002 | Fukumoto et al. |
| 2004/0102454 | A1 | 5/2004 | Hayashi et al. |
| 2004/0176372 | A1 | 9/2004 | Suto et al. |
| 2006/0079534 | A1 | 4/2006 | Kanzaki et al. |
| 2006/0167010 | A1 | 7/2006 | Hayashi et al. |
| 2006/0223822 | A1 | 10/2006 | Hayashi et al. |
| 2007/0293453 | A1 | 12/2007 | Fisher et al. |
| 2008/0199485 | A1 | 8/2008 | Kundig et al. |
| 2008/0255035 | A1 | 10/2008 | Trieu et al. |
| 2009/0170837 | A1 | 7/2009 | Gourdeau et al. |
| 2009/0317368 | A1 | 12/2009 | Chen |
| 2012/0041070 | A1 | 2/2012 | Shengfan et al. |
| 2012/0277251 | A1 | 11/2012 | Palladino et al. |
| 2013/0131018 | A1 | 5/2013 | Leblond et al. |
| 2013/0303481 | A1 | 11/2013 | Marcus |
| 2014/0322275 | A1 | 10/2014 | Brogdon et al. |
| 2014/0363514 | A1 | 12/2014 | Koyakutty et al. |
| 2015/0202291 | A1 | 7/2015 | Bosch et al. |
| 2015/0291549 | A1 | 10/2015 | Chupak et al. |
| 2016/0243153 | A1 | 8/2016 | Sundaram et al. |
| 2017/0226221 | A1 | 8/2017 | Madiyalakan et al. |
| 2018/0028531 | A1 | 2/2018 | Huang et al. |
| 2018/0140600 | A1 | 5/2018 | Li et al. |
| 2019/0209549 | A1 | 7/2019 | Arline et al. |
| 2020/0129504 | A1 | 4/2020 | Mohanlal et al. |
| 2020/0281921 | A1 | 9/2020 | Huang |
| 2021/0030843 | A1 | 2/2021 | Mohanlal |
| 2021/0052583 | A1 | 2/2021 | Hogberg et al. |
| 2021/0161888 | A1 | 6/2021 | Huang et al. |
| 2021/0177952 | A1 | 6/2021 | Mohanlal et al. |
| 2022/0378784 | A1 | 12/2022 | Mohanlal et al. |
| 2022/0387365 | A1 | 12/2022 | He |
| 2023/0035763 | A1 | 2/2023 | Tonra |
| 2023/0181605 | A1 | 6/2023 | Mohanlal et al. |
| 2024/0197723 | A1 | 6/2024 | Huang |

FOREIGN PATENT DOCUMENTS

| | | | |
|---|---|---|---|
| EA | 016817 | B1 | 7/2012 |
| EP | 0 054 924 | | 6/1982 |
| EP | 0 655 060 | | 1/1998 |
| GB | 2143823 | | 2/1985 |
| JP | 05-9164 | | 1/1993 |
| JP | 05-255106 | | 10/1993 |
| JP | 10-130266 | | 5/1998 |
| JP | 2002-507612 | A | 3/2002 |
| JP | 2012-144512 | | 8/2012 |
| JP | 2013-501791 | | 1/2013 |
| JP | 2014-508167 | | 4/2014 |
| JP | 2015-030679 | | 2/2015 |
| JP | 2016-516523 | | 6/2016 |
| JP | 2016-518879 | | 6/2016 |
| JP | 2018-036233 | | 3/2018 |
| RU | 2258702 | | 8/2005 |
| RU | 2011 148 945 | A | 4/2010 |
| WO | WO 87/05297 | | 9/1987 |
| WO | WO 94/07479 | | 4/1994 |
| WO | WO 95/06077 | | 3/1995 |
| WO | WO 95/21832 | | 8/1995 |
| WO | WO 96/20190 | | 7/1996 |
| WO | WO 99/38844 | | 8/1999 |
| WO | WO 99/048889 | | 9/1999 |
| WO | WO 00/012121 | | 3/2000 |
| WO | WO 01/053290 | | 7/2001 |
| WO | WO 01/070663 | | 9/2001 |
| WO | WO 03/074550 | | 9/2003 |
| WO | WO 03/097164 | | 11/2003 |
| WO | WO 04/016600 | | 2/2004 |
| WO | WO 04/054498 | | 7/2004 |
| WO | WO 04/093831 | | 11/2004 |
| WO | WO 05/077940 | | 8/2005 |
| WO | WO 06/121168 | | 11/2006 |
| WO | WO 07/035841 | | 3/2007 |
| WO | WO 07/113648 | | 10/2007 |
| WO | WO 08/128169 | | 10/2008 |
| WO | WO 09/064444 | | 5/2009 |
| WO | WO 09/089260 | | 7/2009 |
| WO | WO 10/001169 | | 1/2010 |
| WO | WO 10/083439 | | 7/2010 |
| WO | WO 10/101627 | | 9/2010 |
| WO | WO 11/034954 | | 3/2011 |
| WO | WO 11/050344 | | 5/2011 |
| WO | WO 11/066389 | | 6/2011 |
| WO | WO 11/079507 | | 7/2011 |
| WO | WO 11/109625 | | 9/2011 |
| WO | WO 11/146382 | | 11/2011 |
| WO | WO 11/151423 | | 12/2011 |
| WO | WO 12/014549 | | 2/2012 |
| WO | WO 12/035436 | | 3/2012 |
| WO | WO 12/074904 | | 6/2012 |
| WO | WO 12/145493 | | 10/2012 |
| WO | WO 13/078537 | | 6/2013 |
| WO | WO 13/090552 | | 6/2013 |
| WO | WO 13/177633 | | 12/2013 |
| WO | WO 14/036412 | | 3/2014 |
| WO | WO 14/066834 | | 5/2014 |
| WO | WO 14/130657 | | 8/2014 |
| WO | WO 14/160183 | | 10/2014 |
| WO | WO 14/183066 | | 11/2014 |
| WO | WO 14/195852 | | 12/2014 |
| WO | WO 15/069770 | | 5/2015 |
| WO | WO 15/069790 | | 5/2015 |
| WO | WO 15/160641 | | 10/2015 |
| WO | WO 16/081281 | | 5/2016 |
| WO | WO 16/165007 | | 10/2016 |
| WO | WO 17/062505 | | 4/2017 |
| WO | WO 19/194738 | | 10/2019 |
| WO | WO 21/225908 | | 11/2021 |

OTHER PUBLICATIONS

Agarwal et al., "OP449, a Novel SET Antagonist, Is Cytotoxic To Leukemia Cells and Enhances Efficacy of Tyrosine Kinase Inhibitors in Drug-Resistant Myeloid Leukemias," pursuant to an EMBASE record for a Conference Abstract: 603. Oncogenes and Tumor Suppressors: Poster II (Nov. 15, 2013) Blood (2013) 122(21): 2511.

Aggarwal et al., Antiangiogenic agents in the management of non-small cell lung cancer: Where do we stand now and where are we headed? Cancer Biology & Therapy (2012), 13(5), 247-263.

Ahmed et al. "A new rapid and simple non-radioactive assay to monitor and determine the proliferation of lymphocytes: an alternative to [$^3$ H]thymidine incorporation assay." J. Immunol. Methods. 170, 211-224 (1994).

Akerlund et al., "Diketopiperazine-Based Polymers from Common Amino Acids," Journal of Applied Polymer Science, (2000) 78 (12), 2213-2218.

Algaier et al. "The effects of dimethyl sulfoxide on the kinetics of tubulin assembly." Biochim. Biophys. Acta. 954, 235-43 (1988).

Ali et al. "Toxicity of echinulin from Aspergillus chevalieri in rabbits." Toxicology Letters. (1989) 48: 235-41.

Asahina, T., "Spectrochemical Study of Amino-acid Anhydrides," Bulletin of the Chemical Society of Japan, (1930) 5, 354-365.

Augustin, M. "Die Umsetzung des 2,5-Diketopiperazins mit Aldehyden und Nitrosoverbindungen" Journal für Praktische Chemie, (1966) 32(4), 158-166.

Aviel-Ronen et al., "K-ras Mutations in Non-Small-Cell Lung Carcinoma: A Review," *Clinical Lung Cancer* (Jul. 2006) vol. 8, No. 1, pp. 30-38.

(56) References Cited

OTHER PUBLICATIONS

Bankowska et al., Derivatives of 1,2,3-triazole. Potential drugs?, Wiadomosci Chemiczne (2012), 66(11-12), 993-1022.
Beavis et al., "Dual PD-1 and CTLA-4 Checkpoint Blockade Promotes Antitumor Immune Responses through CD4$^+$Foxp$^3$-Cell-Mediated Modulation of CD103+ Dendritic Cells," Cancer Immunol Res (Sep. 2018) 6(9):1069-1081.
Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11: 1411-1415.
Bertelsen et al., "Vascular effects of plinabulin (NPI-2358) and the influence on tumour response when given alone or combined with radiation," International Journal of Radiation Biology (2011), 87(11), 1126-1134.
Bertino J., et al., "Principles of Cancer Therapy." Cecil Textbook of Medicine. Eds. Lee Goldman, et al. 21nd ed., (2000), Chapter 198, pp. 1060-1074.
Blayney et al., "Plinabulin, a Novel Small Molecule That Ameliorates Chemotherapy-Induced Neutropenia, Is Administered on the Same Day of Chemotherapy and Has Anticancer Efficacy", Meeting Info.: 58th Annual Meeting and Exposition of the American Society-of-Hematology (ASH), Blood (2016) 128(22): 2508.
Bond et al. "The Synthesis of Viridamine, a Penicillium Viridicatum Mycotoxin." Synthetic Commun. 19 (13&14), 2551-2566 (1989).
Borisy, G.G. "A Rapid Method for Quantitative Determination of Microtubule Protein using DEAE-Cellulose Filters." Anal. Biochem. 50, 373-385 (1972).
Braga et al. "Crystal Polymorphism and Multiple Crystal Forms," Struct Bond (2009) 132:25-50.
Brahmer et al., "Safety and Activity of Anti-PD-L1 Antibody in Patients with Advanced Cancer," N Engl J Med (2012) 366:2455-2465.
Buchbinder et al., Feb. 2016, CTLA-4 and PD-1 pathways: similarities, differences, and implications of their inhibition, American Journal of Clinical Oncology, 39(1):98-106.
Burtles, Sally, "Transition from Preclinical to first-in-man Phase", Expert Scientific Group on Phase One Clinical Trials Final Report, Presentation Jun. 19, 2006, pp. 35-38.
Cai, Small molecule vascular disrupting agents: potential new drugs for cancer treatment, a 2009 update, Frontiers in Anti-Cancer Drug Discovery (2010), 1, 380-427.
Cai, Sui X., "Small Molecule Vascular Disrupting Agents: Potential New Drugs for Cancer Treatment", Recent Pat Anticancer Drug Discov. (2007) 2(1): 79-101.
Caira, 1998, Crystalline polymorphism of organic compounds, Topics in Current Chemistry, 198:163-208.
Callahan et al., "At the Bedside: CTLA-4- and PD-1-blocking antibodies in cancer immunotherapy", J Leukocyte Biol, vol. 94, Jul. 2013, pp. 41-53.
Carter et al., "No patient left behind: The promise of immune priming with epigenetic agents," Oncoimmunology (2017) vol. 6, No. 10, e1315486 (13 pages).
Chaplin et al., "Antivascular approaches to solid tumour therapy: evaluation of tubulin binding agents", Br. J. Cancer 1996, 74 (Suppl. XXVII), S86-S88.
Chen et al., "Adjuvant effect of docetaxel on the immune responses to influenza A H1N1 vaccine in mice," BMC Immunology (2012) 13:36, pp. 1-12.
Chin et al., "Immune Intervention with Monoclonal Antibodies Targeting CD152 (CTLA-4) for Autoimmune and Malignant Diseases," Chang Gung Med J (Jan.-Feb. 2008) vol. 31, No. 1, pp. 1-15.
ClinicalTrials.gov Identifier NCT00892931, "Phase 2 study MPC-6827 for recurrent glioblastoma multiforme," (Oct. 14, 2011). [retrieved from internet on Jul. 30, 2019] <URL: https://clinicaltrials.gov/ct2/show/NCT00892931> 7 pages.
ClinicalTrials.gov Identifier NCT02846792, "Nivolumab and Plinabulin in Treating Patients With Stage IIIB-IV, Recurrent, or Metastatic Non-small Cell Lung Cancer," (Jul. 27, 2016). [retrieved from internet on Sep. 17, 2019], <URL: https://clinicaltrials.gov/ct2/show/NCT02846792?term=plinabuilin&rank=1> 11 pages.
ClinicalTrials.gov Identifier NCT03294577, "Plinabulin vs. pegfilgrastim in prevention of TAC induced neutropenia" (Sep. 27, 2107). <URL:ttps://clinicaltrials.gov/ct2/show/NCT3294577> 4 pp.
Cole, P., "Durvalumab, Human anti-PD-L1 monoclonal antibody Immune checkpoint inhibitor Oncolytic", Drugs of the Future 2014, 39(12): pp. 843-847.
Collins et al., 2014, Lipid tucaresol as an adjuvant for methamphetamine vaccine development, CHemComm, 50:4079-4081.
Cooper et al., "Response to BRAF Inhibition in Melanoma Is Enhanced When Combined with Immune Checkpoint Blockade," Published OnlineFirst Apr. 29, 2014; DOI: 10.1158/2326-6066.CIR-13-0215; Cancer Immunol Res (Jul. 2014) 2(7) 643-654.
Costa et al., "Analyses of selected safety endpoints in phase 1 and late-phase clinical trials of anti-PD-1 and PD-L1 inhibitors: prediction of immune-related toxicities," Oncotarget (2017) vol. 8, No. 40, pp. 67782-67789.
Crawford, Aug. 2003, Once-per-cycle pegilgrastim (neulata) for the management of chemotherapy-induced neutropenia, Seminars in Oncology 30(4)Suppl 13:23-30.
Cui et al. "Novel Mammalian Cell Cycle Inhibitors, Tryprostatins A, B and Other Diketopiperazines Produced by Aspergillus fumigatus." J. Antibiotics. 49(6), 534-40 (1996).
Cui et al. "Novel Mammalian Cell Cycle Inhibitors, Tryprostatins A, B and Other Diketopiperazines Produced by Aspergillus fumigatus." J. Antibiotics. 49(6): 527-33 (1996).
Dale, Oct. 2015, Neutropenia, John Wiley & Sons Ltd., www.els.net, 8 pp.
Dalgleish, 2015, Rationale for combining immunotherapy with chemotherapy, Immunotherapy, 7(3):309-316.
Das et al., Feb. 1, 2015, Combination therapy with anti-CLTA4 and antiPD1 leads to distinct immunologic changes in-vivo, J. Immunolog, 194(3):950-959.
Davis et al., ZD6126: A Novel Vascular-targeting Agent That Causes Selective Destruction of Tumor Vasculature, Cancer Research (Dec. 15, 2002) 62: 7247-7253.
Dorwald, F., "Side Reactions in Organic Synthesis" Wiley-VCH Verlag Gmbh & Co. KgaA, Weinheim, (2005), book cover and preface p. IX only.
Drug Approval And Licensing Procedures in Japan 2001, 2001, pp. 243-244.
Dunitz et al., "Disappearing Polymorphs," Acc. Chem. Res. (1995) vol. 28, No. 4, pp. 193-200.
Fernandez-Medarde et al., Mar. 2011, Ras in cancer and developmental diseases, Genes & Cancer, 2(3):344-358.
Fernandez-Tejada et al., 2014, Design, synthesis, and immunologic evaluation of vaccine adjuvant conjugates based on QS-21 and tucaresol, Bioorganic & Medicinal Chemistry, 22:5917-5923.
Fernandez-Tejada et al., 2016, Development of improved vaccine adjuvants based on the saponin natural product QS-21 through chemical synthesis, Accounts of Chemical Research 49:1741-1756.
Ferrer et al., Plinabulin: tubulin polymerization inhibitor vascular-disrupting agent oncolytic, Drugs of the Future (2010), 35(1), 11-15.
Fessas et al., 2017, A molecular and preclinical comparsion of the PC-1-targeted t-cell checkpoint inhibitors nivolumab and mebrolizumag, Seminars in Oncology, 44:136-140.
Field et al., 2014, Microtubule-targeting agents are clinically successful due to both mitotic and interphase impairment of microtubule function, Bioorganic & Medicinal Chemistry, 22:5050-5059.
Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.
Folkman, Dec. 2002, Role of angiogenesis in tumor growth and metastasis, Semin Oncol, 29:15-18.
Frost et al., Novel Syngeneic Pseudo-orthotopic Prostate Cancer Model: Vascular, Mitotic and Apoptotic Responses to Castration, Microvasc Research (Dec. 2004) 69: 1-9.
Fukushima et al., "Biological Activities of Albonoursin," J. Antibiotics, (1973) 26:175.
Gallina et al., "Condensation of 1,4-diacetylpiperazine-2,5-dione with aldehydes", Tetrahedron 1974, 30, 667-673.
Gameiro et al., "Exploitation of differential homeostatic proliferation of T-cell subsets following chemotherapy to enhance the

(56) References Cited

OTHER PUBLICATIONS efficacy of vaccine-mediated antitumor responses," Cancer Immunology Immunotherapy (2011) vol. 60, No. 9, pp. 1227-1242.
Garris et al., "Successful Anti-PD-1 Cancer Immunotherapy Requires T Cell-Dendritic Cell Crosstalk Involving the Cytokines IFN-( and IL-12," Immunity (Dec. 18, 2018) 49, pp. 1-14, e1-e7 (22 pages).
Goldani et al. "Treatment of murine pulmonary mucormycosis with SCH 42427, a broad-spectrum triazole antifungal drug", Correspondence, J Antimicrob Chemother. 33, 369-372 (1994).
Goldfarb et al., "Synthesis of β-2-thienylalanine," Izvestiya Akademii Nauk SSSR, Seriya Khimicheskaya, (1958) 98-100, as abstracted by Caplus.
Gordon et al. "Reductive Alkylation on a Solid Phase: Synthesis of a Piperazinedione Combinatorial Library." J. Bioorg. Med. Chem. Letters. 5, 47-50 (1995).
Granville et al., Release of Cytochrome c1 Bax Migration, Bid Cleavage, and Activation of Caspases 2, 3, 6, 7, 8, and 9 during Endothelial Cell Apoptosis, Am J Path., (Oct. 1999) 155(4): 1021-1025.
Gridelli et al., Vascular disrupting agents: a novel mechanism of action in the battle against non-small cell lung cancer, Oncologist (2009), 14(6), 612-620.
Gu et al., "Identification of CTLA-4 isoforms produced by alternative splicing and their association with myasthenia gravis," Clinical Immunology (Sep. 2008) vol. 128, Issue 3, pp. 374-381.
Gura, Trisha, "Cancer Models: Systems for Identifying New Drugs are Often Faulty", Science 7(Nov. 1997) 278(5340): 1041-1042.
Hamel, E. "Antimitotic Natural Products and Their Interactions with Tubulin." Med. Res. Rev. (1996) 16(2): 207-31.
Hartwell et al. "Checkpoints: Controls that Ensure the Order of Cell Cycle Events." Science. 246, 629-34 (1989).
Hayakawa, Structure-activity relationship analysis, Japanese Journal of Cancer and Chemotherapy, (2004), 31(4):526-528.
Hayashi et al., "Total Synthesis of Anti-microtubule Diketopiperazine Derivatives: Phenylahistin and Aurantiamine," J. Org. Chem., (2000) 65: 8402-8405.
Hayashi et al., Medicinal chemistry and chemical biology of diketopiperazine-type antimicrotubule and vascular-disrupting agents, Chemical & Pharmaceutical Bulletin (2013), 61(9), 889-901.
Hayashi et al., Small peptide-based medicinal chemistry for intractable disease, Peptide Science (2009), Volume Date 2008, 45th, 139-140.
He et al., "Low-dose paclitaxel enhances the anti-tumor efficacy of GM-CSF surface-modified whole-tumor-cell vaccine in mouse model of prostate cancer," Cancer Immunology Immunotherapy (2011) vol. 60, No. 5, pp. 715-730. Abstract.
Heist et al., "Abstract C30: Phase 1/2 study of the vascular disrupting agent (VCA) plinabulin (NPI-2358) combined with docetaxel in patients with non-small cell lung cancer (NSCLC)," Mol. Cancer Ther., 2009; 8(12 Suppl):C30, 2 pages.
Heist et al., "Randomized Phase 2 Trial of Plinabulin (NPI-2358) Plus Docetaxel in Patients with Advanced Non-Small Lung Cancer (NSCLC)," 2014 ASCO Annual Meeting. . (abstr 8054) Poster Presentation. Retrieved from the internet Jul. 17, 2017: <http://meetinglibrary.asco.org/record/92548/poster>.
Heist et al., "Randomized phase 2 trial of plinabulin (NPI-2358) plus docetaxel in patients with advanced non-small cell lung cancer (NSCLC)." J. Clin. Oncol. (2014) vol. 32, No. 5s, (suppl; abstr 8054).
Helleman et al. "The International Journal of Biochemistry & Cell Biology," vol. 42, pp. 25-30 (2010).
Hellmann et al., Nov. 21, 2019, Nivolumab plus ipilimumab in advanced non-small-cell lung cancer, The New England Journal of Medicine, 381:2020-2031.
Hodi et al., Nov. 2016, Combined nivolumab and ipilimumab versus ipilimumab alone in patients with advanced melanoma: 2-year overall survival outcomes in a multicentre, randomised, controlled, phase 2 trial, Lancet Oncol., 17:1558-1568.
Horak et al. "Structures of the Austalides A-E, Five Novel Toxic Metabolites from Aspergillus ustus." J Chem Soc Chem Commun. (1981) 1265-67.
http://scienceandresearch.homeoffice.gov.uk/animal-research/publications-and-reference/001-abstracts/abstracts2-2006/02november-2006/457?view=Html; "Abstract #457, Animals in Scientific Procedures (2006)"; (accessed on Nov. 19, 2008).
Hursthouse et al., "Why Do Organic Compounds Crystallise Well or Badly or Ever so Slowly? Why Is Crystallisation Nevertheless Such a Good Purification Technique?," Organic Process Res & Devel (2009) vol. 13, No. 6, pp. 1231-1240.
Hwang et al., 2019, Heat shock proteins: a dual carrier-adjuvant for an anti-drug vaccine against heroin, Bioorganic & Medicinal Chemistry, 27:125-132.
Hyun et al., "Valine dehydrogenase from Streptomyces albus: gene cloning, heterologous expression and identification of active site by site-directed mutagenesis," FEMS Microbiology Letters (Jan. 1, 2000) 182: 29-34.
Intlekofer et al., Jul. 2013, At the bench: preclinical rationale for CTLA-4 and PD-1 blockade as cancer immunotherapy, J. Leukoc Biol., 94(1):25-39.
Iwasaki, S. "Antimitotic Agents: Chemistry and Recognition of Tubulin Molecule." Med Res Rev. (1993) 13: 183-198.
Iwasaki, S. "Bioactive Natural Products Interfering with Microtubule Function." Kagaku to Seibutsu. 32(3): 153-159 (1994).
Ji et al., Tubulin Colchicine Binding Site Inhibitors as Vascular Disrupting Agents in Clinical Developments, Current Medicinal Chemistry (2015), 22(11), 1348-1360.
Jiang et al., "A Novel Peptide Isolated from a Phage Display Peptide Library with Trastuzumab Can Mimic Antigen Epitope of HER-2*," (Feb. 11, 2005) J Biol Chem, vol. 280, No. 6, pp. 4656-4662.
Johnson et al. "Kinetic Analysis of Microtubule Self-assembly in Vitro." J. Mol. Biol. 117, 1-31 (1977).
Jure-Kunkel M. et al., "Synergy between chemotherapeutic agents and CTLA-4 blockade in preclinical tumor models", Cancer Immunol. Immunother. 2013, vol. 62, pp. 1533-1545.
Kakoulidou et al., "Human Soluble CD80 is Generated by Alternative Splicing, and Recombinant Soluble CD80 Binds to CD28 and CD152 Influencing T-cell Activation," Scandinavian J. Immunol (Nov. 2007) 66(5):529-537.
Kamb, Alexander, "What's wrong with our cancer models?", Nature Reviews Drug Discovery (Feb. 2005) 4: 161-165.
Kanoh et al., "(−)-Phenylahistin: A New Mammalian Cell Cycle Inhibitor Produced by Aspergillus USTUS," Bioorganic & Medicinal Chemistry Letters, (1997) 7: 2847-2852.
Kanoh et al., "(−)-Phenylahistin Arrests Cells in Mitosis by Inhibiting Tubulin Polymerization," The Journal of Antibiotics, (1999) 52: 134-141.
Kanoh et al., "Antitumor Activity of Phenylahistin in Vitro and in Vivo," Bioscience Biotechnology Biochemistry, (1999) 63(6): 1130-1133.
Kanoh et al., "Synthesis and Biological Activities of Phenylahistin Derivatives," Bioorganic & Medicinal Chemistry, (1999) 7: 1451-1457.
Kanojia et al., May 2015, βIII-tubulin regulates breast cancer meastases to the brain, Mol Cancer Ther., 14(5):1152-1161.
Kanthou et al., Microtubule depolymerizing vascular disrupting agents: novel therapeutic agents for oncology and other pathologies, International Journal of Experimental Pathology(2009), 90(3), 284-294.
Kanzaki et al., A Novel Potent Cell Cycle Inhibitor Dehydrophenylahistin-Enzymatic Synthesis and Inhibitory Activity toward Sea Urchin Embryo, The Journal of Antibiotics, (Dec. 2002) 55(12):1042-1047.
Kanzaki et al., "Effective Production of Dehydro Cyclic Dipeptide Albonoursin Exhibiting PronuclearFusion Inhibitory Activity, I. Taxonomy and Fermentation," The Journal of Antibiotics, (1999) 52: 1017-1022.
Kanzaki et al., "Effective Production of Dehydro Cyclic Dipeptide Albonoursin Exhibiting Pronuclear Fusion Inhibitory Activity, II. Biosynthetic and Bioconversion Studies," The Journal of Antibiotics, (2000) 53(1): 58-62.

(56) References Cited

OTHER PUBLICATIONS

Kanzaki et al., "Enzymatic dehydrogenation of cyclo(L-Phe-L-Leu) to a bioactive derivative, albonoursin," Journal of Molecular Catalysis B: Enzymatic (1999) 6(3): 265-270.
Kanzaki et al., "Enzymatic Synthesis of Physiologically Active Substances Utilizing a Novel System for the Synthesis of Diketopiperazines Comprising Dehydroamino Acids as Constituents," Abstracts of Papers Presented at the 1999 Meeting of the Society for Actinomycetes Japan, (1999) 42 (Abstract Only).
Kanzaki et al., "Novel Cyclic Dipeptide Dehydrogenase and Assay Method for Its Activity," Scientific Reports of the Faculty of Agriculture, Okayama University, (1999) 88: 7-11.
Kashyap et al., Sep. 24, 2019, GEF-H1 signaling upon microtubule destabilization is required for dendritic cell activation and specific anti-tumor responses, Cell Reports, 28:3367-3380.
Keepers et al. "Comparison of the Sulforhodamine B Protein and Tetrazolium (MTT) Assays for in vitro Chemosensitivity Testing." Eur. J. Cancer. 27, 897-900 (1991).
Kim et al. "Polymer attached cyclic peptides, tetrahedron: Asymmetry." 3(11):1421-1430 (1992).
Kingston, Correction to Tubulin-interactive natural products as anticancer agents, Journal of Natural Products (2011), 74(5), 1352.
Kingston, Tubulin-Interactive Natural Products as Anticancer Agents, Journal of Natural Products (2009), 72(3), 507-515.
Kobayashi et al., "Microtubule Assembly Regulators of Microbial Origin," Abstract of Paper Read at the 1989 Symposium on the Chemistry of Natural Products, (1989) 51.
Kola et al., "Can the pharmaceutical industry reduce attrition rates?", Nature Reviews Drug Discovery (2004) 3: 711-715.
Kondoh et al. "Effects of Tryprostatin Derivatives on Microtubule Assembly In Viro and In Situ." J. Antibiotics. 51, 801-04 (1998).
Kopple et al., "A Convenient Synthesis of 2,5-Piperazinediones 1a," The Journal of Organic Chemistry, (1967) 33: 862-864.
Kreamer K., "Immune checkpoint blockade: A New Paradigm in Treating Advanced Cancer", J. Adv. Pract. Oncol., 2014, vol. 5, pp. 418-431.
Krendel et al., Apr. 2002, Nucelotide exchange factor GEF-H1 mediates cross-talk between microtubules and the actin cytoskeleton, Nature Cell Biology, 4:294-301 and supplementary information.
Krishan, A. "Rapid Flow Cytofluorometric Analysis of Mammalian Cell Cycle By Propidium lodide Staining." J. Cell Biol. 66, 188-193 (1975).
Kupchan et al. "Steganacin and Steganangin, Novel Antileukemic Lignan Lactones from Steganotaenia araliacea 1-3." J. Am. Chem. Soc. (1973) 95(4): 1335-36.
Küster & Koeppenhöfer, "Über eininge Pyrrolderivate," Z. Physiol, Chem., (1927) 172:126-137.
Lacey et al. "Interaction of Phomopsin A and Related Compounds with Purified Sheep Brain Tubulin." Biochem. Pharmacol. 36, 2133-38 (1987).
Laemmli, U.K. "Cleavage of Structural Proteins during the Assembly of the Head of Bacteriophage T4." Nature. 227, 680-85 (1970).
Larsen et al. "Aurantiamine, A Kiketopiperazine from Two Varieties of Penicillium Aurantiogriseum." Phytochemistry. 31, 1613-1615 (1992).
Leaf, Clifton, "Why are we losing the war on cancer (And how to win it)?", Health Administrator (2005) XVII(1): 172-183.
Lee et al. "The Reconstitution of Microtubules from Purified Calf Brain Tubulin." Biochemistr. 14(23), 5183-87 (1975).
Lee et al., "A practical guide to pharmaceutical polymorph screening & selection," Asian Journal of Pharmaceutical Sciences (2014) vol. 9, pp. 163-175.
Lee et al., Colchicine site inhibitors of microtubule integrity as vascular disrupting agents, Drug Development Research (2008), 69(6), 352-358.
Li et al., May-Jun. 2017, Epitope mapping reveals the binding mechanism of a functional antibody cross-reactive to both human and murine programmed death 1, MABS, 9(4):628-637.
Li, Y., et al. "Interaction of marine toxin dolastatin 10 with porcine brain tubulin: competitive inhibition of rhizoxin and phomopsin A binding." Chem. Biol. Interact. 93, 175-83 (1994).
Liao et al., "Design and synthesis of novel soluble 2,5-diketopiperazine derivatives as potential anticancer agents," European J Med Chem (2014) 83:236-244.
Liou et al., Aug. 12, 2004, Concise synthesis and structure-activity relationships of combretastatin A-4 analogues, 1-aroylindoles and 3-aroylindoles, as novel classes of potent antitubulin agents, Journal of Medicial Chemstry, 47(17):4247-4257.
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) 21(7) 1639-1651.
Liwo et al. "Origin of the Ring-Ring Interaction in Cyclic Dipeptides Incorporating an Aromatic Amino Acid." Tetrahedron Lett. 26, 1873-1876 (1985).
Lloyd et al., 2015, Abstract A184: Activity of plinabulin in tumor models with kras mutations, Mol. Can. Thera. 14(12): Suppl. 2.
Lloyd et al., Abstract A07: Plinabulin: Evidence for an immune-mediated mechanism of action, In: Proceedings of the AACR Special Conference: Function of Tumor Microenvironment in Cancer Progression; Jan. 7-10, 2016; San Diego, CA. Philadelphia (PA): AACR; Cancer Research. Aug. 2016. 76(15 Supp.): abstract nr A07.
Lu et al., Nov. 2012, An overview of tubulin inhibitors that interact with the colchicine binding site, Pharmaceutical Research, 29(11):2943-2971.
Luduena, R.F. "Contrasting Roles of Tau and Microtubule-associated Protein 2 in the Vinblastine-induced Aggregation of Brain Tubulin." J. Biol. Chem. 259: 12890-98 (1984).
Lyman et al., "Risk Models for Predicting Chemotherapy-Induced Neutropenia," The Oncologist (2005) 10:427-437.
Lynch et al., "Ipilimumab in Combination With Paclitaxel and Carboplatin As First-Line Treatment in Stage IIIB/IV Non-Small-Cell Lung Cancer: Results From a Randomized, Double-Blind, Multicenter Phase II Study," (Jun. 10, 2012) J Clin Oncol, vol. 30, No. 17, pp. 2046-2054.
Mahindroo et al., "Antitubulin Agents for the Treatment of Cancer—A Medicinal Chemistry Update", Expert Opin. Ther. Patents (2006) 16(5): 647-691.
Mahoney et al., "The Next Immune-Checkpoint Inhibitors: PD-1/PD-L1 Blockade in Melanoma," Clinical Therapeutics (Apr. 2015) vol. 37, Issue 4, pp. 764-782. Abstract.
Matsuda et al., "Pilot study of WT1 peptide-pulsed dendritic cell vaccination with docetaxel in esophageal cancer," Oncology Letters (Jul. 2018) vol. 16, No. 1, pp. 1348-1356.
Melero et al., Aug. 2015, Evolving synergistic combinations of targeted immunotherapies to combat cancer, Nature Reviews Cancer, 15:457-472.
Millward et al., "Phase I trial of NPI-2358 (a novel vascular disrupting agent) plus docetaxel," J. Clin. Oncol. (May 2009) 27(15S): 3571-3571, Abstract.
Millward et al., "Phase 1 study of the novel vascular disrupting agent plinabulin (NPI-2358) and docetaxel," The Journal of New Anticancer Agents, vol. 3, No. 30, Feb. 16, 2011 plinabulin (NPI-2358) and docetaxel, Investigational New Drugs (2011), 30(3), 1065-1073.
Mita et al., "Phase 1 First-in-Human Trial of the Vascular Disrupting Agent Plinabulin (NPI-2358) in Patients with Solid Tumors or Lymphomas," Clinical Cancer Research (2010), 16(23), 5892-5899.
Mita et al., "Phase II study of docetaxel with or without plinabulin (NPI-2358) in patients with non-small cell lung cancer (NSCLC)", *J. Clin. Oncol.*, 2010, vol. 28, No. 15 supplement. Abstract 7592, 2 pages.
Mita et al., Randomized Phase 2 Study of Docetaxel +/− Plinabulin (NPI-2358) in Patients with Non-Small Cell Lung Cancer (NSCLC), *Poster Presentation at ACS Annual '10 Meeting* (Jun. 4-8, 2010) 1 page.
Mitsudomi et al., "Mutations of ras genes distinguish a subset of non-small-cell lung cancer cell lines from small-cell lung cancer cell lines," *Oncogene* (Aug. 1991) vol. 6, No. 8, pp. 1352-1362.

(56) References Cited

OTHER PUBLICATIONS

Mohanlal et al., "The plinabulin/docetaxel combination to mitigate the known safety concerns of docetaxel," J Clin Oncol (2016) 34(15_suppl), Abstract e20595.
Mohanlal et al., Feb. 10, 2018, Plinabulin, a novel small molecule clinical stage I0 agent with anti-cancer activity, to prevent chemo-induced neutropenia and immune related AEs, Journal of Clinical Oncology, 36(5 Suppl):126.
Muguruma et al., OP-20: "Application of Fc-selective Z33-peptide to the preparation of non-covalent-type antibody-antimocrotubule plinabulin conjugate," 34th European Peptide Symposium 2016 & 8th International Peptide Symposium, Journal of Peptide Sci (Sep. 5, 2016—5:30pm) 22 Supplement 2 ISSN: 1099-1387 In English (Oral Presentation). Abstract.
Nabholz, 2001, Phase II study of docetaxel, doxorubiin, and cyclophosphamide as first-line chemotherapy for metastatic breast cancer, Journal of Clinical Oncology, 19:314-321.
Nagaria et al., "Flavopiridol Synergizes with Sorafenib to Induce Cytotoxicity and Potentiate Antitumorigenic Activity in EGFR/HER02 and Mutant RAS/RAF Breast Cancer Model Systems," Neoplasia (Aug. 2013) vol. 15, No. 8, pp. 939-951.
Natoli et al., Mar. 3, 2021. Plinabulin, a distinct microtubule-targeting chemotherapy, promotes M1-like macrophage polarization and anti-tumor immunity, Frontiers in Oncology, 11:1-14.
Neidle, Stephen, ed., Cancer Drug Design and Discovery , 9th Edition, Elsevier/Academic Press, (2008) Chapter 18, pp. 427-431.
Nema et al., Excipients and Their Role in Approved Injectable Products: Current Usage and Future Directions, PDA J Pharm Sci and Tech 2011, 65 287-332.
Neuteboom et al., "450 Poster NPI-2358, a novel tumor vascular disrupting agent potentiates the anti-tumor activity of docetaxel in the non small cell lung cancer model MV522," EJC Supplements (2008) 6(12):141.
Nicholson et al., NPI-2358 is a tubulin-depolymerizing agent: in-vitro evidence for activity as a tumor vascular-disrupting agent, Anti-Cancer Drugs (2005), Volume Date 2006, 17(1), 25-31.
Nielsen et al., Jun. 2005, Alternative splice variants of the human PD-1 gene, Cell Immunol., 235(2):109-116.
Niemann et al., "The Synthesis of the Three Isomeric dl-β-Pyridylalanines" Journal of the American Chemical Society, (1942) 64(7):1678-1682.
Nihei et al., "Evaluation of antivascular and antimitotic effects of tubulin binding agents in solid tumor therapy", Jpn. J. Cancer. Res. 1999, 90, 1387-1395.
Nitecki et al., "A Simple Route to Sterically Pure Diketopiperazines1," The Journal of Organic Chemistry, (1968) 33:864-866.
Ohaegbulam et al., "Human cancer immunotherapy with antibodies to the PD-1 and PD-L1 pathway," Trends Mol Med, (Oct. 30, 2014) 21(1): pp. 24-33.
Ott et al., "CTLA-4 and PD-1/PD-L1 Blockade: New Immunotherapeutic Modalities with Durable Clinical Benefit in Melanoma Patients," Clin Cancer Res (Oct. 1, 2013) 19(19): pp. 5300-5309.
Paik et al., "A Phase 2 Study of Weekly Albumin-Bound Paclitaxel (Abraxane®) Given as a Two-Hour Infusion", Cancer Chemother. Pharmacol., Nov. 2011, vol. 68, No. 5, pp. 1331-1337.
Pardoll et al., "The blockade of immune checkpoints in cancer immunotherapy," Nat Rev Cancer (May 4, 2016) 12(4): 252-264.
Pattingre et al., "Amino Acids Interfere with the ERK1/2-dependent Control of Macroautophagy by Controlling the Activation of Raf-1 in Human Colon Cancer HT-29 Cells," J Biol Chem (May 9, 2003) vol. 278, No. 19, pp. 16667-16674.
Perez, Edith A., "Paclitaxel in Breast Cancer," *The Oncologist*, 1998, vol. 3, pp. 373-389.
Petrillo et al., Novel VEGF-independent strategies targeting tumor vasculature: clinical aspects, Current Pharmaceutical Design (2012), 18(19), 2702-2712.
Pettit et al. "Antineoplastic Agents. 291. Isolation and Synthesis of Combretastatins A-4, A-5, and A-6 1a." J. Med. Chem. (1995) 38: 1666-1672.
Prior et al., "A Comprehensive Survey of Ras Mutations in Cancer" *Cancer Res.* (2012) vol. 72, No. 10, pp. 2457-2467.
PRNnewswire.com, Jun. 22, 2010, Nereus Pharmaceuticals completes enrollment of phase 2 advance clinical trial of plinabulin in non-small cell lung cancer, 4 pp.
Rathkopf, Jun. 20, 2008, Phase II trial of docetaxel with rapid androgen cycling for progressive noncastrate prostate cancer, J. Clin. Onc. 26(18):2959-2965.
Raza et al., 2014, Polymorphism: the phenomenon affecting the performance of drugs, SOJ Pharmacy & Pharmaceutical Sciences, 10 pp.
Reck, M., "What future opportunities may immuno-oncology provide for improving the treatment of patients with lung cancer?" (2012) Annals of Oncology (Sep. 2012) 23 (Supp. 8) viii28-viii34.
Remington, "The Science and Practice of Pharmacy, 20th Ed" (2000) p. 709.
Rhodes, John, "Section Review: Biologicals & Immunologicals: Therapeutic potential of Schiff base-forming drugs," Expert Opinion on Investigational Drugs (1996) vol. 5, Issue 3, pp. 257-268.
Riedel et al., Jun. 2007, A phase II trial of carboplatinvinorelbine with pegfilgrastim support for the treatment of patients with advanced non-small cell lung cancer, Journal of Thoracic Oncology, 2(6):520-525.
Riemer et al., "Matching of trastuzumab (Herceptin®) epitope mimics onto the surface of Her-2/neu—a new method of epitope definition," Mol Immunol 42 (2005) pp. 1121-1124.
Roberge et al., "Antitumor Drug Fostriecin Inhibits the Mitotic Entry Checkpoint and Protein Phospatases 1 and 2A." Cancer Res. 54, 6115-21 (1994).
Roberts et al., "Trends in the Risks and Benefits to Patients with Cancer Participating in Phase 12 Clinical Trials", JAMA (2004) 292(17): 2130-2140.
Rowinsky et al., "The clinical pharmacology and use of antimicrotubule agents in cancer chemotherapeutics", Pharmacol. Ther. 1991, 52, 35-84.
Rowinsky et al. "Taxol: A Novel Investigational Antimicrotubule Agent." J. Natl. Cancer Inst. 82(15): 1247-59 (1990).
Rozali et al., "Programmed Death Ligand 2 in Cancer-Induced Immune Suppression," Clinical and Developmental Immunology (2012) Article ID 656340, pp. 1-8.
Sackett, D.L. "Podophyllotoxin, Steganacin and Combretastatin: Natural Products that Bind at the Colchicine Site of Tubulin." Pharmacol. Ther. (1993) 59: 163-228.
Saito et al., "Synthesis of novel octahydro-1, 5-imino-3-benzazocin-4, 7, 10-trione derivatives having a methyl group at the C-2 position as ABC ring models of saframycins," Chemical & Pharmaceutical Bulletin (1997) 45(7):1120-1129.
Scholl et al., "Synthetic Lethal Interaction between Oncogenic KRAS Dependency and the STK33 Suppression in Human Cancer Cells", Cell (May 29, 2009) 137 pp. 821-834.
Selby et al., Sep. 9, 2016, Preclinical development of ipilimumab and nivolumab combination immunotherapy: mouse tumor models, in vitro functional studies, and cynomolgus macaque toxicology, PloS One, 11(9):e0161779, 19 pp.
Sele et al., Jul. 2016, Novel 4-(pyrimidin-2-yl)morpholines targeting the colchicine-binding site of tubuline, Cancer Research, 76(14):abstract 1364.
Sezaki et al., "Drug Delivery Systems", Drug Development, (Jul. 1989) 13: 116, Table 2. 29.
Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.
Shen et al., Time- and dose-dependent vascular changes induced by the novel vascular disrupting drug NPI-2358 in a murine cancer model monitored with DCE-MRI, U.S. Chinese Journal of Lymphology and Oncology(2010), 9(4), 151-153.
Sherline et al. "Binding of Colchicine to Purifiied Microtubule Protein." J. Biol. Chem. 250, 5481-86 (1975).
Shi, Q et al, "Recent progress in the development of tubulin inhibitors as antimitotic antitumor agents", Curr. Pharm. Des. 1998, 4, 219-248.

(56) References Cited

OTHER PUBLICATIONS

Singh et al., "A novel vascular disrupting agent plinabulin triggers JNK-mediated apoptosis and inhibits angiogenesis in multiple myeloma cells," Blood (2011), 117(21), 5692-5700.
Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.
Smedsgaard et al. "Using direct electrospray mass spectrometry in taxonomy and secondary metabolite profiling of crude fungal extracts." J. Microbiol. Meth. (1996) 25: 5-17.
Snegovoy AV, et al. Practical recommendations for the appointment of colony-stimulating factors in order to prevent the development of febrile neuropathy in cancer patients // Practical recommendations. Version 2016. p. 394-401.
Sölter et al., Barettin, Revisited? Tetrahed Lttrs. (Mar. 2002) 43: 3385-3386.
Spain et al., Feb. 6, 2016, Management of toxicities of immune checkpoint inhibitors, Cancer Treatment Reviews, 44:51-60.
Spear et al., Vascular disrupting agents (VDA) in oncology: advancing towards new therapeutic paradigms in the clinic, Current Drug Targets (2011), 12(14), 2009-2015.
Stein, J., ed. "Internal Medicine," Fourth Edition, Mosby-Year Book, Inc., (1994), Chapters 71-72, pp. 699-729.
Stenehjem et al., "PDI/PDLI inhibitors for the treatment of advanced urothelial bladder cancer," OncoTargets and Therapy (2018) 11:5973-5989.
Steyn, P.S. "The Structures of Five Diketopiperazines from Aspergillus Ustus." Tetrahedron. 29, 107-120 (1973).
Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).
Takahashi et al. "Rhizoxin binding to tubulin at the maytansine-binding site." Biochim. Biophys. Acta. 926, 215-23 (1987).
Talmadge et al., Murine models to evaluate novel and conventional therapeutic strategies for cancer., Am J Pathol, 2007, vol. 170, Issue 3, pp. 793-804.
Thorpe, Philip E., "Vascular Targeting Agents as Cancer Therapeutics," Clinical Cancer Research, vol. 10, 415-427, Jan. 15, 2004.
Tiwari et al. "A pH- and Temperature-Dependent Cycling Method that doubles the Yield of Microtubule Protein." Anal. Biochem. 215, 96-103 (1993).
Tonra et al., "Predictive models for tumour cell targeting with plinabulin, derived from in vitro screening and Affymetrix mRNA expression data," Proc Am Assoc Cancer Res (2019) vol. 60, p. 321, Abstract #1254.
Topalian et al., "Safety, Activity, and Immune Correlates of Anti-PD-1 Antibody in Cancer," N Engl J Med. (Jun. 28, 2012) 366(26):2443-2454.
Tozer et al., Tumour vascular disrupting agents: combating treatment Resistance, British Journal of Radiology (2008), 81(Spec. Iss. 1), S12-S20.
Turner et al. "Recent Advances in the Medicinal Chemistry of Antifungal Agents." Current Pharmaceutical Design. 2, 209-224 (1996).
US Food and Drug Administration, Highlights of prescribing information, retrieved Apr. 16, 2020 from https://www.accessdata.fda.gov/drugsatfda_docs/label/2015/125031s180lbl.pdf, Rev. Nov. 2015, Reference ID:4192944.
Usui et al. "Tryprostatin A, a specific and novel inhibitor of microtubule assembly." Biochem J. 333, 543-48 (1998).
Vainas, 2012, Personalising docetaxel and G-CSF schedules in cancer patients by a clinically validated computational model, British J. Cancer, 107:814-822.
Van der Waerden, B.L., "Wirksamkeits- und Konzentrationsbestimmung durch Tierversuche." Arch Exp Pathol Pharmakol. 195, 389-412, (1940).
Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).
Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.
Wailoo, 2009, The risk of febrile neutropenia in patients with non-small-cell lung cancer treated with docetaxel: a systematic review and meta-analysis, British J. Cancer 100(3):436-441.
Wang, T. et al. 1998 "Microtubule interfering agents activate c-Jun N-terminal kinase/stress-activated protein kinase through both Ras and apoptosis signal-regulating kinase pathways". J Biol Chem. vol. 273, No. 9, pp. 4928-4936.
Wang, Y. et al., "Structures of a diverse set of colchicine binding site inhibitors in complex with tubulin provide a rationale for drug discovery." FEBS Journal (2016) 283, 102-111.
Weisenberg et al. "The Colchicine-Binding Protein of Mammalian Brain and its Relation to Microtubules." Biochemistry (1968) 7(12): 4466-79.
Wilt et al. "Anal cancer in Alaska; a retrospective study of incidence, treatment, and outcomes". Alaska Med Jul.-Sep. 2002; 44(3):56-9, 62.
Yahara et al. "Microtubule Organization of Lymphocytes and its Modulation by Patch and Cap Formation." Cell. 15, 251-259 (1978).
Yamato et al., "Clinical importance of B7—H3 expression in human pancreatic cancer," British Journal of Cancer (Oct. 20, 2009) 101, pp. 1709-1716.
Yamazaki et al. "Crystal Structure and Absolute Configuration of Fumitremorgin B, a Tremorgenic Toxin from Aspergillus Fumigatus Fres." Tetrahedron Lett. 1, 27-28 (1975).
Yamazaki et al. "Synthesis and Structure-Activity Relationship Study of Antimicrotubule Agents Phenylahistin Derivatives and a Didehydropiperazine-2,5-dione Structure", Journal of Medicinal Chemistry, 2012, vol. 55, No. 3, pp. 1056-1071.
Yamazaki et al., Drug discovery study on cyclic dipeptides anti-cancer drugs and chemical biological development, Idenshi Igaku Mook (2012), 21(Saishin Pepuchido Gosei Gijutsu to Sono Soyaku Kenkyu eno Oyo), 260-266.
Yamori T., "A Human Cell Line Panel for Screening Anti-Cancer Drugs", Jap. J. Cancer Chemother. 24, 129-35 (1997).
Yang et al., "The KRAS Mutation is Highly Correlated With EGFR Alterations in Patients With Non-small Cell Lung Cancer," Fooyin J Health Sci (2009) vol. 1(2): pp. 65-71.
Yeh et al., "A Phase 1 Trial Combining Plinabulin and Nivolumab for Metastatic Squamous NSCLC," International Association for the Study of Lung Cancer, Journal of Thoracic Oncology (Sep. 6, 2015) Abstract 602, p. 2.01-087.
Yin et al., "Human Mutations That Confer Paclitaxel Resistance," Mol. Cancer Ther. vol. 9(2), pp. 327-335 (2010).
Yokio et al., "Neihumicin, A New Cytotoxic Antibiotic From Micromonospora Neihuensis," The Journal of Antibiotics, (Apr. 1988) 41(4):494-501.
Yoshida, M.M. Protein Nucleic Acid Enzymes. 38, 1753-1765 (1993).
Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).
Younis et al., 2011, The cost-utility of adjuvant chemotherapy using docetaxel and cylophosphamide compared with doxorubicin and cyclophosphamide in breast cancer, Current Oncology 18(8):e298-3296.
Zacharie et al., 1997, Regioselective synthesis of 6-substituted 2-hydroxybenzaldehyde: efficient synthesis of the immunomodulator tucaresol and related analogues, Journal of the Chemical Society, 19:2925-2929.
Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.
Zheng, Lei, "Does vaccine-primed pancreatic cancer offer better candidates for immune-based therapies?" Immunotherapy (2014) 6(10):1017-1020.

(56) References Cited

OTHER PUBLICATIONS

Zou et al., Effect of Interleukin-1 Blockers, CK112, and CK116 on Rat Experimental Choroidal Neovascularization In Vivo and Endothelial Cell Cultures In Vitro, J Ocul Pharma Thera., (2006) 22(1): 19-25.
International ISR/WO mailed Mar. 29, 2018 for PCT/US2018/012668—DALWC. 126WO.
Bauer et al., Jan. 15, 2010, Identification of markers of taxane sensitivity using proteomic and genomic analyses of breast tumors from patients receiving neoadjuvant paclitaxel and radiation, Clinical Cancer Research, 16(2):681-690.
Bazhenova, Feb. 21, 2021, Nivolumab in Combination With Plinabulin in Patients With Metastatic Non-Small Cell Lung Cancer (NSCLC), ClinicalTrials.gov, NCT02812667 version 7.
Berenbaum, Jun. 1989, What is synergy?, Pharmacol. Rev., 41(2):93-141.
Bigioni et al., Sep. 2008, Antitumour effect of combination treatment with Sabarubicin (MEN 10755) and cis-platin (DDP) in human lung tumour xenograft, Cancer Chemother. Pharmacol., 62(4):621-629.
Blankenstein et al., Mar. 1, 2012, The determinants of tumour immunogenicity, Nat. Rev. Cancer, 12(4):307-313.
Champiat et al., Feb. 2014, Incorporating immune-checkpoint inhibitors into systemic therapy of Nsclc, J. Thorac. Oneal., 9(2):144-153.
Chang et al., 1998, Changing residue 338 in human factor IX from arninine to alanine causes an increase in catalytic activity, J. Biol. Chem., 272(9):4929-4936.
Clezardin et al., Jan. 1, 2011, Bisphosphonates' antitumor activity: an unravelled side of a multifacted drug class, Bone, 48(1):71-79.
Clinicaltrials.gov, NCT00151073, Estramustine, docetaxel and zoledronate treatment in hormone-refractory adenocarcinoma of the prostate, https//clinicaltrials.gov/ct2/show/NCT00151073?term=zoledronate%2C+tubulin&draw=2&rank=1.
Davies, Feb. 3, 2014, New modalities of cancer treatment for NSCLC: focus on immunotherapy, Cancer Manag. Res., 6:63-75.
Dennis, Aug. 17, 2006, Off by a whisker, Nature, 442:739-741.
Du et al., Jul. 2018, docetaxel increases the risk of severe infections in the treatment of non-small cell lung cancer: a meta-analysis, Oncosciene, 5(7-8):220-238.
Duarte et al., 2022, Evaluation of synergism in drug combinations and reference models for future orientations in oncology, Curr. Res. Pharmacol. Drug Discov., 3:100110; pp. 1-13.
Dyson, Feb. 16, 2017, 4 Clinical Pearls for Granulocyte Colony Stimulating Factors (G-CSFs), Pharmacy Times, retrieved from the internet at URL <https://www.pharmacytimes.com/view/4-clinical-pearls-for-granulocyte-colony-stimulating-factors-g-csfs>, (retrieved on Dec. 11, 2023), Feb. 16, 2017.
El-Kenawi et al., Oct. 2013, Angiogenesis inhibitors in cancer therapy: mechanistic perspective on classification and treatment rationales, Br. J. Pharmacol., 170(4):712-729.
Elliott et al., Oct. 15, 1989, Sequence and schedule-dependent synergy of trimetrexate in combination with 5-fluorouracil in vitro and in mice, Cancer Res., 49(20):5586-5590.
Fan et al., 2021, Immunotherapy in colorectal cancer; current achievements and future perspective, Int. J. Biol. Sci., 17(14):3837-3849.
Flanigan et al., Jan. 7, 2011, Melanoma brain metasteses: is it time ro reassess the bias?, Current Problems in Cancer, 35(4):200-210.
Friedman et al., 2000, Schedule-dependent activity of irinotecan plus BCNU against malignant glioma xenografts, Cancer Chemother. Pharmacol., 45(4):345-349.
Garcia-Fuente et al., 2018, CISNA: an accurate description of dose-effect and synergism in combination therapies, Sci. Rep., 8:4964; pp. 1-9.
Glisson et al., 2002, Phase II trial of docetaxel and cisplatin combination chemotherapy in patients with squamous cell carcinoma of the head and neck, Journal of Clinical Oncology 20:1593-1599.
Hellmann et al., May 31, 2018, Nivolumab plus ipilimumab in lung cancer with a high tumor mutational burden, N. Engl. J. Med., 378(22):2093-2104.
Ishibashi et al., Sep. 1989, Interleukin-6 is a potent thrombopoietic factor in vivo in mice, Blood, 74(4):1241-1244.
Januchowski et al., Jan. 2014, Microarray-based detection and expression analysis of extracellular matrix proteins in drug-resistant ovarian cancer cell lines, Oncology Reports, 32:1981-1990.
Jin et al., Feb. 28, 2022, Different syngeneic tumors show distinctive intrinsic tumor-immunity and mechanisms of actions (MOA) of anti-PD-1 treatment, Sci. Rep., 12: 3278, pp. 1-18.
Kwon et al., Apr. 2013, Mouse models for lung cancer, Mol. Oneal., 7(2):165-177.
La-Beck, 2021, Repurposing amino-bisphosphonates by liposome formulation for a new reole in cancer treatment, Seminars in Cancer Biology, 68:175-185.
Liu et al., Dec. 31, 2019, Spectrum of EGFR aberrations and potential clinical implications, insights from integrative pan-cancer analysis, Cancer Communications, 40(1):43-59.
Lloyd et al. Dec. 2003, NPI-2358 and 2386: two new vascular/tubulin modifying agents greatly potentiate standard chemotherapy in xenograft models, Clin. Cancer Res., 9 6153s; Abstract #B59, 1 p.
Lyman, 2011, Neutropenia, Encyclopedia of Cancer, pp. 2506-2509.
Malhotra, J., "A Phase I/II Study of Nivolumab, Ipilimumab and Plinabulin in Patients With Recurrent Small Cell Lung Cancer", ClinicalTrials.gov, NCT03575793 version 9, Apr. 15, 2020, <URL: https://clinicaltrials.gov/ct2/history/NCT03575793?V_9=View#StudyPageTop>.
Malhotra, J., Abstract 8570: "A phase I trial of plinabulin in combination with nivolumab and ipilimumab in patients with relapsed small cell lung cancer (SCLC): Big Ten Cancer Research Consortium (BTCRC-LUN17-127) study", Journal of Clinical Oncology, vol. 39, No. 15, May 28, 2021, DOI: 10.1200/JCO.2021.39.15_suppl.8570.
Martin et al., Sep. 2014, The microtubule-depolymerizing agent ansamitocin P3 programs dendritic cells toward enhanced anti-tumor immunity, Cancer Immunol. Immunother., 63(9):925-938.
Massarelli et al., Feb. 2014, Immunotherapy in lung cancer, Transl. Lung Cancer Res., 3(1):53-63.
Mazza et al., 2017, Treating EGFR mutation resistance in non-small cell lung cancer—role of osimertinib, The Application of Clinical Genetics, 10:49-56.
Mizumoto et al., Nov. 1, 2005, Discovery of novel immunostimulants by dendritic-cell-based functional screening, Blood, 106(9):3082-3089.
Mohanlal et al., Mar. 1, 2017, Plinabulin as a novel small molecule clinical stage immuno-oncology agent for NSCLC, Journal of Clinical Oncology, 35(7), Supplement 1, Abstract 139.
Muguruma et al., 2016, Novel Hybrid Compound of a Plinabulin Prodrug with an IgG Binding Peptide for Generating a Tumor Selective Noncovalent-Type Antibody-Drug Conjugate; Bioconjugate Chem. 27(7):1606-1613.
Muller et al., 2014, Cancer chemotherapy agents target intratumoral dendritic cells to potentiate antitumor immunity, Oncoimmunology, 3(8):e954460; 4 pp.
Nereus Pharmaceuticals, Inc., Aug. 16, 2011, Phase 1/2 study of vascular disrupting agent NPI-2358 + docetaxel in patients with advanced non-small cell lung cancer, ClinicalTrials.gov, NCT00630110 <URL: https://www.clinicaltrials.gov/ct2/show/NCT00630110>.
Ouyang et al., Mar. 2024, Overcoming cold tumors: a combination strategy of immune checkpoint inhibors, Front. Immunol., 15:1344272, pp. 1-8.
Oxford English Dictionary Online, 2010, Definition of prevent, http://dictionary.oed.com/, 4 pp.
Peters et al., Oct. 9, 2020, Schedule-dependent synergy between the histone deacetylase inhibitor belinostat and the dihydrofolate reductase inhibitor pralatrexate in T-and B-cell lymphone cells in vitro, (Front. Cell Dev. Biol., 8:577215), pp. 1-10.
Peterson et al., 2004, Integrating pharmacology and in vivo cancer models in preclinical and clinical drug development, Eur. J. Cancer., 40:837-844.
Plunkett et al., Aug. 1995, Gemcitabine: metabolism, mechanisms of action, and self-potentiation, Semin Oncol., 22(4 Suppl 11):3-10.

(56) References Cited

OTHER PUBLICATIONS

Rajan et al., Dec. 2014, Nivolumab (anti-PD-1, BMS-936558, ONO-4538) in patients with advanced non-small cell lung cancer, Transl. Lung Cancer Res. 3(6):403-405.
Reagan-Shaw et al., Mar. 2007, The FASEB Journal, 22:659-661.
Recht et al., May 23, 1996, The sequencing of chemotherapy and radiation therapy after conservative surgery for early-stage breast cancer, N. Engl. J. Med., 334(21):1356-6131.
Schuh, 2004, Trials, tribulations, and trends in tumor modeling in mice, Toxicologic Pathology, 32(Suppl. 1):53-66.
Shields et al., Apr. 2023, Late-stage MC38 tumours recapitulate features of human colorectal cancer—implications for appropriate timepoint selection in preclinical studies, Front. Immunol., 14:1152035, pp. 1-23.
Tan et al., 2003, Experimental design and sample size determination for testing synergism in drug combination studies based on uniform measure, Statist. Med., 22:2091-2100.
Tang et al., Sep. 2015, What is synergy? The Saariselka agreement revisited, Front. Pharmacol., 6:181, pp. 1-5.
Tsao et al., 2004, Phase I evaluation of docetaxel and topotecan for patients with advanced solid tumores, Cancer, 100:2240-2245.
Tsoumpra et al., 2015, The inhibition of human farnesyl pyrophosphate synthase by nitrogen-containing bisphosphonates. Elucidating the roes of active site threonine 201 and tyrosine 204 residues using enzyme mutants, Bone, 81:478-486.
Valet et al., Dec. 2013, Challenging single- and multi-probesets gene expression signatures of pathological complete response to neoadjuvant chemotherapy in breast cancer: experience of the REMAGUS 02 phase II trial, Breast, 22(6):1052-1059.
Vannenman et al., Mar. 22, 2012, Combining immunotherapy and targeted therapies in cancer treatment, Nat. Rev. Cancer, 12(4):237-251.
Wang et al., 2016, The D domain of LRRC4 anchors ERK1/2 in the cytoplasm and competitively inhibits MED/ERK activation in glioma cells, Journal of Hematology & Oncology, 9:130.
Wang et al., Mar. 5, 2013, Marine-derived angiogenesis inhibitors for cancer therapy, Mar. Drugs, 11(3):903-933.
Weycker et al., 2019, Risk and consequences of chemotherapy-induced thrombocytopenia in US clinical practice, BMC Cancer, 19(151), 8 pp.
Wooten et al., Jul. 29, 2021, MuSyC is a consensus framework that unifies multi-drug synergy metrics for combinatorial drug discovery, Nat. Commun., 12(1):4607, pp. 1-16).
Yin et al., May 2018, Searching synergistic dose combinations for anticancer drugs, Front. Pharmacol., 9:535, pp. 1-7.
Yuan et al., 2019, Mathematical rules for synergistic, additive, and antagonistic effects of multi-drug combinations and their application in research and development of combinatorial drugs and special medical food combinations, Food Sci. Hum. Wellness, 8:136-141.

TUBULIN BINDING COMPOUNDS AND THERAPEUTIC USE THEREOF

INCORPORATION BY REFERENCE TO ANY PRIORITY APPLICATIONS

This application is a divisional application of U.S. patent application Ser. No. 16/476,242, filed Jul. 5, 2019, which is the U.S. National Phase of International Application No. PCT/US2018/012668 entitled TUBULIN BINDING COMPOUNDS AND THERAPEUTIC USE THEREOF, filed Jan. 5, 2018, all of which are incorporated herein by reference in their entirety.

BACKGROUND

Field of the Invention

The present invention relates to tubulin binding compounds and methods of using the compounds to inhibit proliferative disorders. Specifically, the tubulin binding compounds can be useful for inhibiting the growth of a cancer cell or a neoplastic cell or inducing tubulin depolymerization and activating GEF-H1.

Description of the Related Art

Currently, cancer therapy involves surgery, chemotherapy and/or radiation treatment to eradicate neoplastic cells in a patient. All of these approaches pose significant drawbacks for the patient. Surgery, for example, may be contraindicated due to the health of the patient or may be unacceptable to the patient. Additionally, surgery may not completely remove the neoplastic tissue. Radiation therapy is effective only when the irradiated neoplastic tissue exhibits a higher sensitivity to radiation than normal tissue, and radiation therapy can also often elicit serious side effects. With respect to chemotherapy, there are a variety of chemotherapeutic agents available for treatment of neoplastic disease. However, despite the availability of a variety of chemotherapeutic agents, chemotherapy has many drawbacks. Many chemotherapeutic agents are toxic, and chemotherapy causes significant, and often dangerous, side effects. Additionally, many tumor cells are resistant or develop resistance to chemotherapeutic agents through multi-drug resistance. Thus, there is a need for additional chemotherapeutic agents.

SUMMARY OF THE INVENTION

Some embodiments relate to a compound or a pharmaceutically acceptable salt, prodrug, or ester thereof, for use in inhibiting tubulin polymerization, the compound comprising at least four moieties selected from $L_A$, $L_B$, $L_C$, $L_D$, and $L_E$, wherein:

$L_A$ is an optionally substituted $C_{6-10}$ aryl or optionally substituted five to ten membered heteroaryl positioned to interact with one or more first tubulin residues selected from the list consisting of βT239, βL242, βL252, βI4, βY52, βF169, βY202, and βV238, wherein the distance between at least one atom of the first tubulin residues and at least one atom of the aryl or heteroaryl of the $L_A$ moiety is less than 5 Å;

$L_B$ is an optionally substituted $C_{6-10}$ aryl or optionally substituted five to ten membered heteroaryl positioned to interact with one or more second tubulin residues selected from the list consisting of βL255, βM259, βA316, αT179, βI318, wherein the distance between at least one atom of the second tubulin residues and at least one atom of the aryl or heteroaryl of the $L_B$ moiety is less than 5 Å;

$L_C$ is a moiety configured to hydrogen bond with one or more third tubulin residues selected from βG237, βC241, βS241, βV238, βE200, and βY202, wherein the distance between at least an atom of the third tubulin residues and at least one atom of the hydrogen bonding atom of the $L_C$ moiety is less than 5 Å;

$L_D$ is a moiety configured to hydrogen bond with one or more fourth tubulin residues selected from βG237, βC241, βS241, βV238, βE200, and βY202, wherein the distance between at least one atom of the fourth tubulin residues and the hydrogen bonding atom of the $L_D$ moiety is less than 5 Å; and $L_E$ is a moiety configured to form a hydrophobic interaction with one or more fifth tubulin residues selected from αT179, βT353, βL248, βL255, βA354, βA316, βA317, and βI318, wherein the distance between at least one atom of the fifth tubulin residues and at least one atom of the $L_E$ moiety is less than 5 Å.

Some embodiments relate to a compound or a pharmaceutically acceptable salt, prodrug, ester thereof, comprising at least three moieties selected from $L_C$, $L_D$, $L_F$, or $L_G$, wherein:

$L_C$ is a moiety configured to hydrogen bond with a tubulin βE200 oxygen atom, wherein the distance between the oxygen atom and the hydrogen bonding atom of the $L_C$ moiety is less than 4 Å;

$L_D$ is a moiety configured to hydrogen bond with a tubulin βV238 oxygen atom, wherein the distance between the tubulin βV238 oxygen atom and the hydrogen bonding atom of the $L_D$ moiety is less than 4 Å;

$L_F$ is a moiety configured to hydrogen bond with a tubulin αT179 oxygen atom, wherein the distance between the tubulin αT179 oxygen atom and the hydrogen bonding atom of $L_F$ is less than 8 Å; and $L_G$ is a moiety configured to hydrogen bond with a tubulin βG237 oxygen atom, wherein the distance between the tubulin βG237 oxygen atom and the hydrogen bonding atom of $L_G$ is less than 8 Å.

Some embodiments relate to a pharmaceutical composition comprising the compound described herein.

Some embodiments relate to a method of treating proliferative disease, disorder, or condition, comprising administering the compound or composition described herein.

Some embodiments relate to a method of treating a cancer, comprising administering the compound or composition described herein.

Some embodiments relate to a method of inhibiting tubulin polymerization, comprising administering the compound or composition described herein.

DETAILED DESCRIPTION OF THE PREFERRED EMBODIMENT

Figure 1:
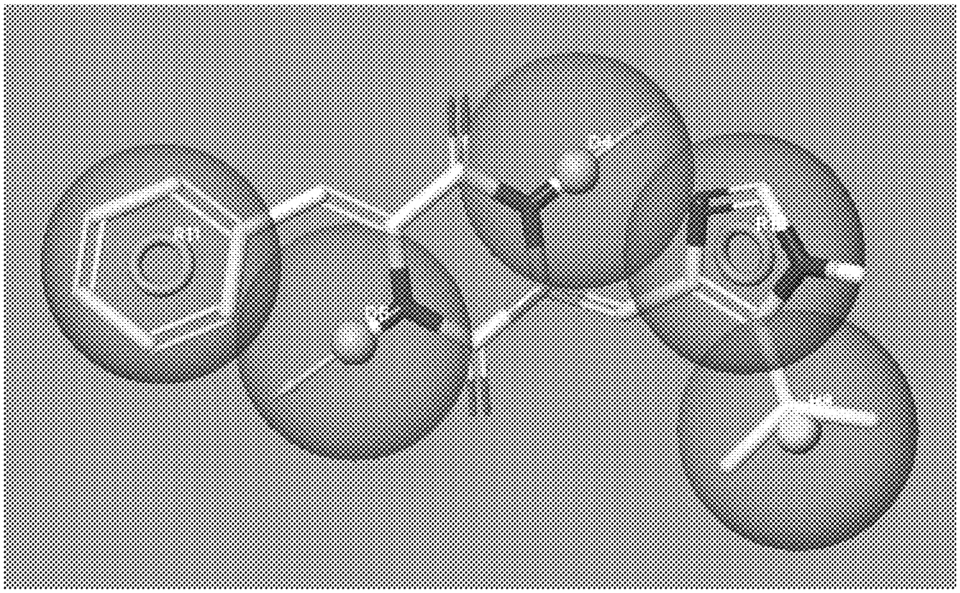
FIG. 1 is a pharmacophore model used for screening the tubulin compounds.

Microtubules are made of αβ-tubulin heterodimers that assemble into protofilaments in a head-to-tail fashion, and the straight and parallel protofilaments interact laterally to form the microtubule hollow cylinder. The compounds disclosed herein can bind to tubulin and interfere with microtubule dynamics. There can be five binding sites for exogenous agents on tubulin, namely the taxane, vinca alkaloid, colchicine, laulimalide, and maytansine domains. The compounds described herein can target one or more of these binding sites. Specifically, the compounds described herein can target the colchicine binding site.

The binding of the compounds described herein may not affect the global conformation of tubulin, nor of the T2R complex. The rmsd for approximately 2000 Ca atoms is less than 0.5 Å for all pairwise comparisons of tubulin-ligand complexes. The major conformational changes may involve two loops near the colchicine binding site, bT7 and αT5. The nomenclature of tubulin secondary structure elements and loops can be found in Lowe J, Li H, Downing K H & Nogales E (2001), *J Mol Biol* 313, 1045-1057, which is incorporated herein by reference for this purpose in its entirety.

Definitions

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group of the compounds may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group of the compounds may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(═O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(═O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(═O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(═O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—$SO_2R$" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—$N(R_A)SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—$OC(═O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—$N(R_A)OC(═O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—$OC(═S)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, a $C_{6-10}$ ryl, 5-10 membered heteroaryl, and 5-10 membered heterocyclyl, as defined herein.

An "N-thiocarbamyl" group refers to an "—$N(R_A)OC(═S)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—$C(═O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—$N(R_A)C(═O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., $-CF_3$), halo($C_1$-$C_6$)alkoxy (e.g., $-OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo ($=O$). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $-CH_2-$, $-CH_2CH_2-$, $-CH_2CH(CH_3)CH_2-$, and the like. Other radical naming conventions clearly indicate that the radical is a di-radical such as "alkylene" or "alkenylene."

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" or "derivative" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety. The pharmaceutically acceptable excipient can be a monosaccharide or monosaccharide derivative.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Compound and Pharmacophore

Microtubules, which are noncovalently linked polymers formed by the α- and β-tubulin heterodimers, are a major component of the cytoskeleton with an important role in a variety of cellular functions, such as cell shape maintenance, intracellular transport, polarity, cell signaling, and mitosis. Compounds possessing tubulin-depolymerizing activity, such as plinabulin were recognized as effective anti-tumor/anti-cancer agents. The effect of tubulin depolymerization can lead to a loss of blood supply and eventual contraction of the tumor. The compounds described herein can bind to tubulin and cause tubulin-depolymerization, and thus can be used to effectively treat cancer and tumor.

Human β-tubulin can have nine isoforms, including TUBB1, TUBB2a, TUBB2b, TUBB3, TUBB4a, TUBB4b, TUBB5 (TUBB), TUBB6, TUBB8. Human β-tubulin TUBB1, TUBB3 and TUBB6 contain a serine residue within close proximity to plinabulin binding, whereas TUBB2A, TUBB2B, TUBB4A, TUBB4B and TUBB5 contain a cysteine residue. The substitution of a serine for a cysteine amino acid residue may provide a difference in binding affinity due to the presence or absence of a sulfide bonding residue. In some embodiments, the human β-tubulin can be a tubulin isoform having a cysteine at the 241 position. In some embodiments, the human β-tubulin can be TUBB2a, TUBB2b, TUBB4a, TUBB4b, or TUBB5 isoforms. In some embodiments, the human β-tubulin has a serine at the 241 position. In some embodiments, the human β-tubulin be TUBB1, TUBB3 or TUBB6 isoform. In some embodiments, the compound described herein can bind stronger to a tubulin isoform (e.g., TUBB1, TUBB3 or TUBB6) wherein the $C_{2-41}$ is substituted by a S241.

In some embodiments, the compounds described herein includes only one of the $L_C$ or the $L_D$ moiety. In some embodiments, the compounds described herein includes both the $L_C$ moiety or the $L_D$ moiety.

In some embodiments, the distance between at least one atom of the first tubulin residues and at least one atom of the aryl or heteroaryl of the $L_A$ moiety is less than 4 Å. In some embodiments, distance between at least one atom of the first tubulin residues and at least one atom of the aryl or heteroaryl of the $L_A$ moiety is less than 3 Å.

In some embodiments, the distance between at least one atom of the second tubulin residues and at least one atom of the aryl or heteroaryl of the $L_B$ moiety is less than 4 Å. In some embodiments, wherein the distance between at least one atom of the second tubulin residues and at least one atom of the aryl or heteroaryl of the $L_B$ moiety is less than 3 Å.

In some embodiments, the distance between at least an atom of the third tubulin residues and at least one atom of the hydrogen bonding atom of the $L_C$ moiety is less than 4 Å. In some embodiments, the distance between at least an atom of the third tubulin residues and at least one atom of the hydrogen bonding atom of the $L_C$ moiety is less than 3 Å.

In some embodiments, the distance between at least an atom of the third tubulin residues and at least one atom of the hydrogen bonding atom of the $L_D$ moiety is less than 4 Å. In some embodiments, the distance between at least an atom of the third tubulin residues and at least one atom of the hydrogen bonding atom of the $L_D$ moiety is less than 3 Å.

In some embodiments, the distance between at least one atom of the fifth tubulin residues and at least one atom of the LE moiety is less than 4 Å. In some embodiments, the distance between at least one atom of the fifth tubulin residues and at least one atom of the LE moiety is less than 3 Å.

In some embodiments, at least one atom of the $L_A$ moiety is positioned within 4 Å from at least one atom of one or more tubulin residues selected from βN167, βQ136, and βE200. In some embodiments, at least one atom of the $L_B$ moiety is positioned within 4 Å from at least one atom of one or more tubulin residues selected from βN258 and βK352. In some embodiments, at least one atom of the $L_C$ moiety is positioned within 4 Å from at least one atom of one or more tubulin residues selected from βI318, βL255, βL242, βM259, βF268, βA316, and 1378. In some embodiments, at least one atom of the $L_D$ moiety is positioned within 4 Å from at least one atom of one or more tubulin residues selected from βI318, βL255, βL242, βM259, βF268, βA316, and βI378. In some embodiments, at least one atom of the $L_E$ moiety is positioned within 4 Å from at least one atom of one or more tubulin residues selected from 3S241, βI376, βT239, and βK352.

In some embodiments, the interaction between the moiety of $L_A$ and the first residues is a Pi bond interaction. In some embodiments, the interaction between the moiety of $L_B$ and the second residues is a Pi bond interaction.

In some embodiments, $L_E$ comprises an optionally substituted —$C_1$-$C_6$alkyl, halogenated $C_1$-$C_6$alkyl, $C_{3-10}$carbocyclyl, 3-10 membered heterocyclyl, —O—$C_1$-$C_6$alkyl, —O-halogenated $C_1$-$C_6$alkyl, —$C_1$-$C_6$alkyl-O—$C_1$-$C_6$alkyl, —C(O)H, —CO—$C_1$-$C_6$alkyl, or cyano.

In some embodiments, the compound described herein can have the structure selected from compounds A-1 to A-51 in Table 1. In some embodiments, the compounds comprises $L_A$, $L_B$, $L_C$, $L_D$, and $L_E$ moieties. In some embodiments, the compounds in Table 1 comprises $L_A$, $L_B$, $L_C$, $L_D$, and $L_E$ moieties.

TABLE 1
| Compound # | Structure | dG Bind Score | CSCORE |
|---|---|---|---|
| A-1 | 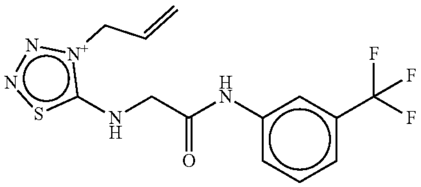 | −80.52 | −85.05 |
| A-2 | 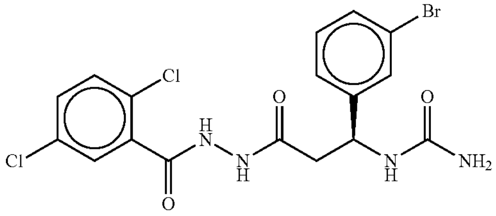 | −75.44 | −81.42 |
| A-3 | 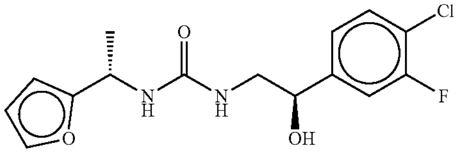 | −74.46 | −80.49 |
| A-4 | 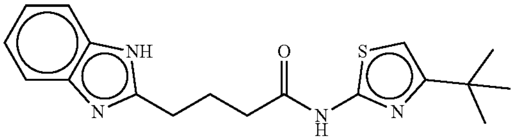 | −75.0 | −79.7 |
| A-5 | 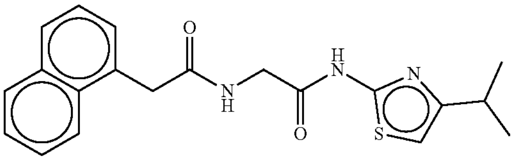 | −74.18 | −79.69 |
| A-6 | 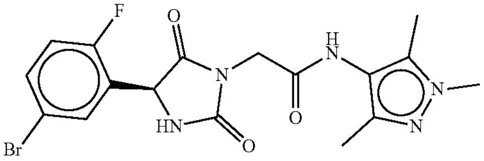 | −74.62 | −79.39 |
| A-7 | 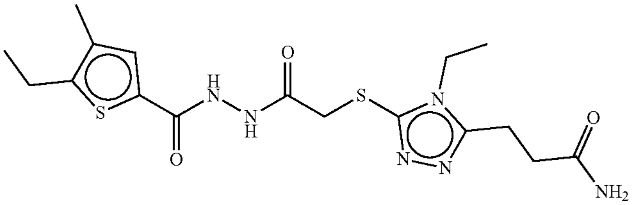 | −72.18 | −77.44 |

TABLE 1-continued
| Compound # | Structure | dG Bind Score | CSCORE |
|---|---|---|---|
| A-8 | 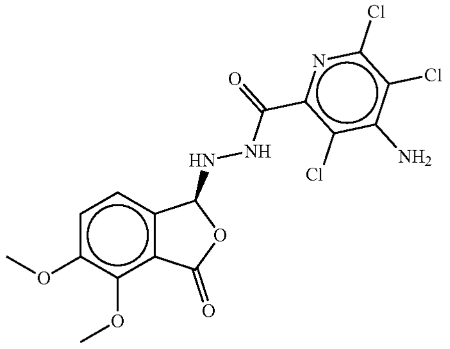 | −71.83 | −76.67 |
| A-9 | 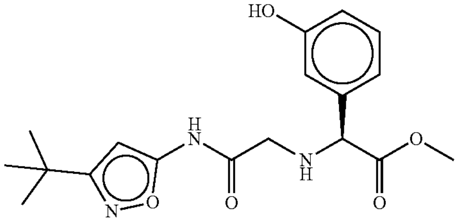 | −70.32 | −75.96 |
| A-10 | 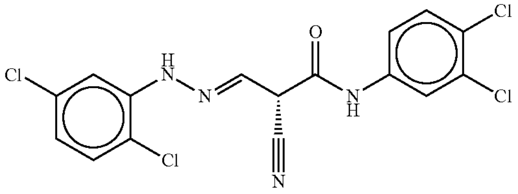 | −68.31 | −74.89 |
| A-11 | 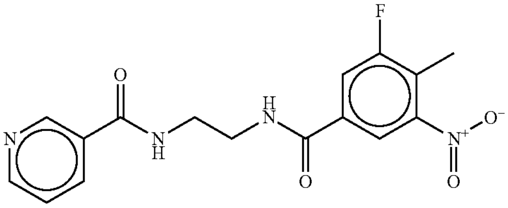 | −68.69 | −74.87 |
| A-12 | 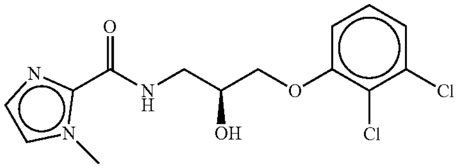 | −69.08 | −74.8 |
| A-13 | 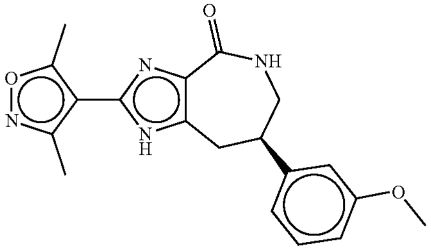 | −67.14 | −74.34 |

TABLE 1-continued
| Compound # | Structure | dG Bind Score | CSCORE |
|---|---|---|---|
| A-14 | 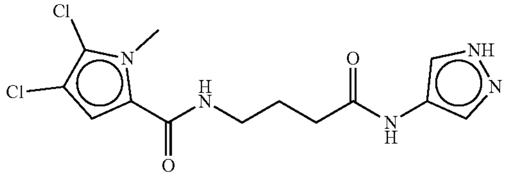 | −67.67 | −73.89 |
| A-15 | 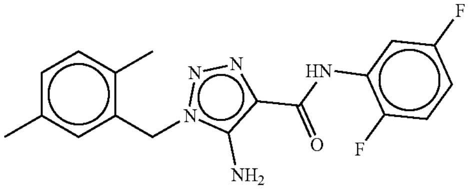 | −67.11 | −73.82 |
| A-16 | 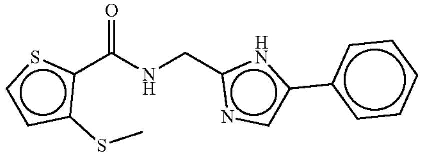 | −67.63 | −73.5 |
| A-17 | 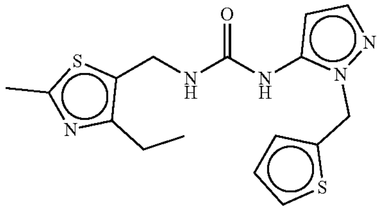 | −67.62 | −73.17 |
| A-18 | 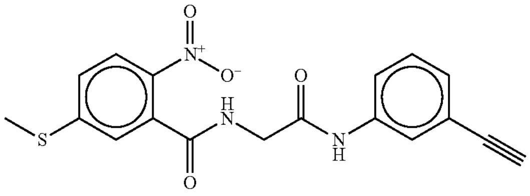 | −68.31 | −72.9 |
| A-19 | 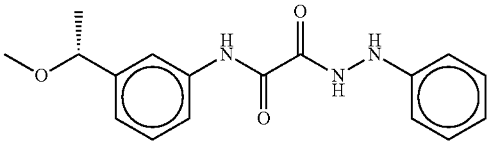 | −66.28 | −72.35 |
| A-20 | 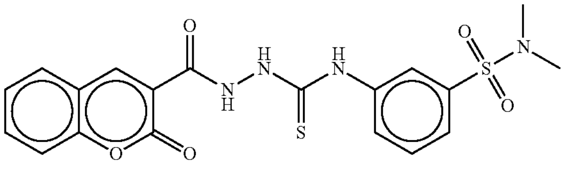 | −66.27 | −72.32 |
| A-21 | 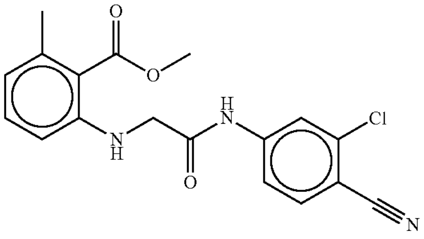 | −67.64 | −72.27 |

TABLE 1-continued
| Compound # | Structure | dG Bind Score | CSCORE |
|---|---|---|---|
| A-22 | 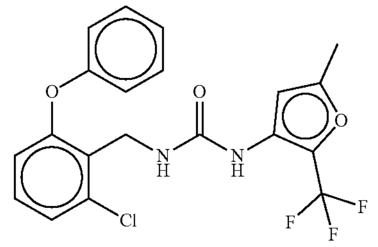 | −65.97 | −72.22 |
| A-23 | 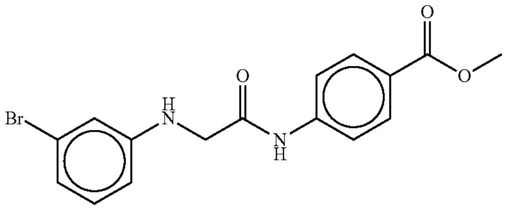 | −67.17 | −72.08 |
| A-24 | 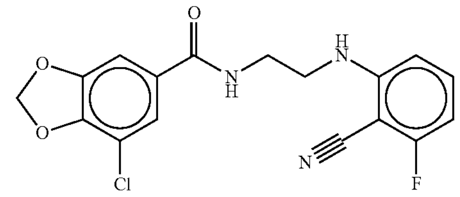 | −65.52 | −71.82 |
| A-25 | 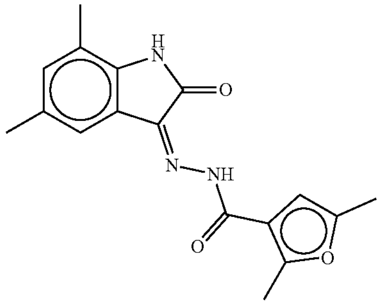 | −65.99 | −71.81 |
| A-26 | 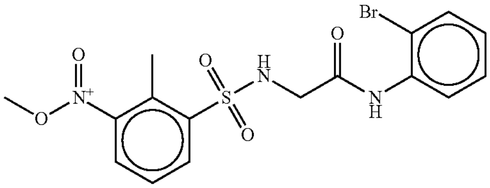 | −65.5 | −71.8 |
| A-27 | 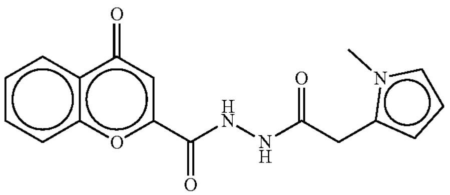 | −66.63 | −71.62 |
| A-28 | 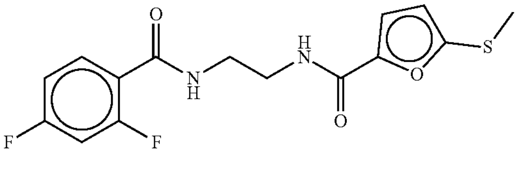 | −66.32 | −71.37 |

TABLE 1-continued
| Compound # | Structure | dG Bind Score | CSCORE |
|---|---|---|---|
| A-29 | 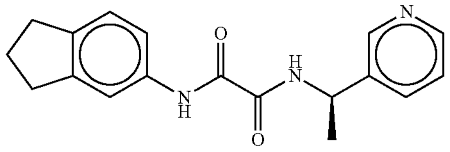 | −65.13 | −70.85 |
| A-30 | 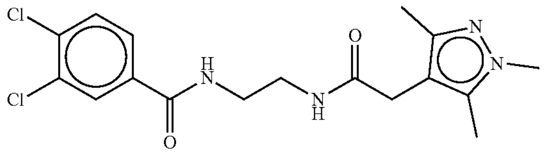 | −65.55 | −70.56 |
| A-31 | 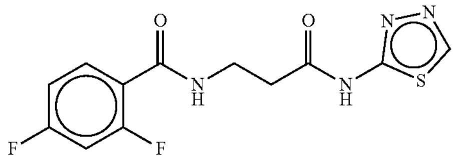 | −64.9 | −70.33 |
| A-32 | 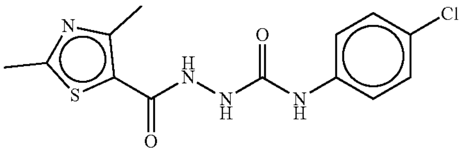 | −65.48 | −70.1 |
| A-33 | 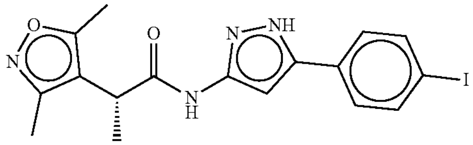 | −63.83 | −69.88 |
| A-34 | 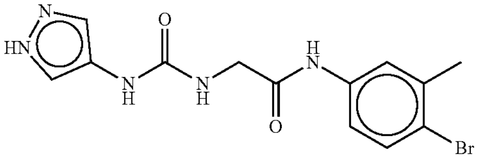 | −64.22 | −69.72 |
| A-35 | 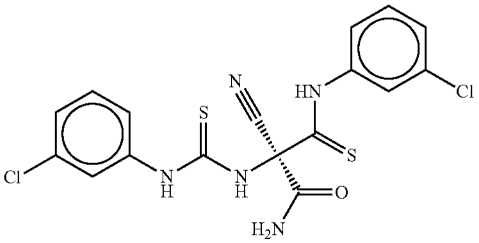 | −64.2 | −69.67 |
| A-36 | 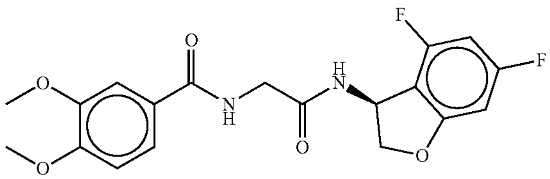 | −62.66 | −69.43 |

TABLE 1-continued
| Compound # | Structure | dG Bind Score | CSCORE |
|---|---|---|---|
| A-37 | 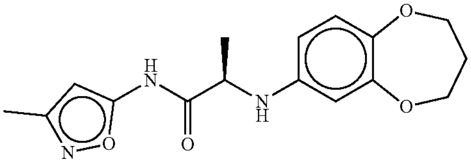 | −63.03 | −69.08 |
| A-38 | 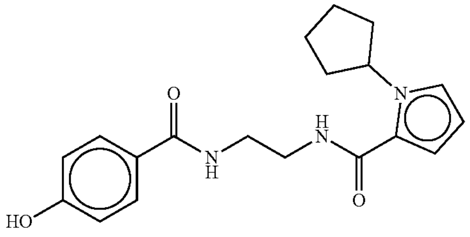 | −63.04 | −69.03 |
| A-39 | 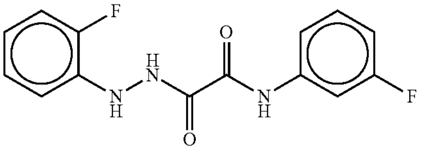 | −63.2 | −68.67 |
| A-40 | 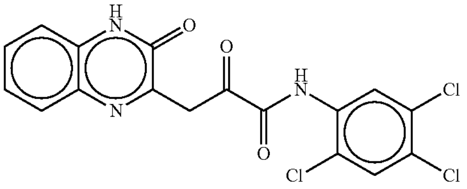 | −63.01 | −68.41 |
| A-41 | 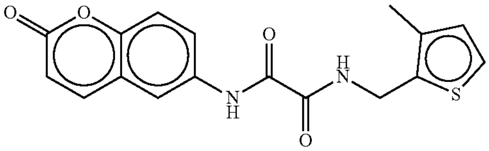 | −63.03 | −67.93 |
| A-42 | 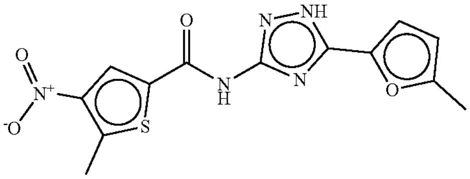 | −63.26 | −67.75 |
| A-43 | 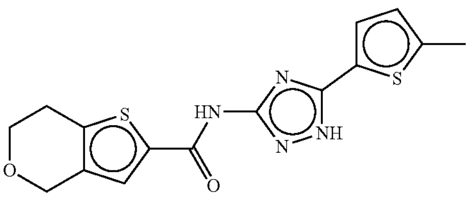 | −61.94 | −66.92 |
| A-44 | 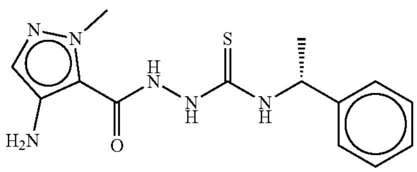 | −62.07 | −66.76 |

TABLE 1-continued

| Compound # | Structure | dG Bind Score | CSCORE |
|---|---|---|---|
| A-45 | 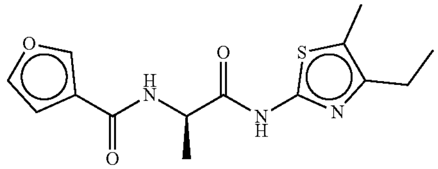 | −62.14 | −66.64 |
| A-46 | 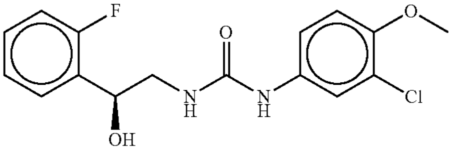 | −61.2 | −66.56 |
| A-47 | 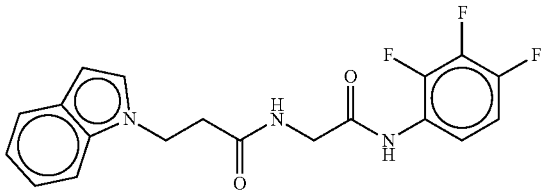 | −61.32 | −66.33 |
| A-48 | 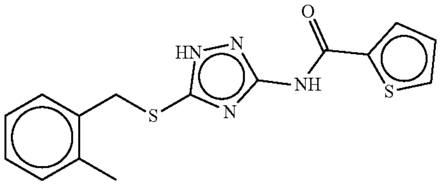 | −60.03 | −66.1 |
| A-49 | 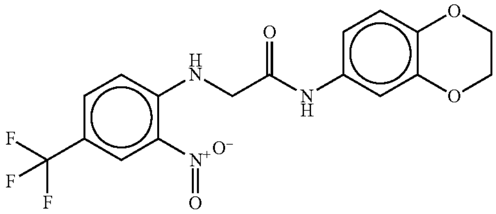 | −60.23 | −65.57 |
| A-50 | 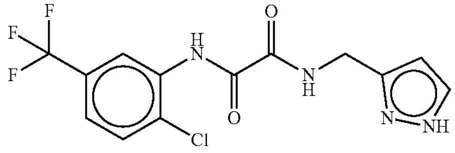 | −60.26 | −65.35 |
| A-51 | 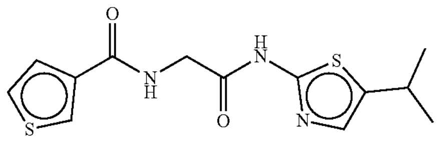 | −60.14 | −64.61 |

In some embodiments, the compound described herein can have a structure selected from compounds B-1 to B-293 in Table 2. In some embodiments, the compounds listed comprises $L_A$, $L_B$, $L_C$, and $L_E$ moieties and does not contain $L_C$ moiety. In some embodiments, the compounds comprises $L_A$, $L_B$, $L_D$, and $L_E$ moieties and does not contain $L_D$ moiety. In some embodiments, the compounds in Table 2 comprises $L_A$, $L_B$, $L_E$ and only one of $L_C$ and $L_E$ moiety.

TABLE 2
| Compound # | Structure | dG Bind Score | CSCORE |
|---|---|---|---|
| B-1 | 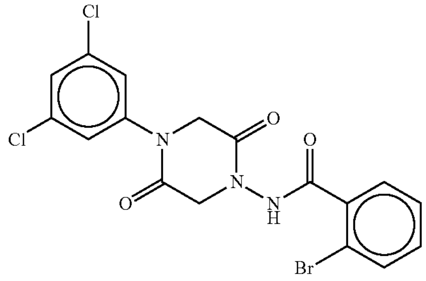 | −84.18 | −90.93 |
| B-2 | 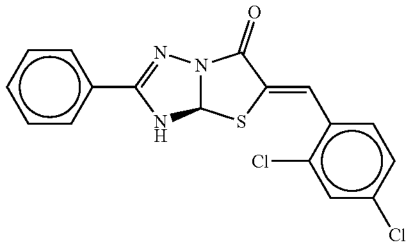 | −81.49 | −88.73 |
| B-3 | 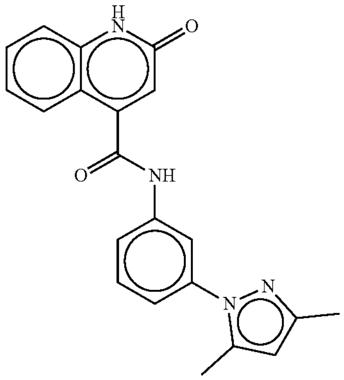 | −82.03 | −88.29 |
| B-4 | 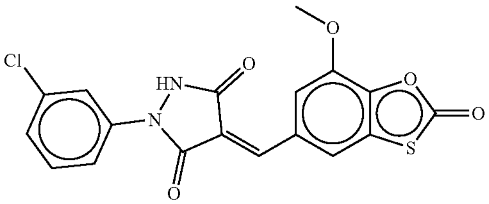 | −80.03 | −87.79 |
| B-5 | 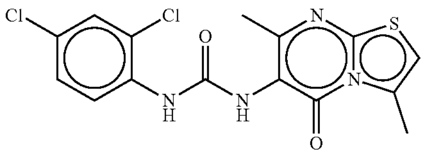 | −80.93 | −87.35 |
| B-6 | 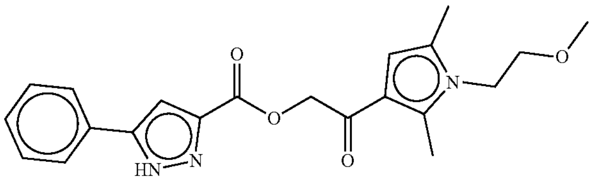 | −79.55 | −86.2 |

TABLE 2-continued
| Compound # | Structure | dG Bind Score | CSCORE |
| --- | --- | --- | --- |
| B-7 | 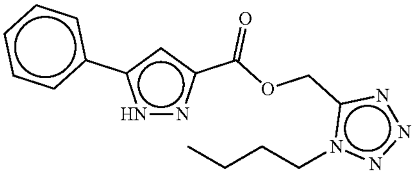 | −79.55 | −85.65 |
| B-8 | 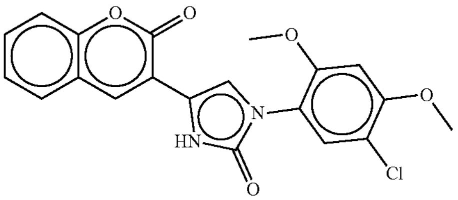 | −76.57 | −83.8 |
| B-9 | 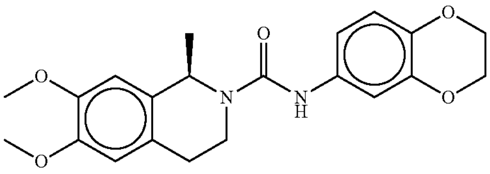 | −77.58 | −73.72 |
| B-10 | 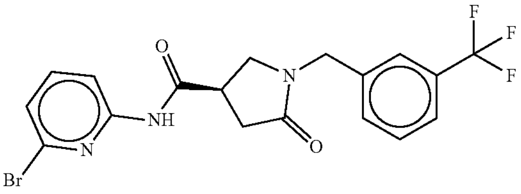 | −75.93 | −83.06 |
| B-11 | 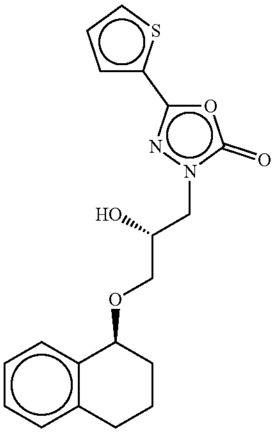 | −75.79 | −82.79 |
| B-12 | 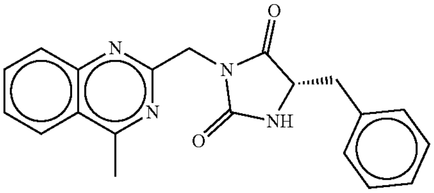 | −74.57 | −82.17 |

TABLE 2-continued
| Compound # | Structure | dG Bind Score | CSCORE |
|---|---|---|---|
| B-13 | 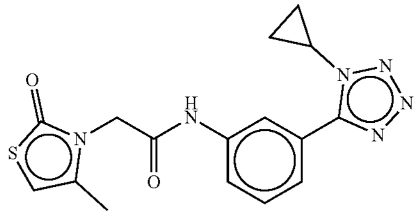 | −75.47 | −82.02 |
| B-14 | 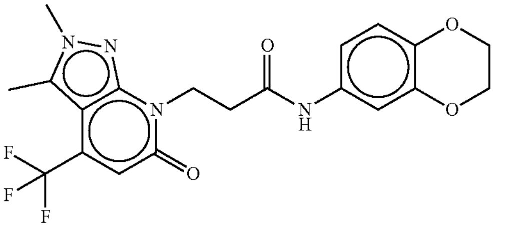 | −75.84 | −82.0 |
| B-15 | 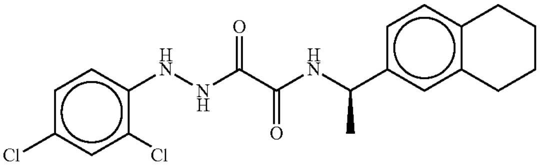 | −75.7 | −81.73 |
| B-16 | 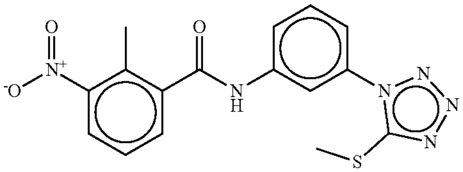 | −75.22 | −81.57 |
| B-17 | 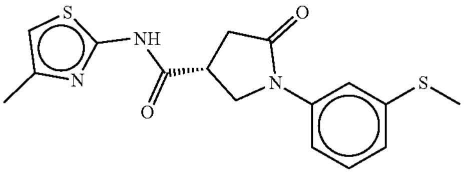 | −75.31 | −81.57 |
| B-18 | 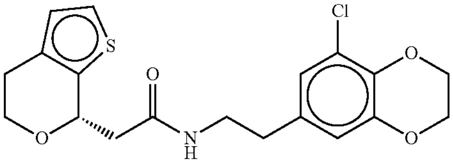 | −75.49 | −81.54 |
| B-19 | 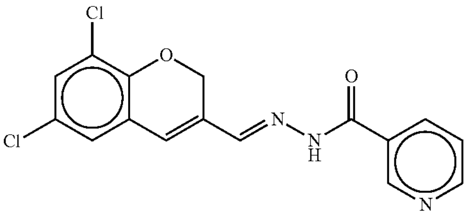 | −74.67 | −81.52 |

TABLE 2-continued
| Compound # | Structure | dG Bind Score | CSCORE |
|---|---|---|---|
| B-20 | 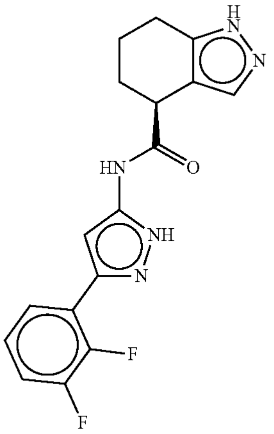 | −74.61 | −81.26 |
| B-21 | 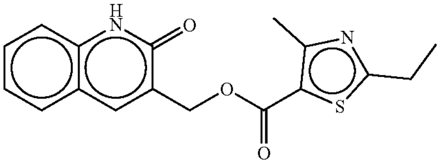 | −74.31 | −81.18 |
| B-22 | 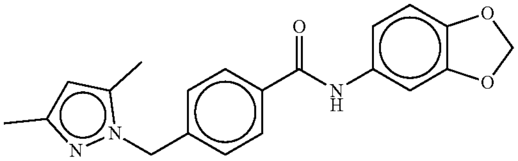 | −74.99 | −81.08 |
| B-23 | 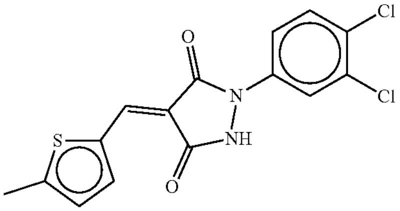 | −73.84 | −80.95 |
| B-24 | 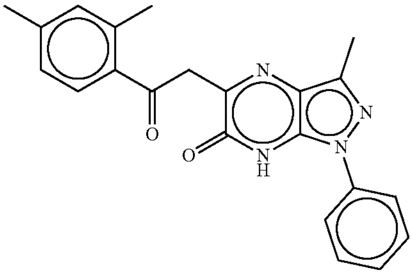 | −74.15 | −80.87 |

TABLE 2-continued
| Compound # | Structure | dG Bind Score | CSCORE |
|---|---|---|---|
| B-25 | 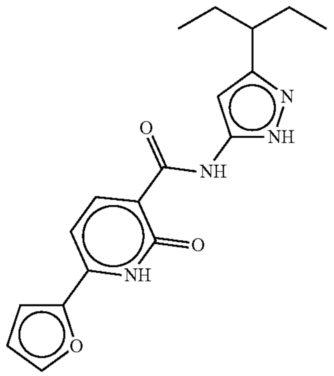 | −74.44 | −80.86 |
| B-26 | 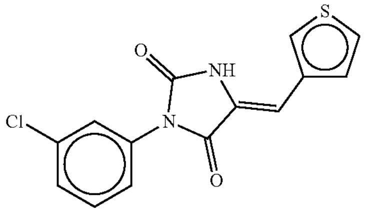 | −73.92 | −80.66 |
| B-27 | 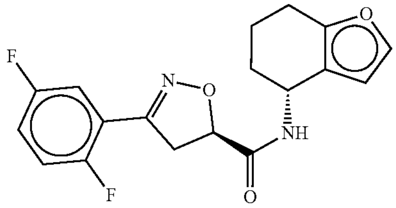 | −73.14 | −80.59 |
| B-28 | 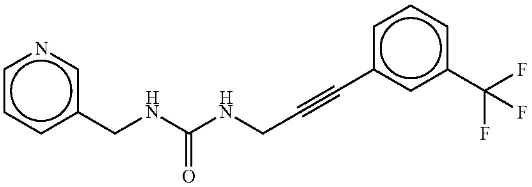 | −73.97 | −80.37 |
| B-29 | 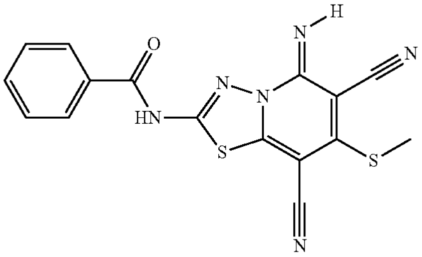 [SMILES: [H]/N=c1\c(C#N)c(SC)c(C#N)c2sc(NC(=O)c3ccccc3)nn12] | −74.05 | −80.21 |
| B-30 | 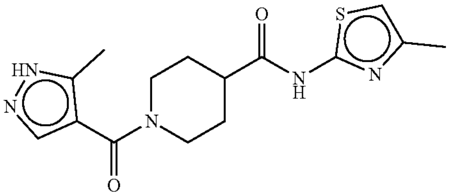 | −73.9 | −80.12 |

TABLE 2-continued
| Compound # | Structure | dG Bind Score | CSCORE |
|---|---|---|---|
| B-31 | 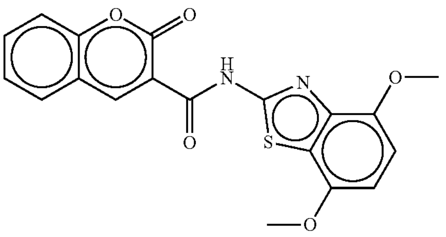 | −73.37 | −79.95 |
| B-32 | 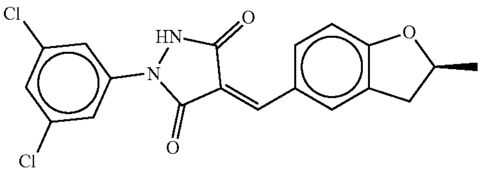 | −72.03 | −79.82 |
| B-33 | 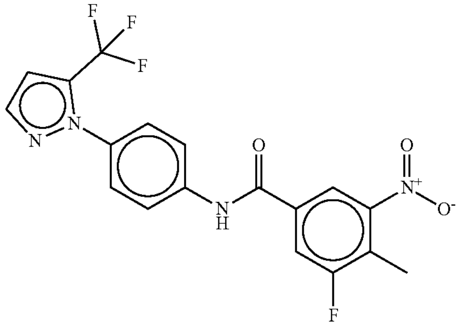 | −73.74 | −79.75 |
| B-34 | 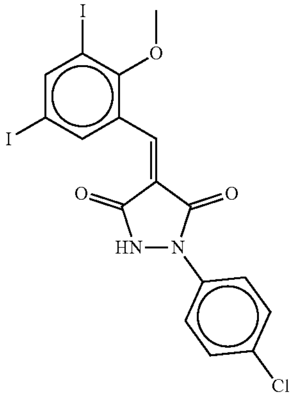 | −73.56 | −79.7 |
| B-35 | 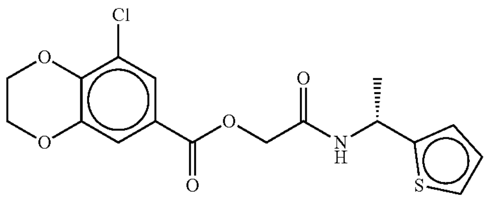 | −73.35 | −79.5 |
| B-36 | 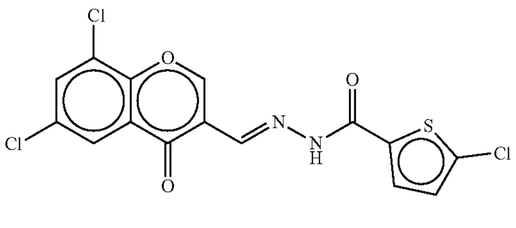 | −73.02 | −79.27 |

TABLE 2-continued
| Compound # | Structure | dG Bind Score | CSCORE |
|---|---|---|---|
| B-37 | 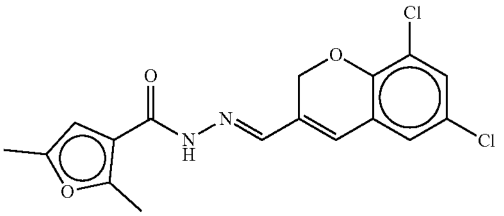 | −73.04 | −79.21 |
| B-38 | 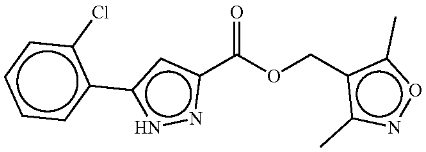 | −72.52 | −79.11 |
| B-39 | 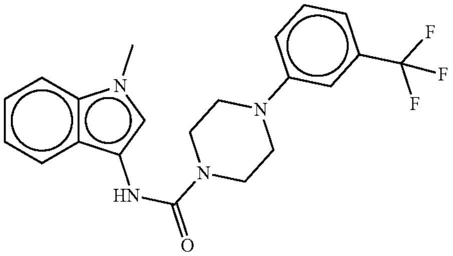 | −73.02 | −79.0 |
| B-40 | 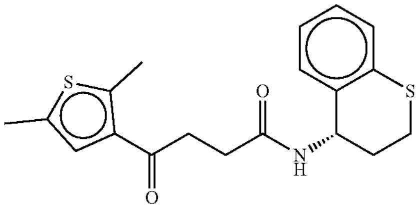 | −72.19 | −78.4 |
| B-41 | 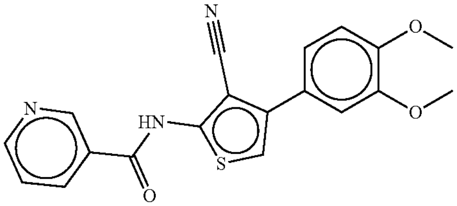 | −71.84 | −78.23 |
| B-42 | 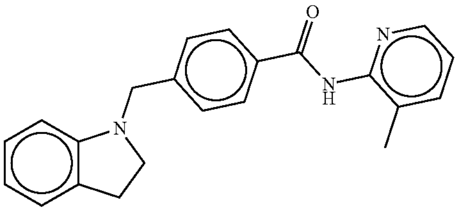 | −71.71 | −77.75 |
| B-43 | 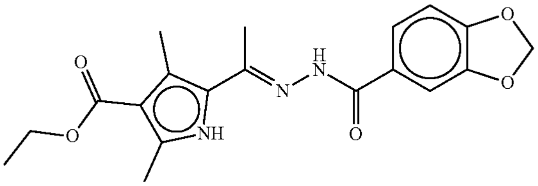 | −71.71 | −77.75 |

TABLE 2-continued
| Compound # | Structure | dG Bind Score | CSCORE |
|---|---|---|---|
| B-44 | 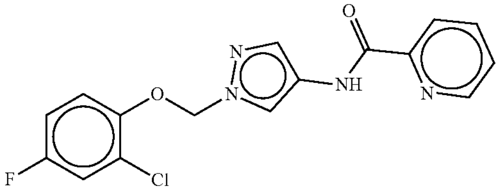 | −71.21 | −77.49 |
| B-45 | 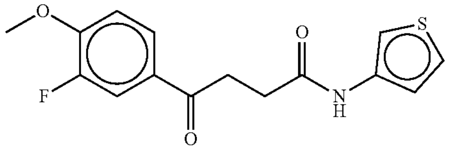 | −70.85 | −77.31 |
| B-46 | 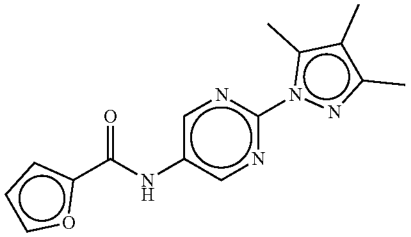 | −71.11 | −77.26 |
| B-47 | 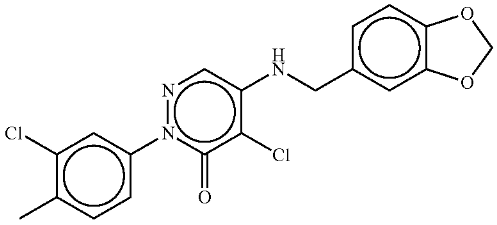 | −71.21 | −77.24 |
| B-48 | 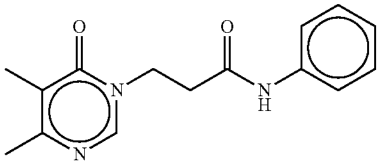 | −70.8 | −77.17 |
| B-49 | 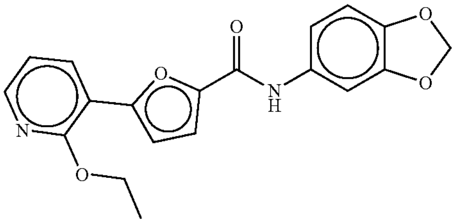 | −70.82 | −77.13 |
| B-50 | 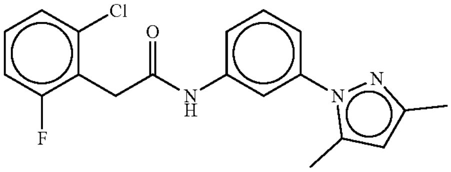 | −70.99 | −77.09 |

TABLE 2-continued
| Compound # | Structure | dG Bind Score | CSCORE |
|---|---|---|---|
| B-51 | 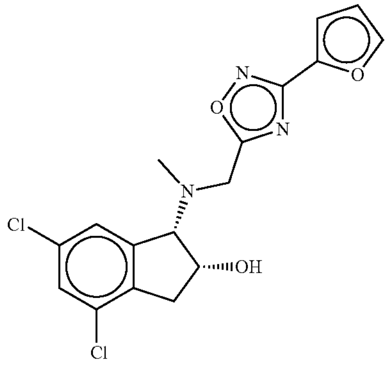 | −70.7 | −76.99 |
| B-52 | 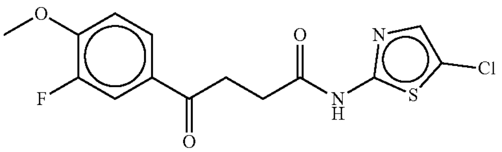 | −70.94 | −76.92 |
| B-53 | 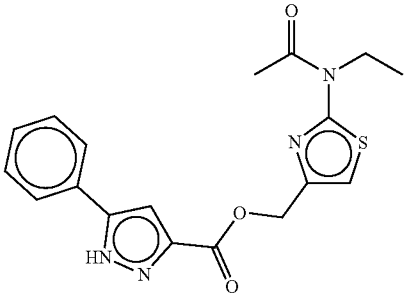 | −70.36 | −76.74 |
| B-54 | 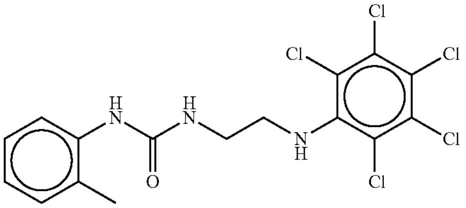 | −70.43 | −76.72 |
| B-55 | 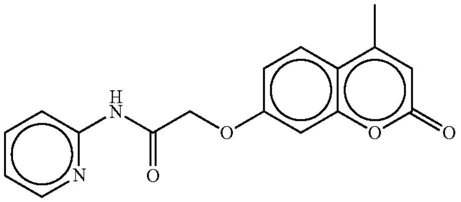 | −70.13 | −76.66 |
| B-56 | 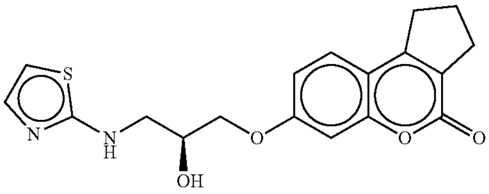 | −70.25 | −76.64 |

TABLE 2-continued
| Compound # | Structure | dG Bind Score | CSCORE |
|---|---|---|---|
| B-57 | 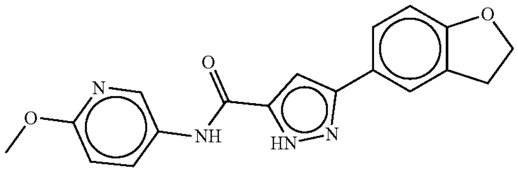 | −69.93 | −76.6 |
| B-58 | 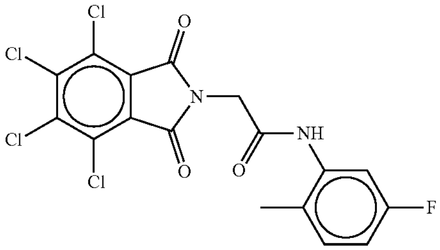 | −70.6 | −76.58 |
| B-59 | 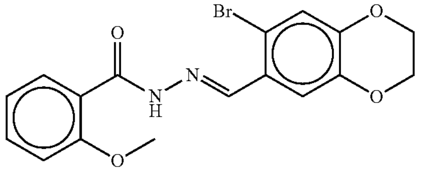 | −70.55 | 76.57 |
| B-60 | 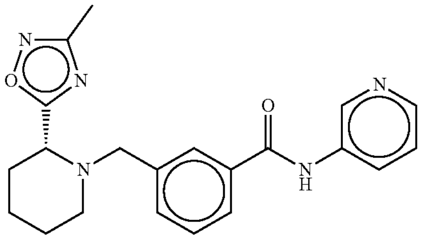 | −70.14 | −76.49 |
| B-61 | 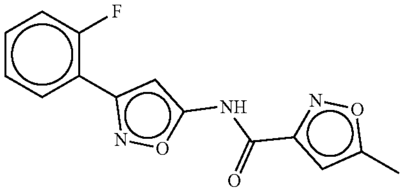 | −70.1 | −76.47 |
| B-62 | 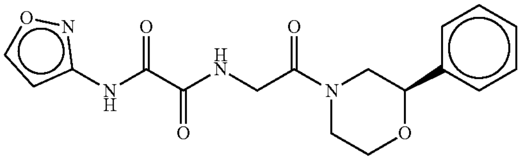 | −70.23 | −76.29 |
| B-63 | 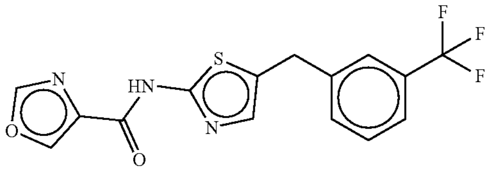 | −69.97 | −76.07 |

TABLE 2-continued
| Compound # | Structure | dG Bind Score | CSCORE |
|---|---|---|---|
| B-64 | 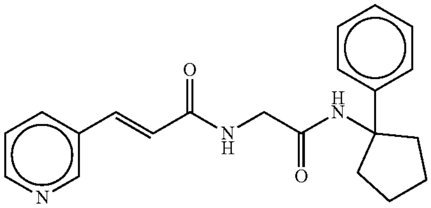 | −69.54 | −76.03 |
| B-65 | 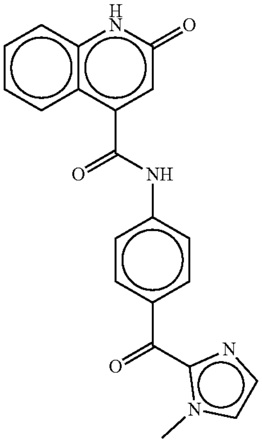 | −69.22 | −75.97 |
| B-66 | 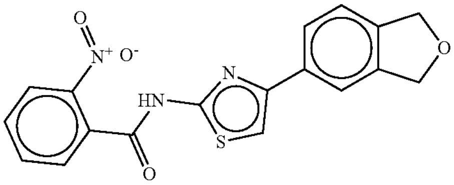 | −69.67 | −75.96 |
| B-67 | 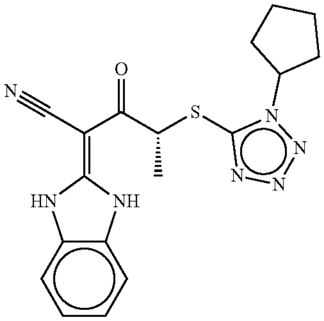 | −69.62 | −75.89 |
| B-68 | 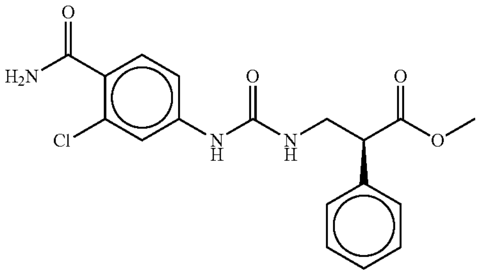 | −69.74 | −75.82 |

TABLE 2-continued
| Compound # | Structure | dG Bind Score | CSCORE |
|---|---|---|---|
| B-69 | 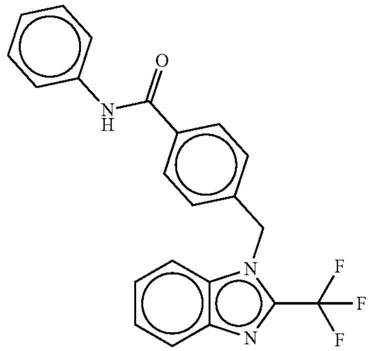 | −68.96 | −75.75 |
| B-70 | 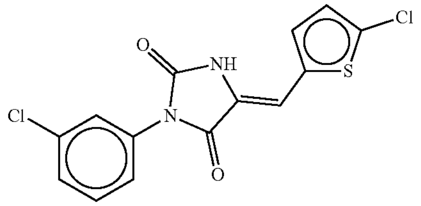 | −69.1 | −75.73 |
| B-71 | 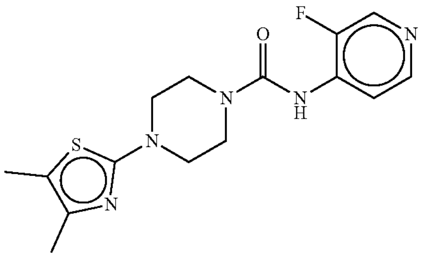 | −69.4 | −75.57 |
| B-72 | 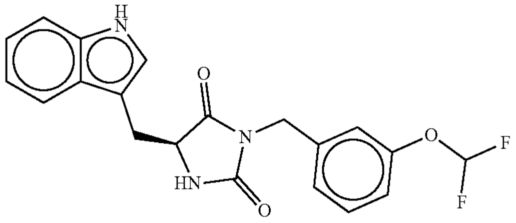 | −68.01 | −75.54 |
| B-73 | 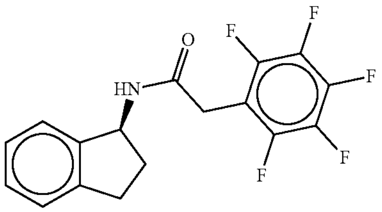 | −69.08 | −75.5 |
| B-74 | 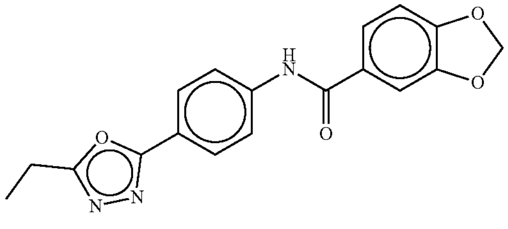 | −68.75 | −75.46 |

TABLE 2-continued
| Compound # | Structure | dG Bind Score | CSCORE |
|---|---|---|---|
| B-75 | 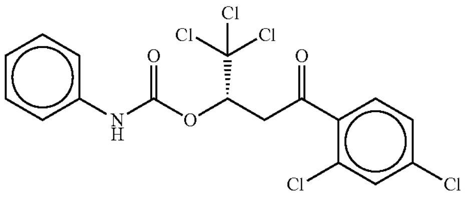 | −68.88 | −75.38 |
| B-76 | 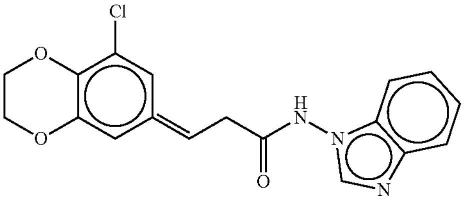 | −68.66 | −75.31 |
| B-77 | 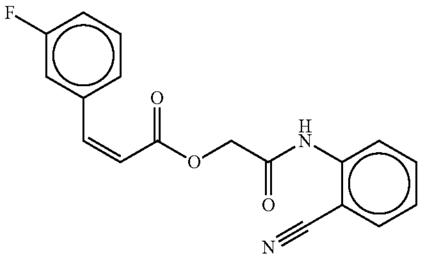 | −69.18 | −75.3 |
| B-78 | 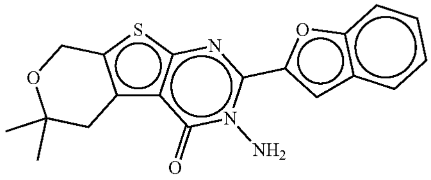 | −68.58 | −75.05 |
| B-79 | 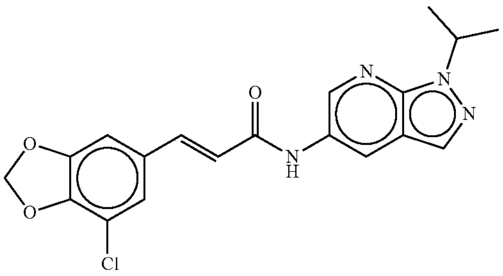 | −68.87 | −74.94 |
| B-80 | 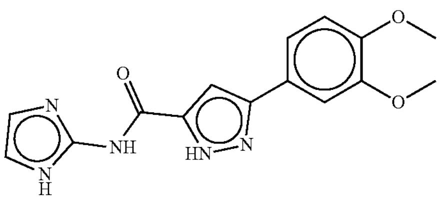 | −68.59 | −74.91 |
| B-81 | 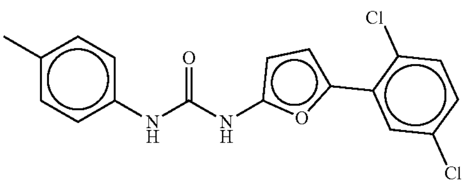 | −68.11 | −74.88 |

TABLE 2-continued
| Compound # | Structure | dG Bind Score | CSCORE |
|---|---|---|---|
| B-82 | 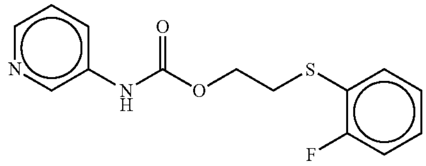 | −68.7 | −74.81 |
| B-83 | 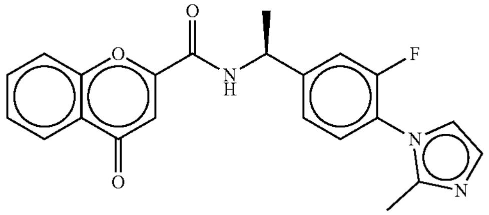 | −68.82 | −74.78 |
| B-84 | 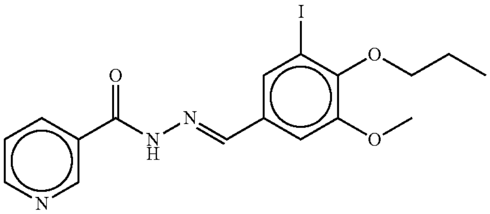 | −68.5 | −74.74 |
| B-35 | 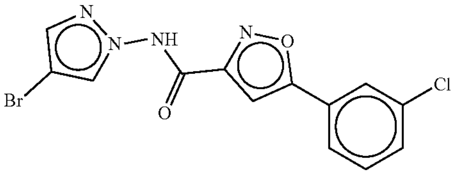 | −68.54 | −74.72 |
| B-86 | 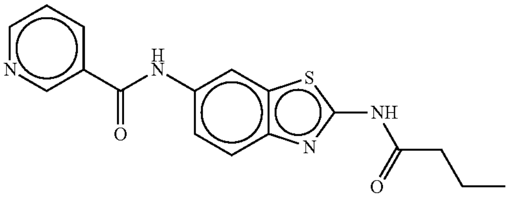 | −67.73 | −74.61 |
| B-87 | 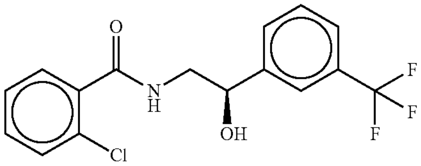 | −67.76 | −74.6 |
| B-88 | 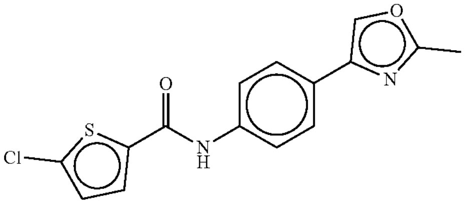 | −68.01 | −74.56 |

TABLE 2-continued
| Compound # | Structure | dG Bind Score | CSCORE |
|---|---|---|---|
| B-89 | 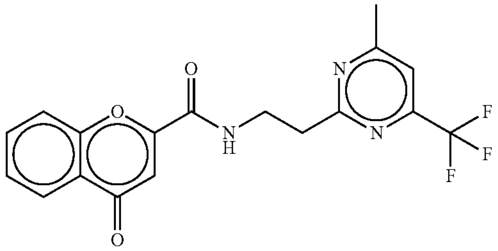 | −68.18 | −74.56 |
| B-90 | 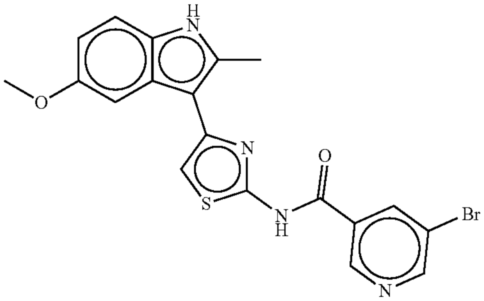 | −67.43 | −74.55 |
| B-91 | 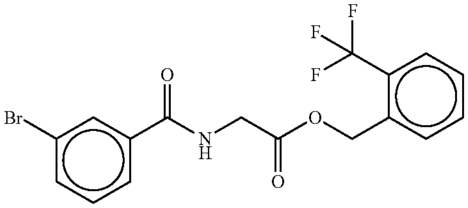 | −68.4 | −74.54 |
| B-92 | 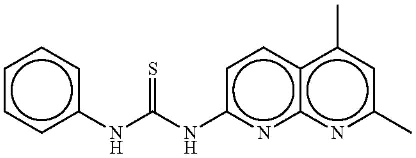 | −67.55 | −74.5 |
| B-93 | 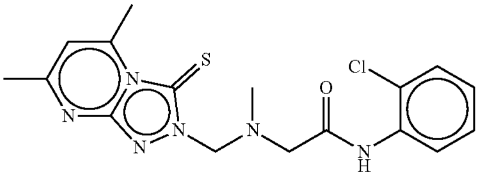 | −68.3 | −74.47 |
| B-94 | 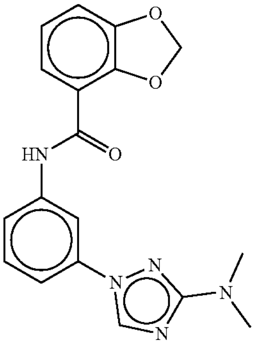 | −68.17 | −74.42 |

TABLE 2-continued
| Compound # | Structure | dG Bind Score | CSCORE |
|---|---|---|---|
| B-95 | 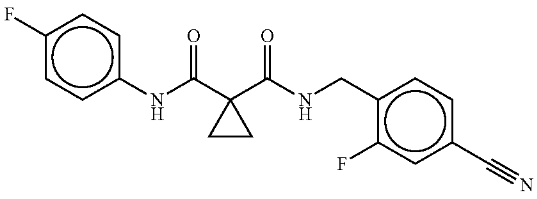 | −68.27 | −74.41 |
| B-96 | 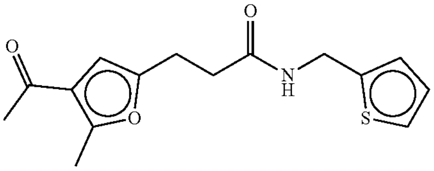 | −68.31 | −74.35 |
| B-97 | 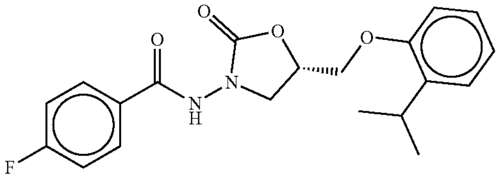 | −67.55 | −74.34 |
| B-98 | 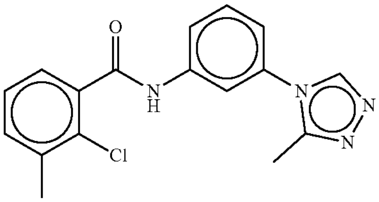 | −67.59 | −74.31 |
| B-99 | 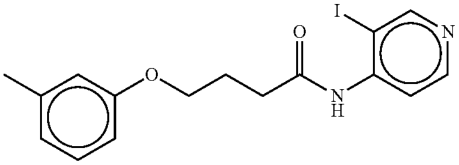 | −67.8 | −74.03 |
| B-100 | 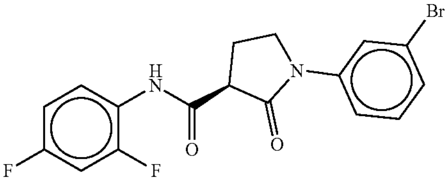 | −66.96 | −74.0 |
| B-101 | 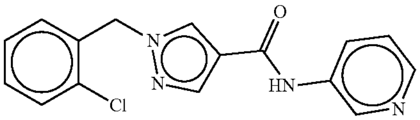 | −67.46 | −73.99 |
| B-102 | 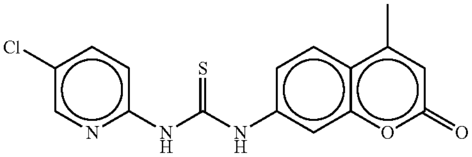 | −67.75 | −73.96 |

TABLE 2-continued
| Compound # | Structure | dG Bind Score | CSCORE |
|---|---|---|---|
| B-103 | 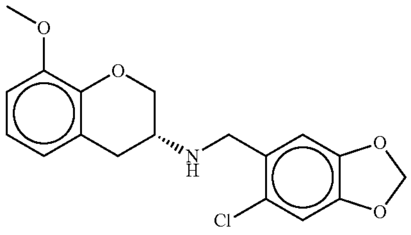 | −67.77 | −73.95 |
| B-104 | 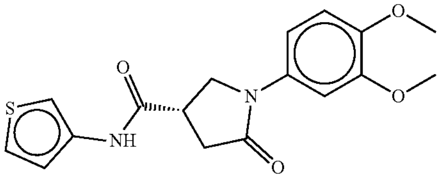 | −67.32 | −73.89 |
| B-105 | 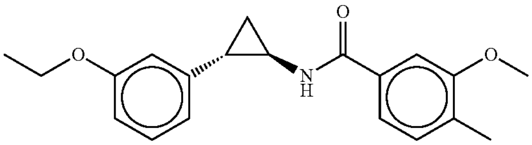 | −67.21 | −73.8 |
| B-106 | 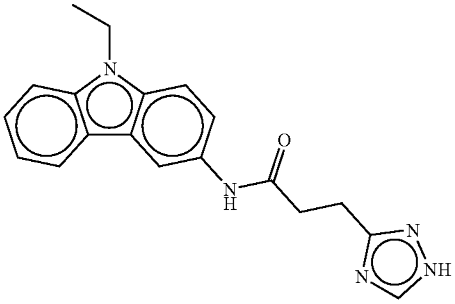 | −67.18 | −73.76 |
| B-107 | 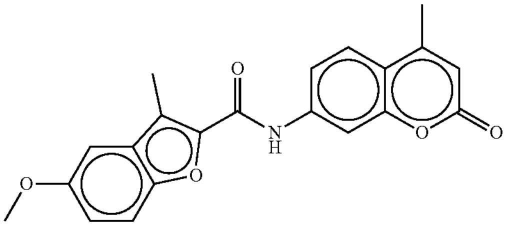 | −67.74 | −73.74 |
| B-108 | 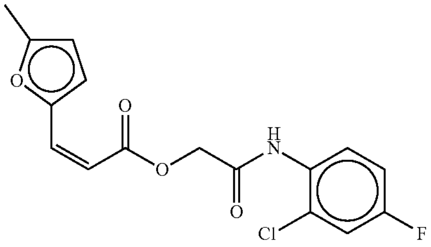 | −67.47 | −73.74 |

TABLE 2-continued
| Compound # | Structure | dG Bind Score | CSCORE |
|---|---|---|---|
| B-109 | 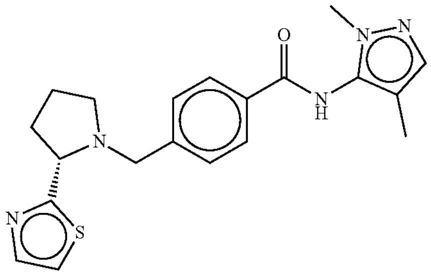 | −67.02 | −73.7 |
| B-110 | 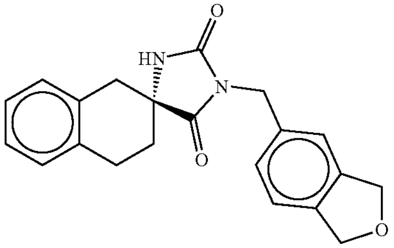 | −67.4 | −73.64 |
| B-111 | 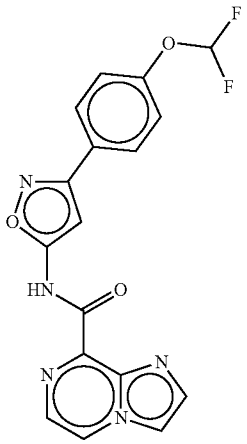 | −67.32 | −73.61 |
| B-112 | 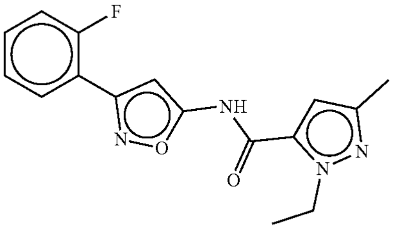 | −67.33 | −73.59 |
| B-113 | 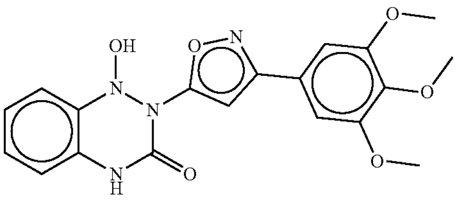 | −66.61 | −73.45 |

TABLE 2-continued
| Compound # | Structure | dG Bind Score | CSCORE |
|---|---|---|---|
| B-114 | 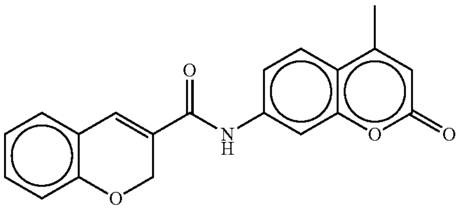 | −67.23 | −73.37 |
| B-115 | 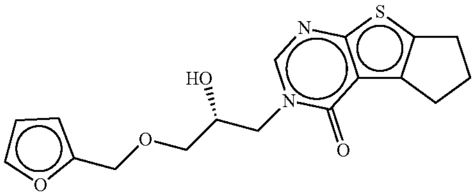 | −66.85 | −73.29 |
| B-116 | 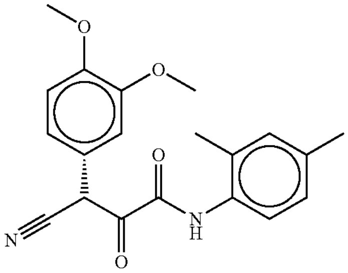 | −66.98 | −73.26 |
| B-117 | 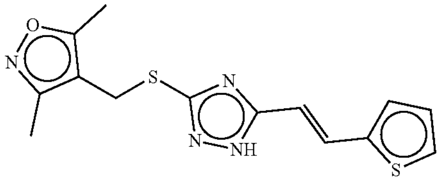 | −67.25 | −73.21 |
| B-118 | 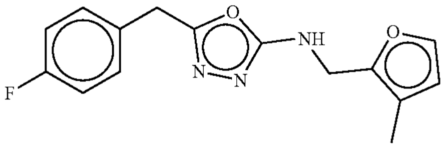 | −66.83 | −73.2 |
| B-119 | 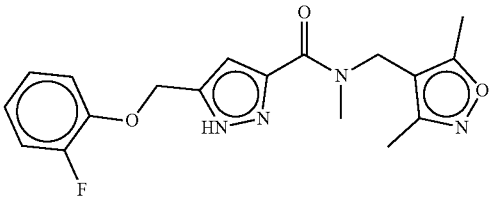 | −66.85 | −73.14 |
| B-120 | 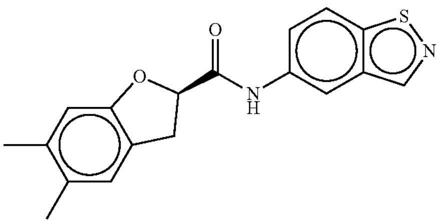 | −67.08 | −73.13 |

TABLE 2-continued
| Compound # | Structure | dG Bind Score | CSCORE |
|---|---|---|---|
| B-121 | 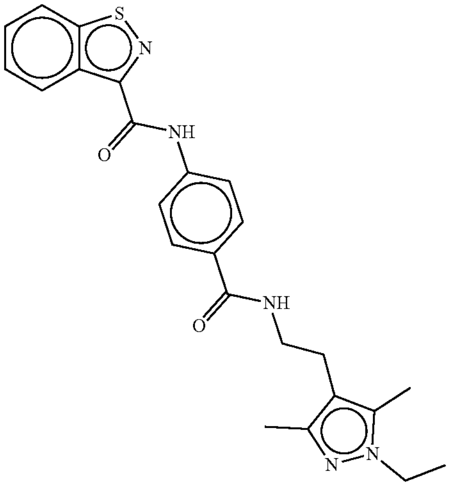 | −66.78 | −73.02 |
| B-122 | 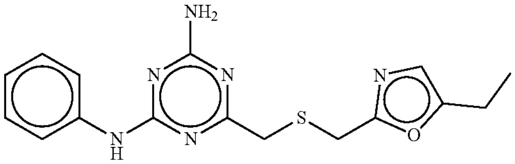 | −66.68 | −72.96 |
| B-123 | 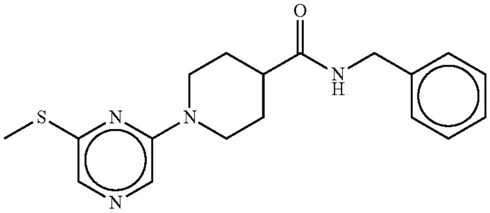 | −66.61 | −72.88 |
| B–124 | 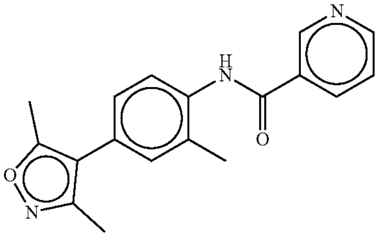 | −66.45 | −72.76 |
| B-125 | 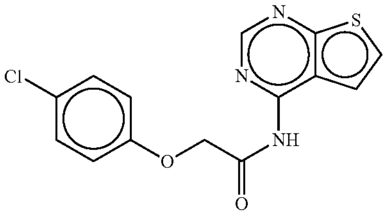 | −66.76 | −72.767 |
| B-126 | 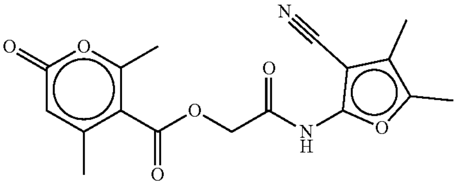 | −66.45 | −72.74 |

TABLE 2-continued
| Compound # | Structure | dG Bind Score | CSCORE |
|---|---|---|---|
| B-127 | 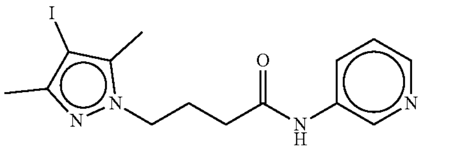 | −66.38 | −72.74 |
| B-128 | 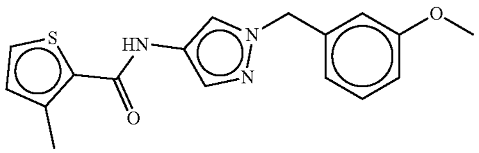 | −66.64 | −72.74 |
| B-129 | 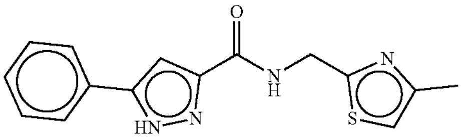 | −66.26 | −72.73 |
| B-130 | 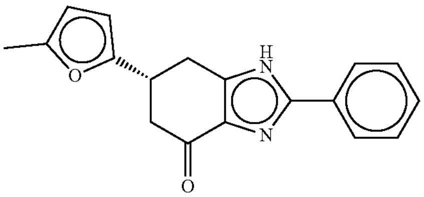 | −65.28 | −72.66 |
| B-131 | 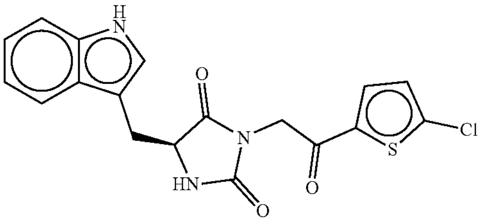 | −65.58 | −72.62 |
| B-132 | 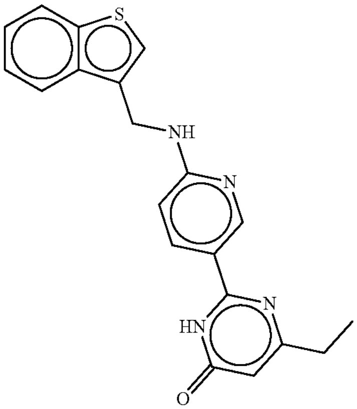 | −66.06 | −72.61 |
| B-133 | 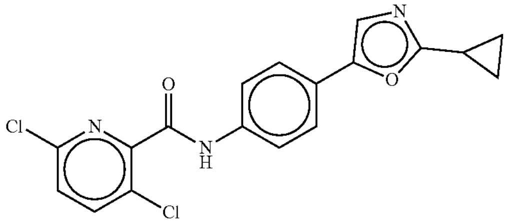 | −65.64 | −72.57 |

TABLE 2-continued
| Compound # | Structure | dG Bind Score | CSCORE |
|---|---|---|---|
| B-134 | 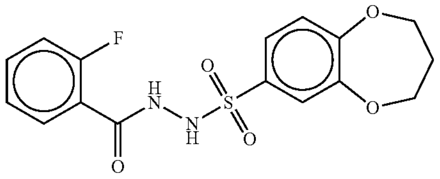 | −66.18 | −72.53 |
| B-135 | 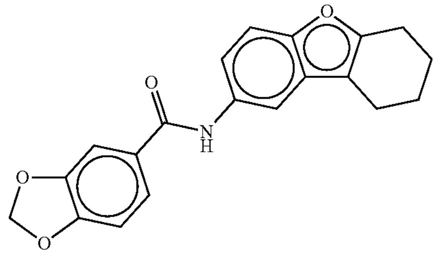 | −66.05 | −72.49 |
| B-136 | 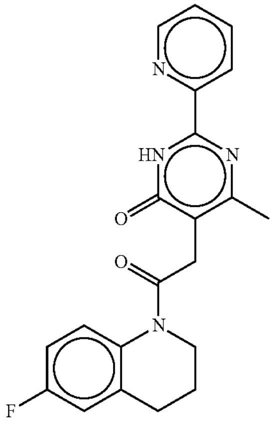 | −65.15 | −72.45 |
| B-137 | 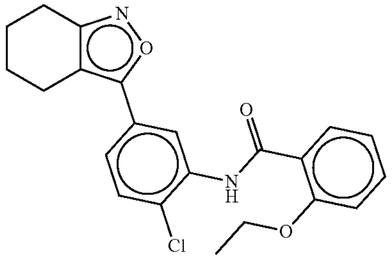 | −65.91 | −72.41 |
| B-138 | 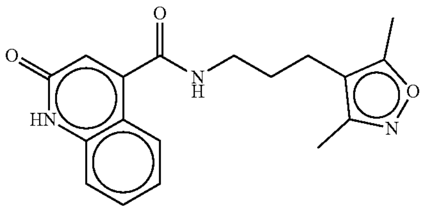 | −66.0 | −72.35 |

TABLE 2-continued
| Compound # | Structure | dG Bind Score | CSCORE |
|---|---|---|---|
| B-139 | 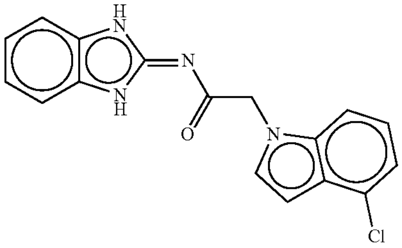 | −66.23 | −72.27 |
| B-140 | 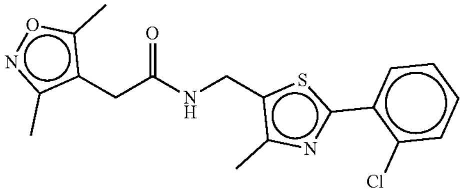 | −66.18 | −72.23 |
| B-141 | 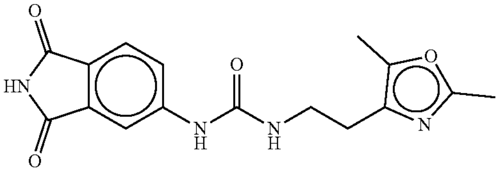 | −66.23 | −72.21 |
| B-142 | 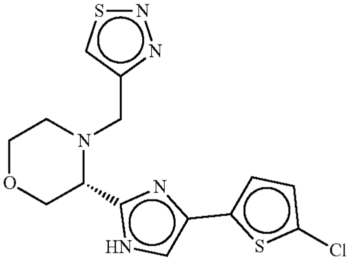 | −65.91 | −72.16 |
| B-143 | 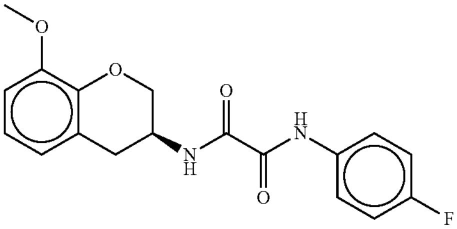 | −65.36 | −72.14 |
| B-144 | 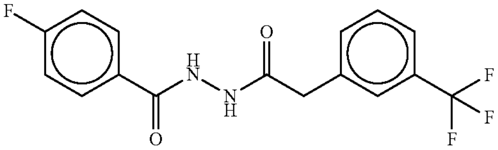 | −65.97 | −72.12 |

TABLE 2-continued
| Compound # | Structure | dG Bind Score | CSCORE |
|---|---|---|---|
| B-145 | 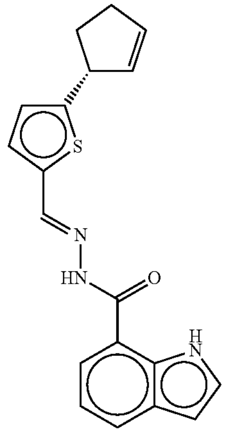 | −65.9 | −72.1 |
| B-146 | 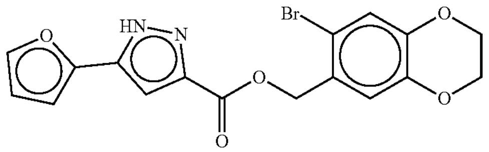 | −65.42 | −72.02 |
| B-147 | 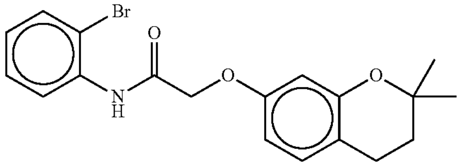 | −64.96 | −71.91 |
| B-148 | 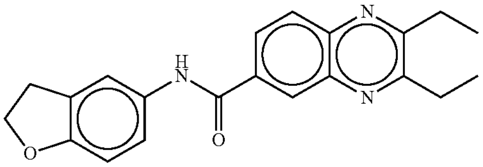 | −65.75 | −71.79 |
| B-149 | 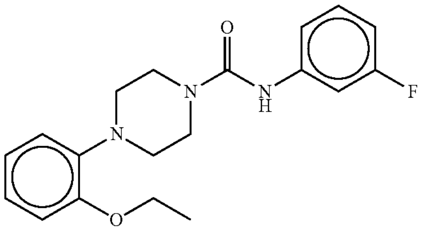 | −65.54 | −71.78 |
| B-150 | 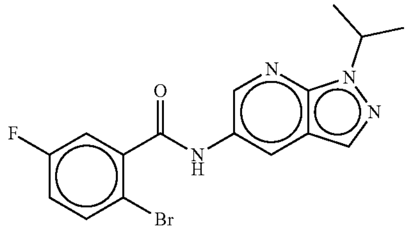 | −65.31 | −71.77 |

TABLE 2-continued
| Compound # | Structure | dG Bind Score | CSCORE |
| --- | --- | --- | --- |
| B-151 | 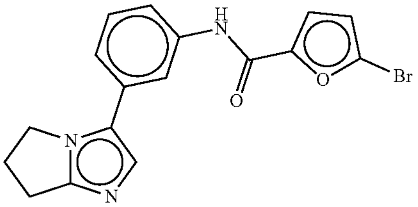 | −65.22 | −71.73 |
| B-152 | 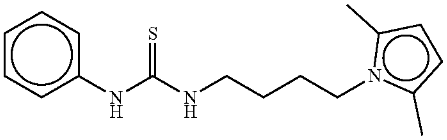 | −65.22 | −71.72 |
| B-153 | 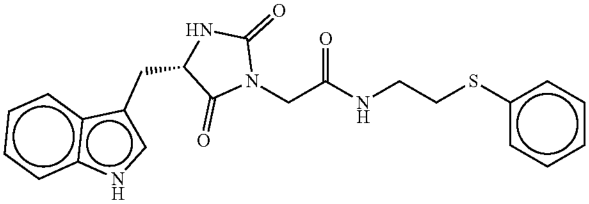 | −64.24 | −71.7 |
| B-154 | 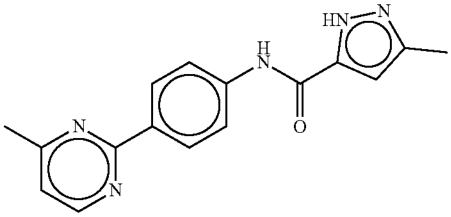 | −65.43 | −71.69 |
| B-155 | 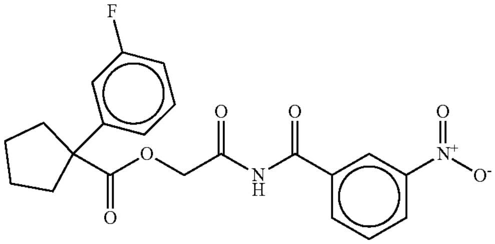 | −65.57 | −71.66 |
| B-156 | 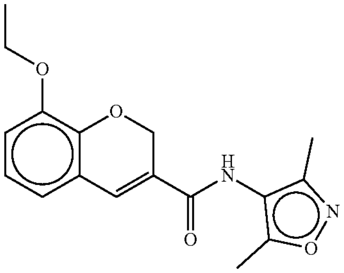 | −65.11 | −71.64 |
| B-157 | 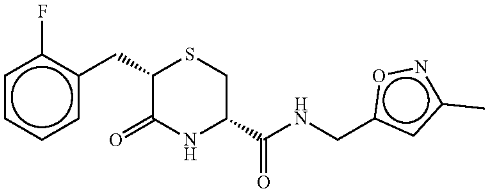 | −65.21 | −71.56 |

TABLE 2-continued
| Compound # | Structure | dG Bind Score | CSCORE |
|---|---|---|---|
| B-158 | 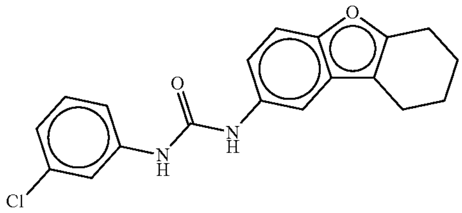 | −65.0 | −71.54 |
| B-159 | 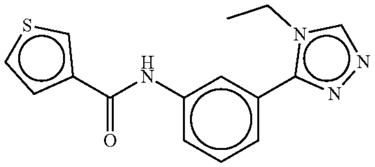 | −65.25 | −71.52 |
| B-160 | 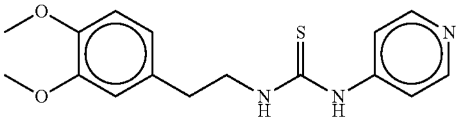 | −64.92 | −71.47 |
| B-161 | 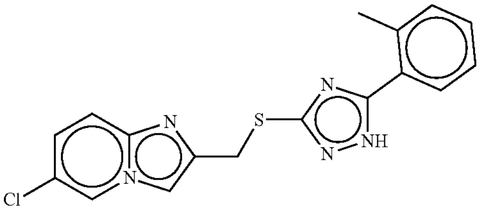 | −64.3 | −71.4 |
| B-162 | 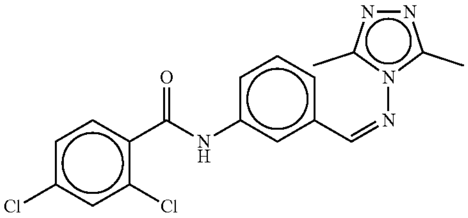 | −64.76 | −71.29 |
| B-163 | 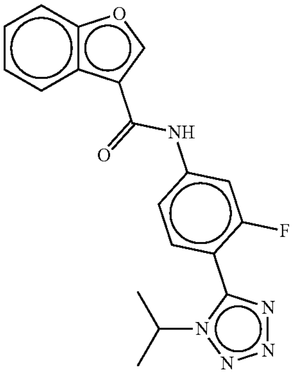 | −64.75 | −71.28 |
| B-164 | 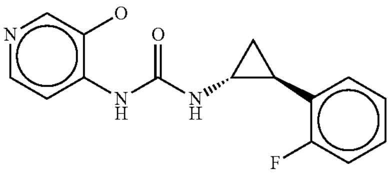 | −64.9 | −71.27 |

TABLE 2-continued
| Compound # | Structure | dG Bind Score | CSCORE |
|---|---|---|---|
| B-165 | 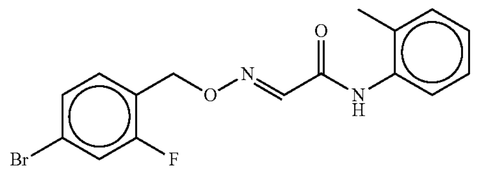 | −64.67 | −71.27 |
| B-166 | 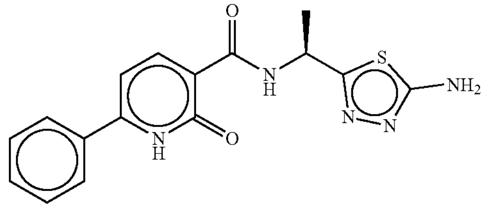 | −63.85 | −71.24 |
| B-167 | 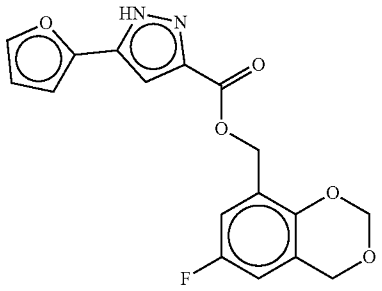 | −64.51 | −71.23 |
| B-168 | 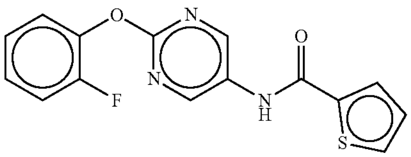 | −64.9 | −71.22 |
| B-169 | 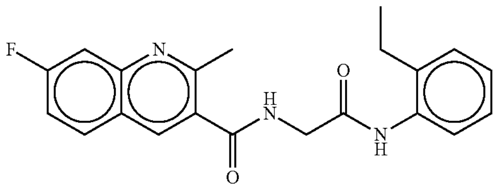 | −64.94 | −71.22 |
| B-170 | 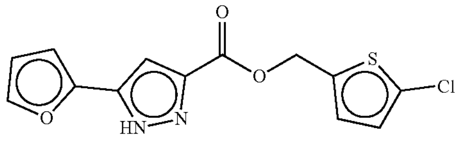 | −64.95 | −71.21 |
| B-171 | 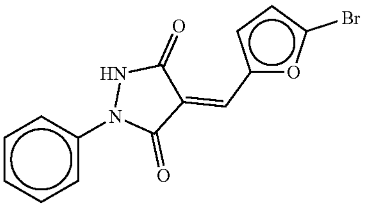 | −64.08 | −71.17 |

TABLE 2-continued
| Compound # | Structure | dG Bind Score | CSCORE |
|---|---|---|---|
| B-172 | 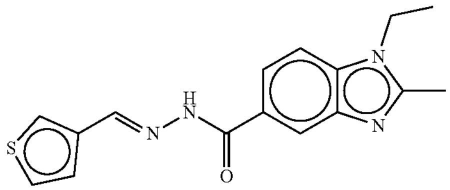 | −64.91 | −71.12 |
| B-173 | 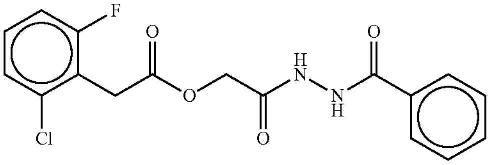 | −65.01 | −71.09 |
| B-174 | 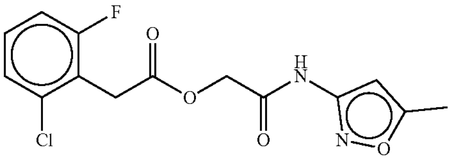 | −64.9 | −71.08 |
| B-175 | 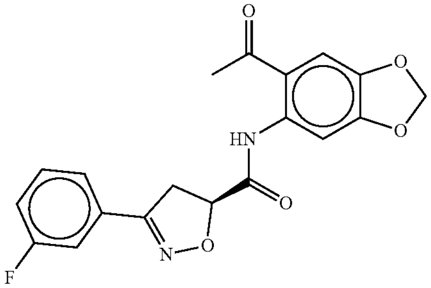 | −64.64 | −71.03 |
| B-176 | 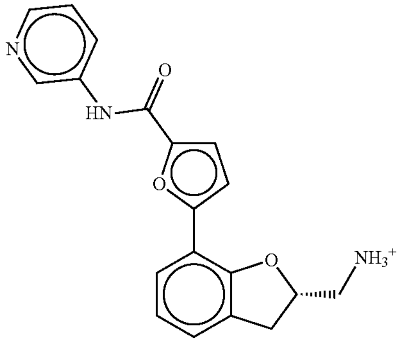 | −64.52 | −70.99 |
| B-177 | 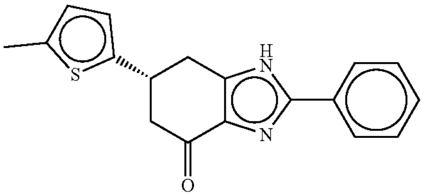 | −63.98 | −70.98 |

TABLE 2-continued
| Compound # | Structure | dG Bind Score | CSCORE |
| --- | --- | --- | --- |
| B-178 | 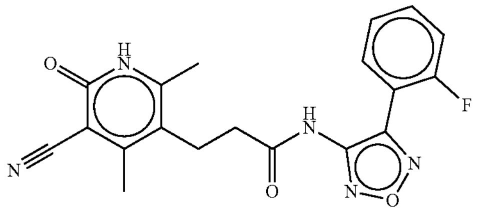 | −63.63 | −70.97 |
| B-179 | 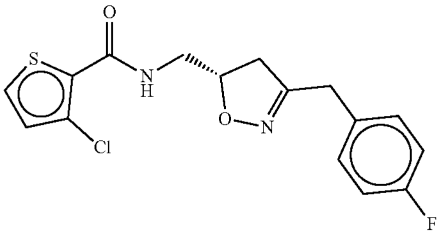 | −64.35 | −70.96 |
| B-180 | 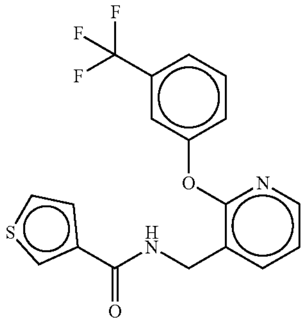 | −63.88 | −70.89 |
| B-181 | 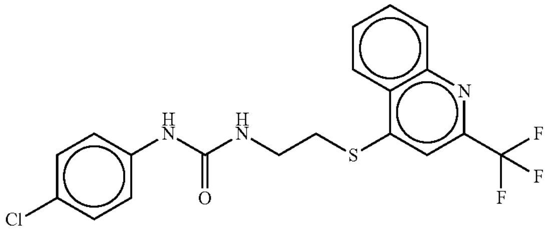 | −64.78 | −70.89 |
| B-182 | 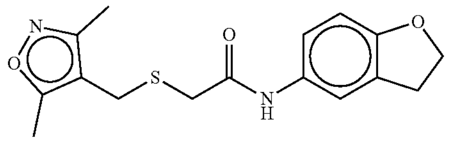 | −64.29 | −70.86 |
| B-183 | 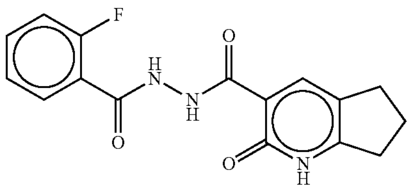 | −64.46 | −70.8 |
| B-184 | 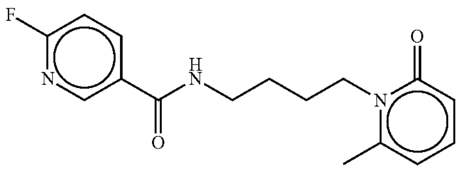 | −64.78 | −70.8 |

TABLE 2-continued
| Compound # | Structure | dG Bind Score | CSCORE |
|---|---|---|---|
| B-185 | 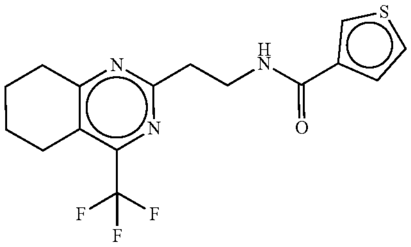 | −64.3 | −70.8 |
| B-186 | 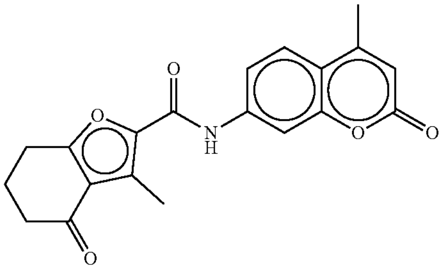 | −64.27 | −70.76 |
| B-187 | 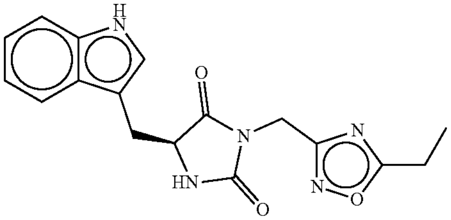 | −64.16 | −70.73 |
| B-188 | 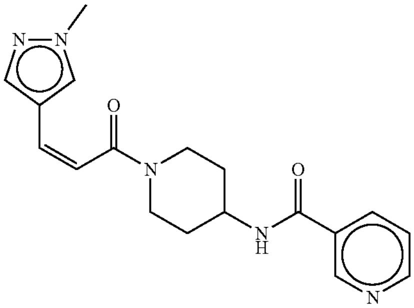 | −63.75 | −70.69 |
| B-189 | 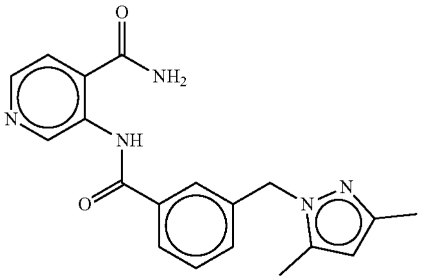 | −64.63 | −70.68 |
| B-190 | 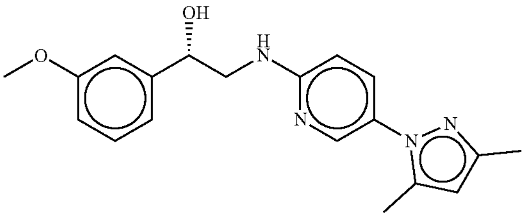 | −63.91 | −70.66 |

TABLE 2-continued
| Compound # | Structure | dG Bind Score | CSCORE |
|---|---|---|---|
| B-191 | 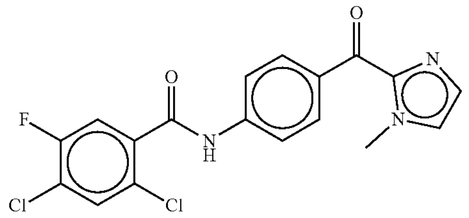 | −64.66 | −70.66 |
| B-192 | 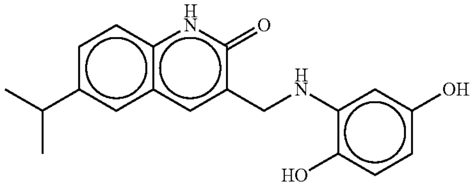 | −64.24 | −70.65 |
| B-193 | 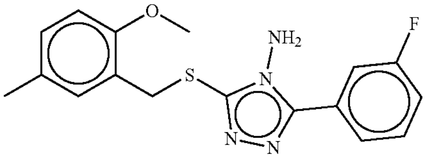 | −64.34 | −70.61 |
| B-194 | 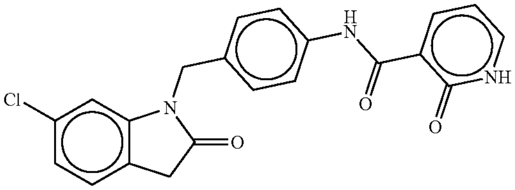 | −64.26 | −70.52 |
| B-195 | 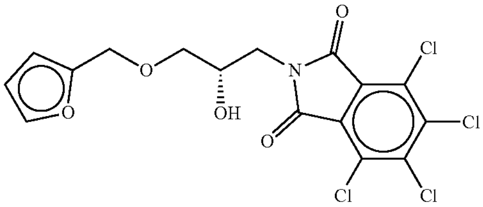 | −64.18 | −70.5 |
| B-196 | 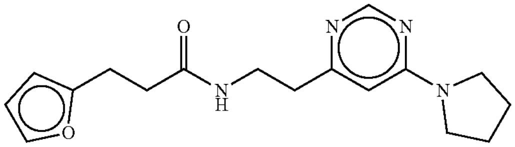 | −64.48 | −70.44 |
| B-197 | 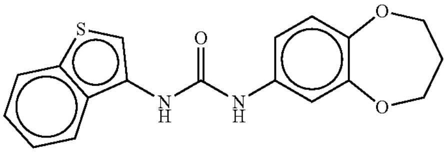 | −63.89 | −70.41 |
| B-198 | 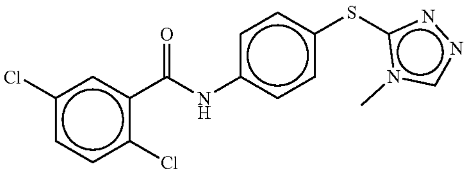 | −63.54 | −70.4 |

TABLE 2-continued
| Compound # | Structure | dG Bind Score | CSCORE |
|---|---|---|---|
| B-199 | 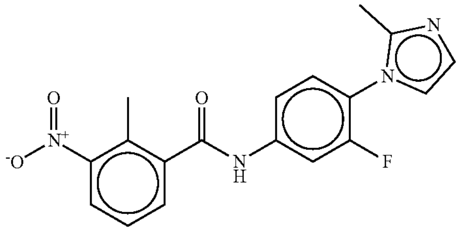 | −64.22 | −70.39 |
| B-200 | 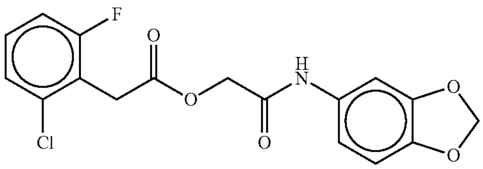 | −63.64 | −70.22 |
| B-201 | 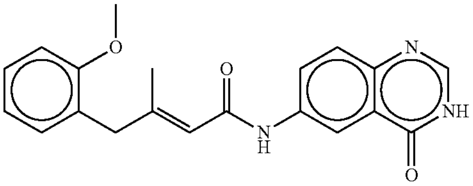 | −63.76 | −70.16 |
| B-202 | 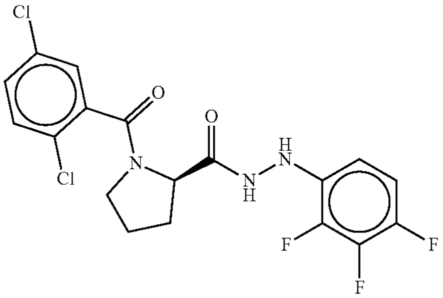 | −63.1 | −70.15 |
| B-203 | 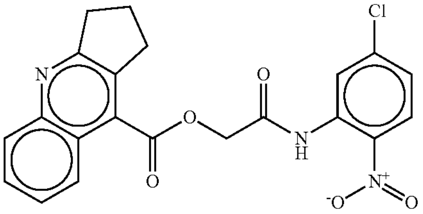 | −64.08 | −70.12 |
| B-204 | 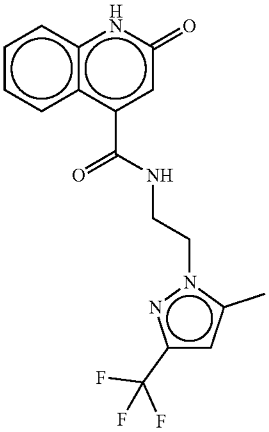 | −63.78 | −70.11 |

TABLE 2-continued
| Compound # | Structure | dG Bind Score | CSCORE |
| --- | --- | --- | --- |
| B-205 | 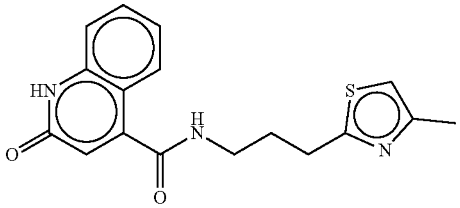 | −63.96 | −70.11 |
| B-206 | 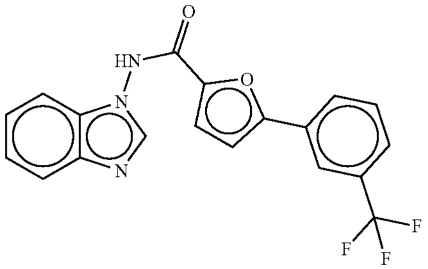 | −63.01 | −70.08 |
| B-207 | 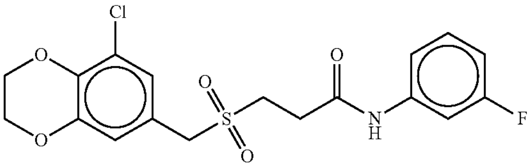 | −63.8 | −70.07 |
| B-208 | 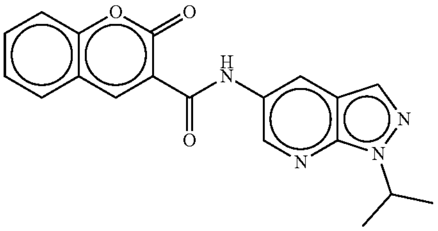 | −63.76 | −70.05 |
| B-209 | 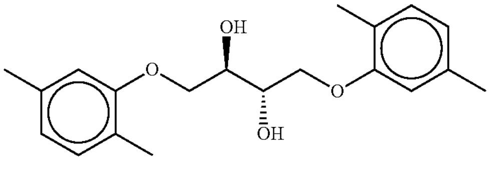 | −64.04 | −70.01 |
| B-210 | 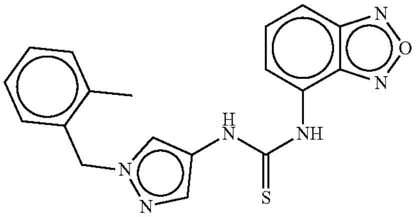 | −63.12 | −69.95 |
| B-211 | 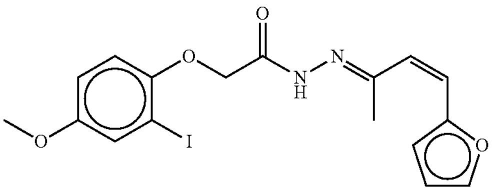 | −63.61 | −69.91 |

TABLE 2-continued
| Compound # | Structure | dG Bind Score | CSCORE |
| --- | --- | --- | --- |
| B-212 | 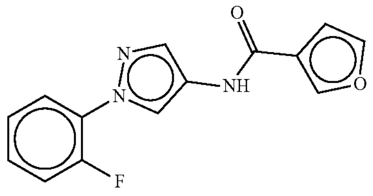 | −63.77 | −69.9 |
| B-213 | 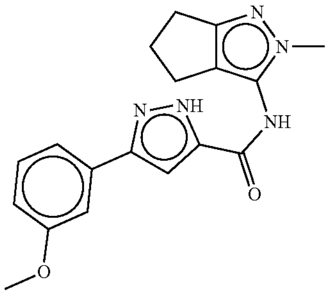 | −63.37 | −69.9 |
| B-214 | 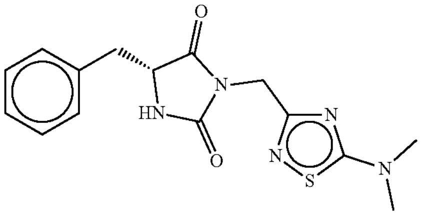 | −63.31 | −69.85 |
| B-215 | 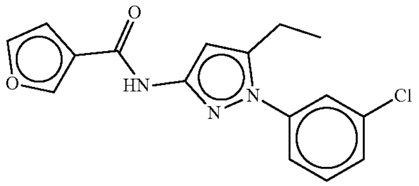 | −63.72 | −69.75 |
| B-216 | 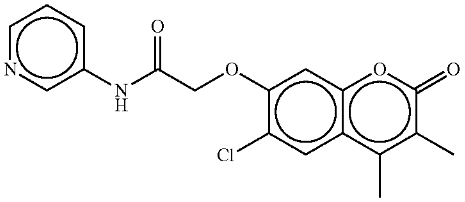 | −63.29 | −69.73 |
| B-217 | 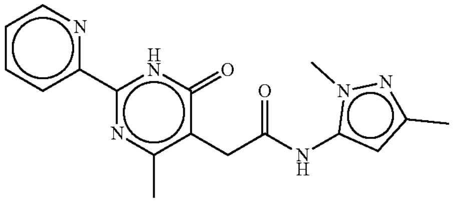 | −63.72 | −69.71 |

TABLE 2-continued
| Compound # | Structure | dG Bind Score | CSCORE |
|---|---|---|---|
| B-218 | 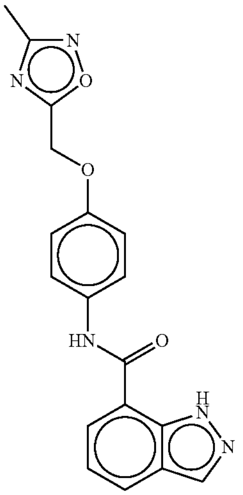 | −63.34 | −69.7 |
| B-219 | 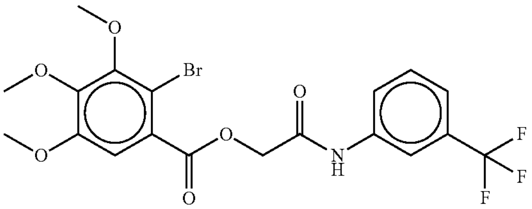 | −63.7 | −69.68 |
| B-220 | 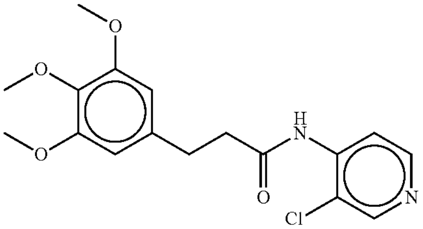 | −63.41 | −69.65 |
| B-221 | 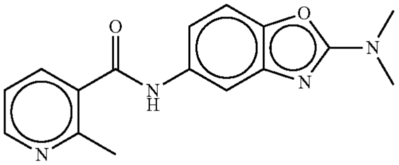 | −63.23 | −69.65 |
| B-222 | 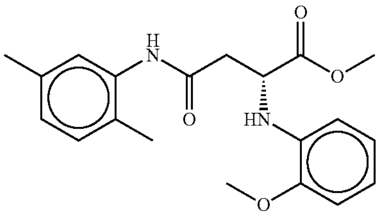 | −63.18 | −69.63 |
| B-223 | 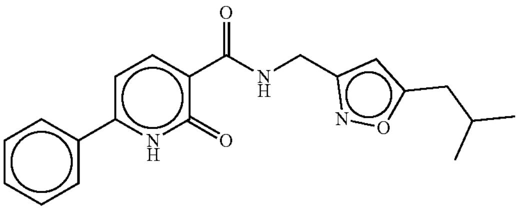 | −61.91 | −69.57 |

TABLE 2-continued
| Compound # | Structure | dG Bind Score | CSCORE |
|---|---|---|---|
| B-224 | 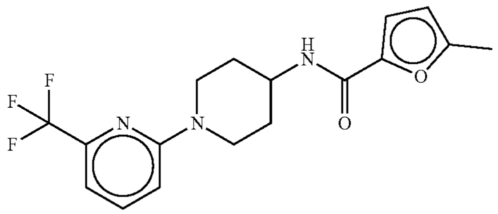 | −62.42 | −69.55 |
| B-225 | 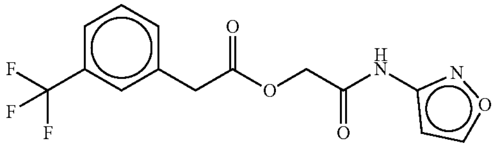 | −63.14 | −69.54 |
| B-226 | 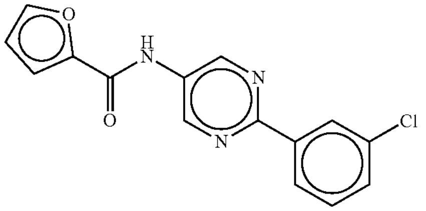 | −62.87 | −69.53 |
| B-227 | 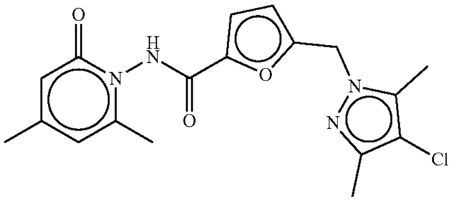 | −62.81 | −69.5 |
| B-228 | 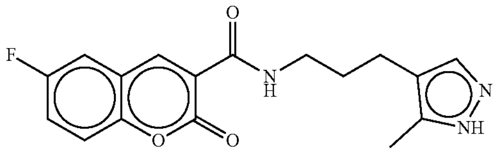 | −62.46 | −69.49 |
| B-229 | 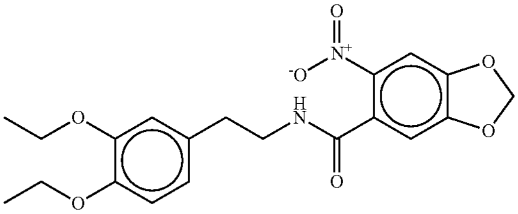 | −63.35 | −69.48 |
| B-230 | 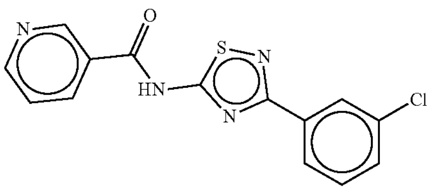 | −63.42 | −69.46 |

TABLE 2-continued
| Compound # | Structure | dG Bind Score | CSCORE |
|---|---|---|---|
| B-231 | 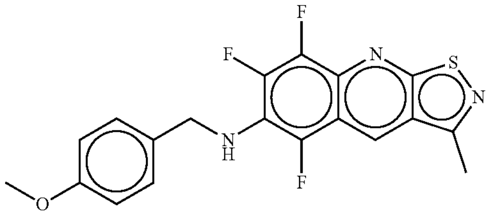 | −62.23 | −69.43 |
| B-232 | 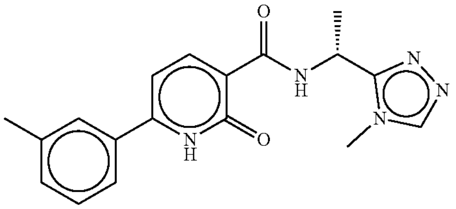 | −61.8 | −69.4 |
| B-233 | 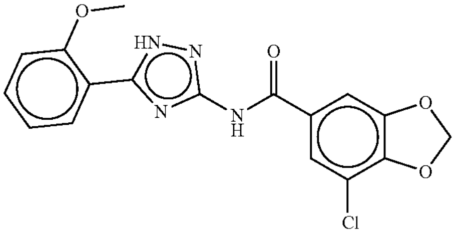 | −63.1 | −69.38 |
| B-234 | 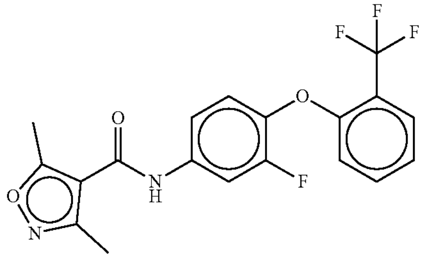 | −62.14 | −69.33 |
| B-235 | 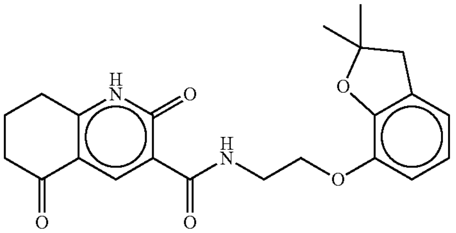 | −62.73 | −69.33 |
| B-236 | 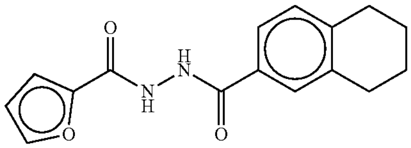 | −63.2 | −69.31 |
| B-237 | 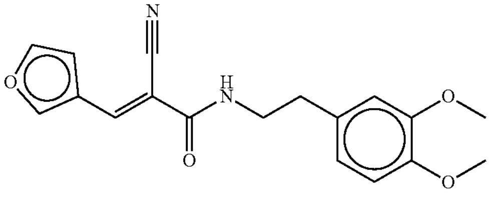 | −63.16 | 69.27 |

TABLE 2-continued
| Compound # | Structure | dG Bind Score | CSCORE |
|---|---|---|---|
| B-238 | 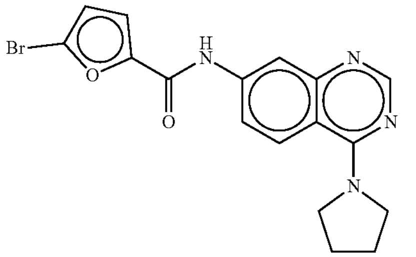 | −62.89 | −69.23 |
| B-239 | 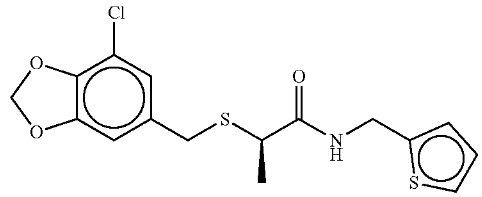 | −63.08 | −69.21 |
| B-240 | 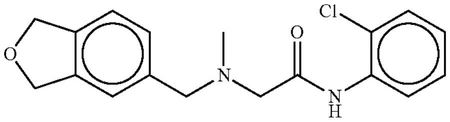 | −62.58 | −69.17 |
| B-241 | 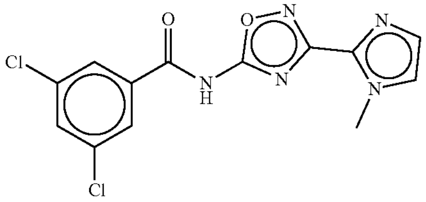 | −63.1 | −69.15 |
| B-242 | 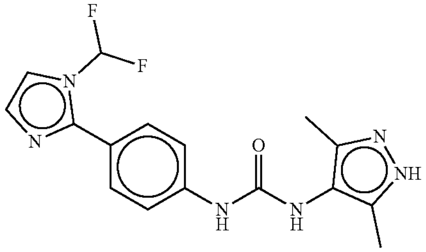 | −62.11 | −69.1 |
| B-243 | 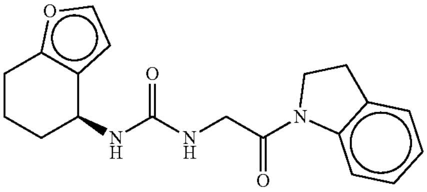 | −62.28 | −69.08 |
| B-244 | 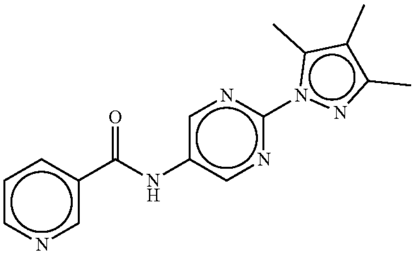 | −62.49 | −69.0 |

TABLE 2-continued
| Compound # | Structure | dG Bind Score | CSCORE |
| --- | --- | --- | --- |
| B-245 | 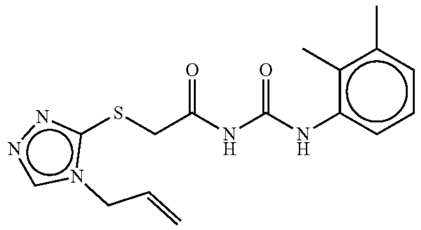 | −62.68 | −68.98 |
| B-246 | 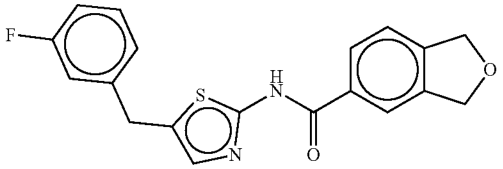 | −62.74 | −68.94 |
| B-247 | 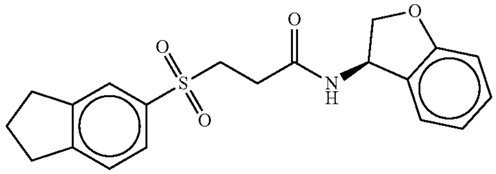 | −62.14 | −68.93 |
| B-248 | 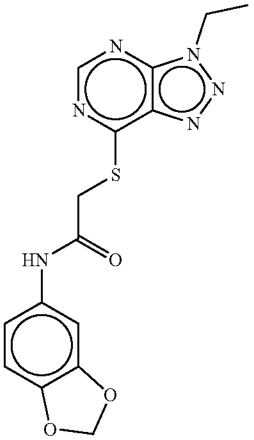 | −62.86 | −68.93 |
| B-249 | 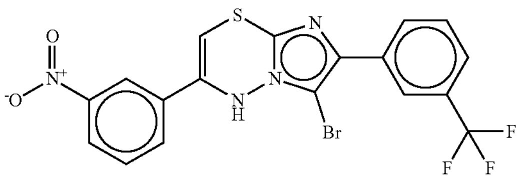 | −62.82 | −68.91 |
| B-250 | 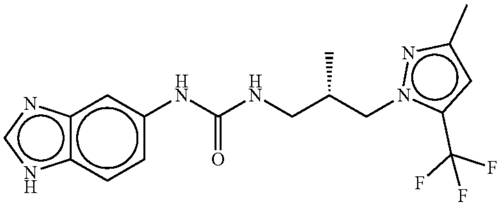 | −62.62 | −68.89 |

TABLE 2-continued
| Compound # | Structure | dG Bind Score | CSCORE |
|---|---|---|---|
| B-251 | 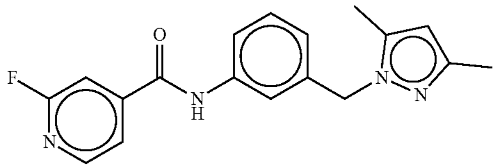 | −62.75 | −68.87 |
| B-252 | 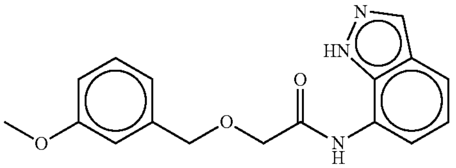 | −62.5 | −68.78 |
| B-253 | 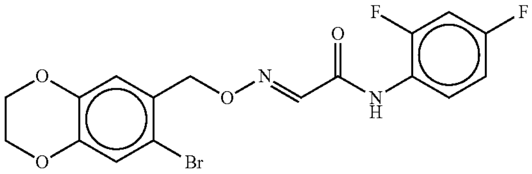 | −62.28 | −68.77 |
| B-254 | 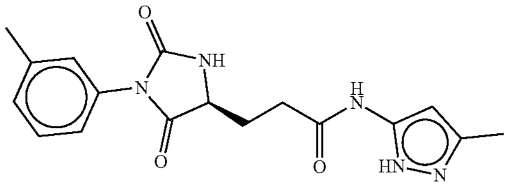 | −62.51 | −68.68 |
| B-255 | 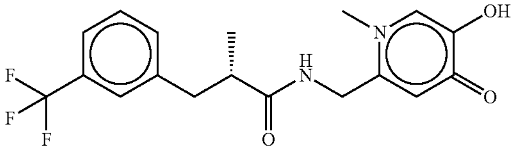 | −62.28 | −68.6 |
| B-256 | 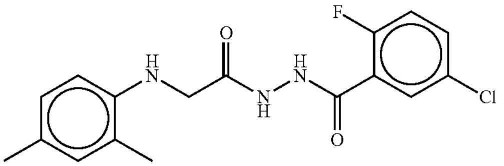 | −62.46 | −68.51 |
| B-257 | 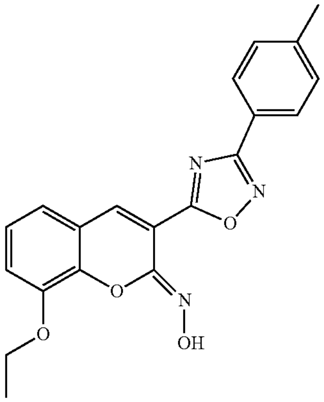 [SMILES: CCOc1cccc2cc(-c3nc(-c4ccc(C)cc4)no3)/c(=N/O)oc12] | −62.11 | −68.51 |

TABLE 2-continued
| Compound # | Structure | dG Bind Score | CSCORE |
|---|---|---|---|
| B-258 | 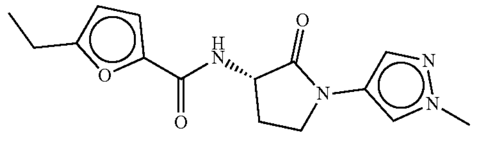 | −62.4 | −68.46 |
| B-259 | 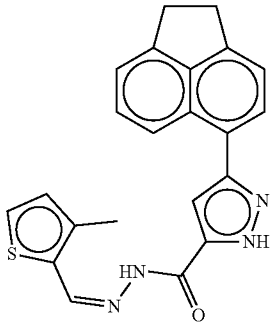 | −61.39 | −68.36 |
| B-260 | 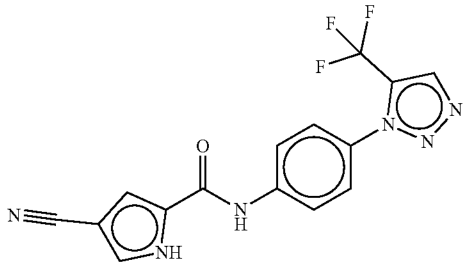 | −62.12 | −68.35 |
| B-261 | 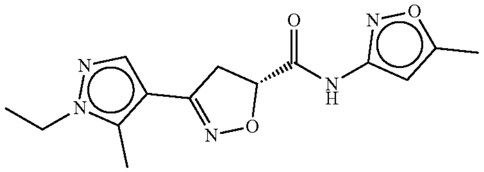 | −62.26 | −68.34 |
| B-262 | 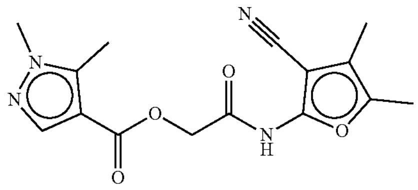 | −62.31 | −68.31 |
| B-263 | 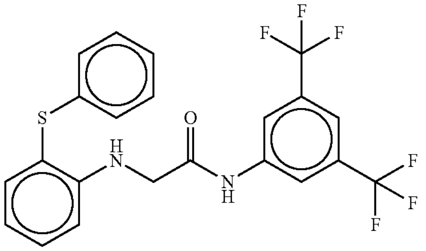 | −61.14 | −68.28 |

TABLE 2-continued
| Compound # | Structure | dG Bind Score | CSCORE |
|---|---|---|---|
| B-264 | 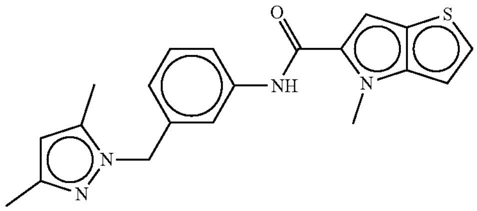 | −62.16 | −68.24 |
| B-265 | 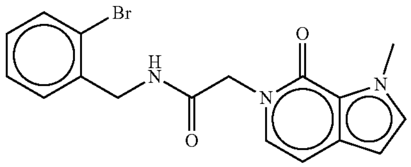 | −61.95 | −68.1 |
| B-266 | 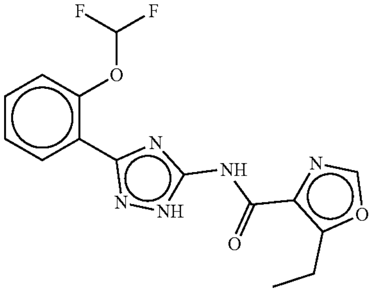 | −62.0 | −68.1 |
| B-267 | 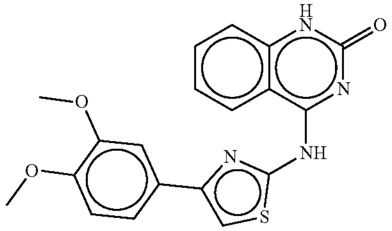 | −61.98 | −68.09 |
| B-268 | 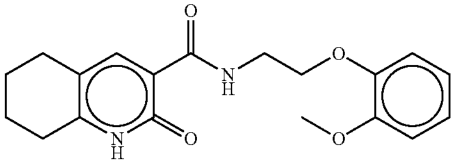 | −61.55 | −68.07 |
| B-269 | 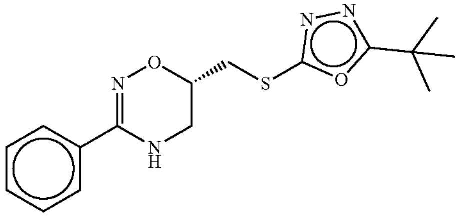 | −61.28 | −68.01 |
| B-270 | 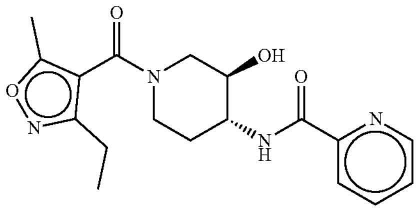 | −61.86 | −68.01 |

TABLE 2-continued
| Compound # | Structure | dG Bind Score | CSCORE |
|---|---|---|---|
| B-271 | 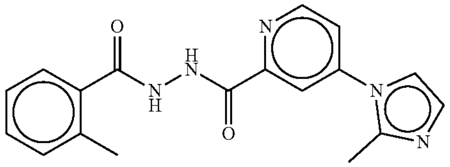 | −61.94 | −68.01 |
| B-272 | 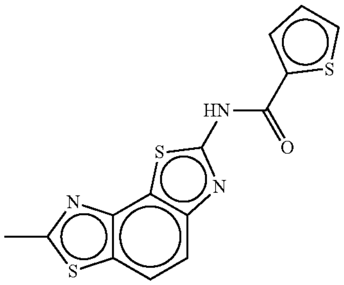 | −61.87 | −67.97 |
| B-273 | 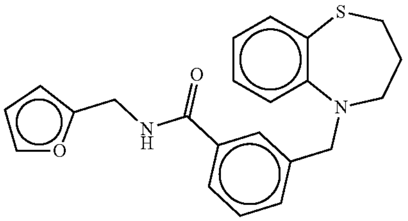 | −61.66 | −67.96 |
| B-274 | 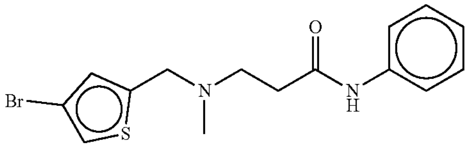 | −61.7 | −67.95 |
| B-275 | 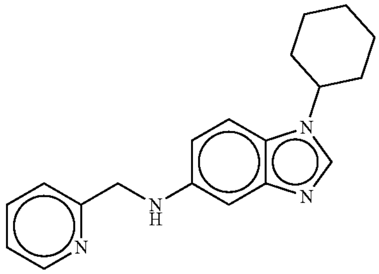 | −61.59 | −67.94 |
| B-276 | 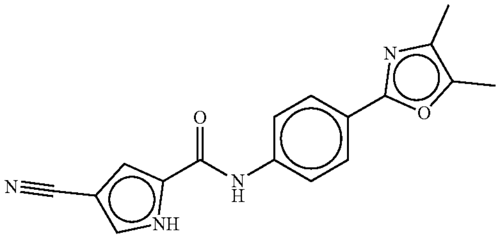 | −61.4 | −67.87 |
| B-277 | 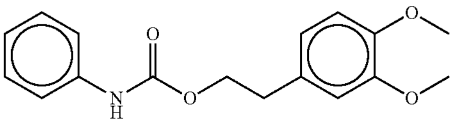 | −61.44 | −67.84 |

TABLE 2-continued
| Compound # | Structure | dG Bind Score | CSCORE |
|---|---|---|---|
| B-278 | 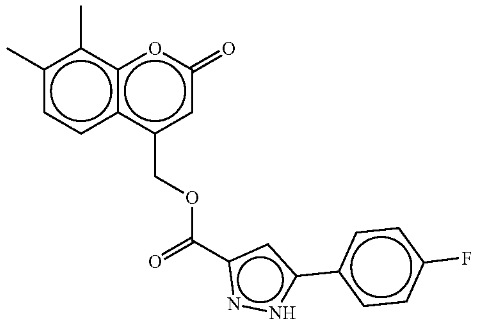 | −61.12 | −67.83 |
| B-279 | 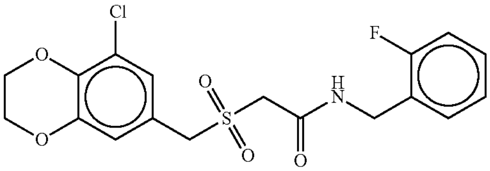 | −61.85 | −67.83 |
| B-280 | 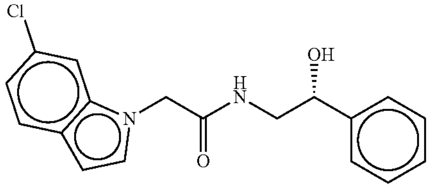 | −61.31 | −67.83 |
| B-281 | 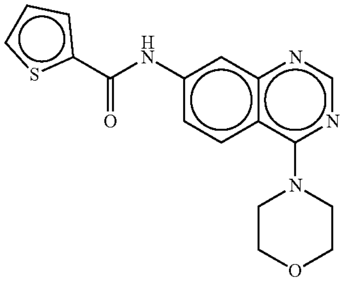 | −61.75 | −67.78 |
| B-282 | 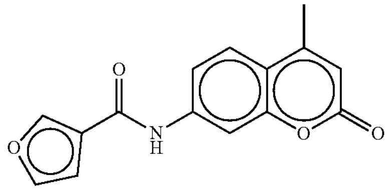 | −61.57 | −67.75 |
| B-283 | 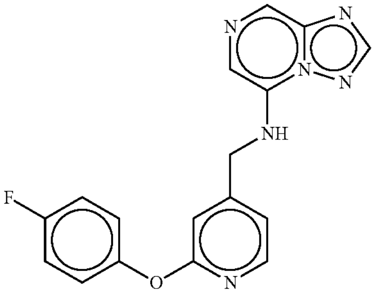 | −61.4 | −67.78 |

TABLE 2-continued
| Compound # | Structure | dG Bind Score | CSCORE |
| --- | --- | --- | --- |
| B-284 | 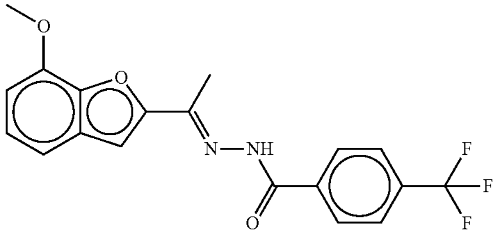 | −61.64 | −67.72 |
| B-285 | 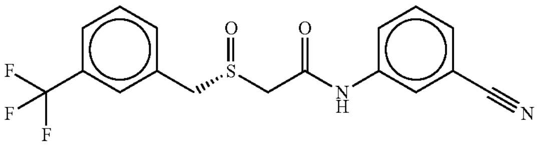 | −61.46 | −67.66 |
| B-286 | 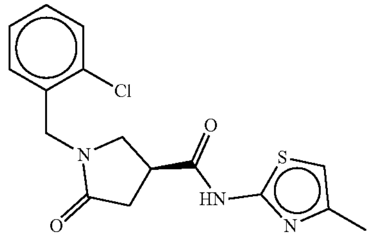 | −61.1 | −67.66 |
| B-287 | 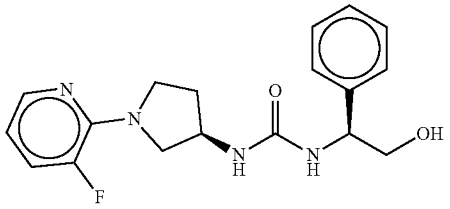 | −61.13 | −67.6 |
| B-288 | 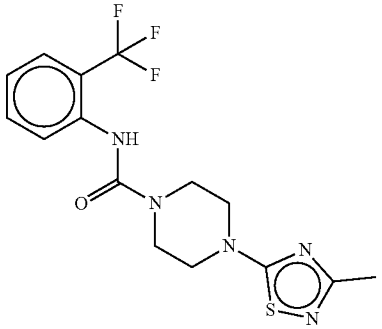 | −61.27 | −67.43 |
| B-289 | 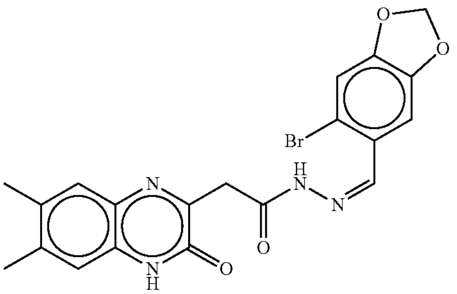 | −61.32 | −67.42 |

TABLE 2-continued

| Compound # | Structure | dG Bind Score | CSCORE |
|---|---|---|---|
| B-290 | 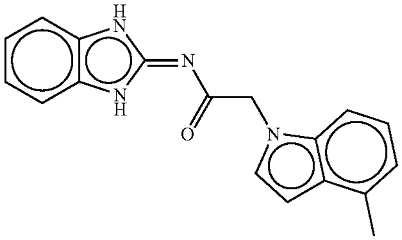 | −61.33 | −67.39 |
| B-291 | 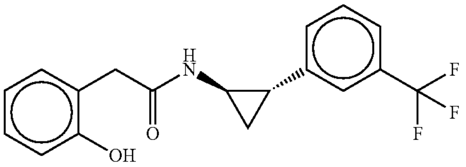 | −61.22 | −67.35 |
| B-292 | 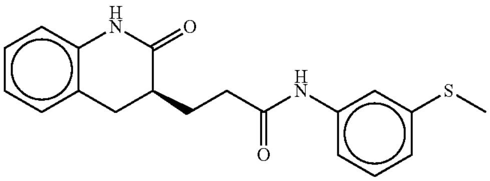 | −61.1 | −67.19 |
| B-293 | 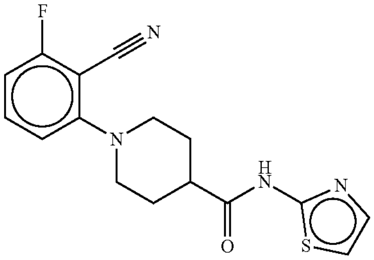 | −61.06 | −67.12 |

In some embodiments, the compound described herein can have the structure selected from compounds C-1 to C-9 in Table 3. In some embodiments, the compound comprises $L_A$, $L_B$, $L_C$, and $L_D$ moieties and does not contain $L_E$ moiety. In some embodiments, the compound in Table 3 comprises $L_A$, $L_B$, $L_C$, and $L_D$ moieties and does not contain $L_E$ moiety.

TABLE 3

| Compound # | Structure | dG Bind Score | CSCORE |
|---|---|---|---|
| C-1 | 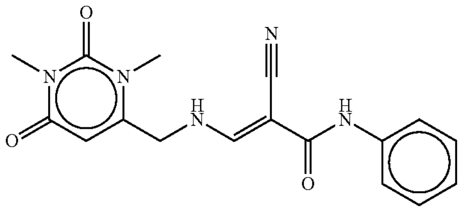 | −74.17 | −80.54 |
| C-2 | 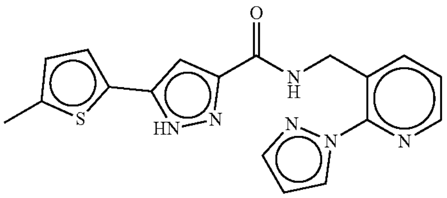 | −73.65 | −80.0 |

TABLE 3-continued

| Compound # | Structure | dG Bind Score | CSCORE |
|---|---|---|---|
| C-3 | 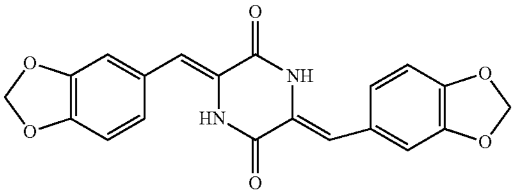 [SMILES: O=c1[nH]/c(=C\c2ccc3c(c2)OCO3)c(=O)[nH]/c1=C\c1ccc2c(c1)OCO2] | −71.0 | −78.32 |
| C-4 | 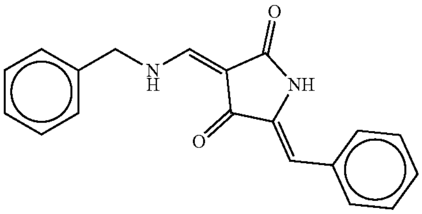 | −63.79 | −71.28 |
| C-5 | 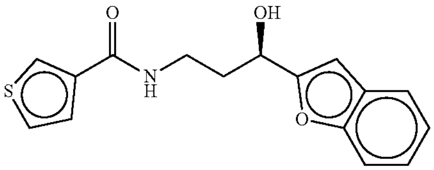 | −64.37 | −70.83 |
| C-6 | 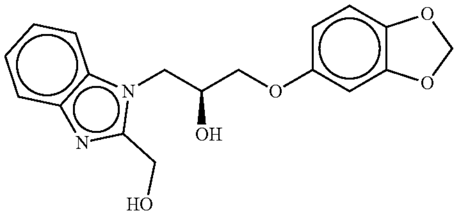 | −62.54 | −69.07 |
| C-7 | 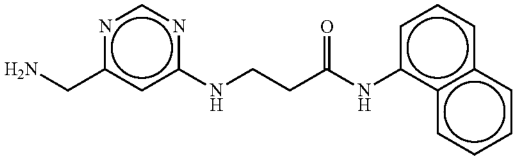 | −62.87 | −68.91 |
| C-8 | 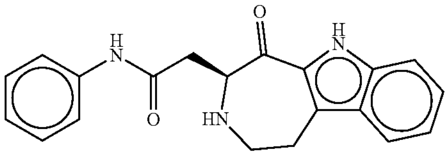 | −61.64 | −68.3 |
| C-9 | 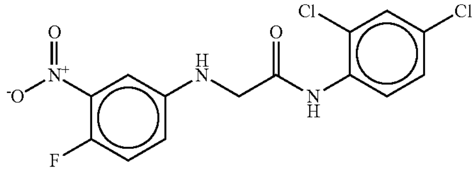 | −61.0 | −67.13 |

Some embodiments relate to a compound or a pharmaceutically acceptable salt, prodrug, ester thereof, comprising at least three moieties selected from $L_C$, $L_D$, $L_F$, or $L_G$, wherein:

$L_C$ is a moiety configured to hydrogen bond with a tubulin βE200 oxygen atom, wherein the distance between the oxygen atom and the hydrogen bonding atom of the $L_C$ moiety is less than 4 Å;

$L_D$ is a moiety configured to hydrogen bond with a tubulin βV238 oxygen atom, wherein the distance between the tubulin βV238 side chain and the hydrogen bonding atom of the $L_D$ moiety is less than 4 Å;

$L_F$ is a moiety configured to hydrogen bond with a tubulin αT179 oxygen atom, wherein the distance between the oxygen of the tubulin αT179 amide and the hydrogen bonding atom of $L_F$ is less than 8 Å; and $L_G$ is a moiety configured to hydrogen bond with a tubulin βG237 oxygen atom, wherein the distance between the oxygen of the tubulin βG237 and the hydrogen bonding atom of $L_G$ is less than 8 Å.

Some embodiments relate to a compound or a pharmaceutically acceptable salt, prodrug, ester thereof, comprising at least three moieties selected from $L_C$, $L_D$, $L_F$, or $L_G$, wherein:

$L_C$ is a moiety configured to hydrogen bond with a tubulin βE200 oxygen atom, wherein the distance between the oxygen atom and the hydrogen atom bonding atom of the $L_C$ moiety is less than 4 Å;

$L_D$ is a moiety configured to hydrogen bond with a tubulin βV238 side chain, wherein the distance between the tubulin βV238 side chain and the hydrogen atom bonding atom of the $L_D$ moiety is less than 4 Å;

$L_F$ is a moiety configured to hydrogen bond with a water molecule, wherein the water molecule in turn hydrogen bonds with a tubulin αT179 oxygen atom, wherein the distance between the oxygen of the tubulin αT179 amide and the hydrogen atom bonding atom of $L_F$ is less than 8 Å, preferably less than 4 Å;

$L_G$ is a moiety configured to hydrogen bond with a water molecule, wherein the water molecule in turn hydrogen bonds with a tubulin βG237 oxygen atom, wherein the distance between the oxygen of the tubulin βG237 and the hydrogen atom bonding atom of $L_G$ is less than 8 Å, preferably less than 4 Å.

In some embodiments, the compounds described herein include a structure of formula (I)

$L_A$-$X_1$-$X_2$-$L_B$ wherein:

$L_A$ is an optionally substituted $C_{5-10}$ aryl or optionally substituted five to ten membered heteroaryl, $X_1$ is an organic spacer having one or more chain atoms selected from C, O, N, and S, wherein three or more the adjacent atoms of the chain may optionally form an optionally substituted $C_{5-10}$ aryl or optionally substituted five to ten membered heteroaryl or form a four to ten membered heterocyclyl ring with the atoms on $A_1$, $X_2$ is absent or an organic linker comprising 1 to 4 chain atoms selected from C, O, N, and S, and $L_B$ is a substituted $C_{5-10}$ aryl or substituted five to ten membered heteroaryl.

In some embodiments, $L_A$ is an optionally substituted $C_{5-10}$ aryl or optionally substituted five to ten membered heteroaryl selected from the group consisting of pyrimidine, pyrrolidine, piperazine, piperidine, morpholino, hexahydroazepine, cyclohexene, piperideino, tetrahydroquinoline, tetrahydroisoquinoline, dihydropyrrole, phenyl, naphthyl, furane, pyrrole, thiophene, oxazole, isoxazole, imidazole, thiazole, oxadiazole, thiadiazole, triazole, pyridine, pyrimidine, pyridazine, pyrazine, quinoline, isoquinoline, benzothiazole, benzoimidazole and benzoxazole.

In some embodiments, $L_B$ is an optionally substituted $C_{5-10}$ aryl or optionally substituted five to ten membered heteroaryl selected from the group consisting of pyrimidine, pyrrolidine, piperazine, piperidine, morpholino, hexahydroazepine, cyclohexene, piperideino, tetrahydroquinoline, tetrahydroisoquinoline, dihydropyrrole, phenyl, naphthyl, furane, pyrrole, thiophene, oxazole, isoxazole, imidazole, thiazole, oxadiazole, thiadiazole, triazole, pyridine, pyrimidine, pyridazine, pyrazine, quinoline, isoquinoline, benzothiazole, benzoimidazole, isoindoline, 1,3-dihydroisobenzofuran, and benzoxazole.

In some embodiments, at least one of $L_A$ and $L_B$ is optionally substituted with one or more substituents selected from the group consisting of —$C_1$-$C_6$alkyl, —$C_2$-$C_6$alkenyl, —$C_2$-$C_6$alkynyl, $C_1$-$C_6$ heteroalkyl, $C_6$-$C_{10}$ aryl, five to ten numbered heteroaryl, halogenated $C_1$-$C_6$alkyl, $C_{3-10}$carbocyclyl, 3-10 membered heterocyclyl, —O—$C_1$-$C_6$alkyl, —O-halogenated $C_1$-$C_6$alkyl, —$C_1$-$C_6$alkyl-O—$C_1$-$C_6$alkyl, —S—$C_1$-$C_6$alkyl, amino, —$C_1$-$C_6$alkylelenamino, —C(O)H, —CO—$C_1$-$C_6$alkyl, —C(O)-amino, —$S(O)_2$-amino, —COO—$C_1$-$C_6$alkyl, —$C_1$-$C_6$alkyleneamide, —N($C_1$-$C_6$alkyl)(CO—$C_1$-$C_6$alkyl), —NH(CO—$C_1$-$C_6$alkyl), hydroxy, cyano, azido, nitro, —$CH_2CH(CH_3)_2OCH_2$—, —$OCH_2O$—, —$O(CH_2)_2O$—, and halogen.

In some embodiments, at least one of $L_A$ and $L_B$ is optionally substituted with one or more substituents, and the one or more substitutents together with the atoms on $L_A$ or $L_B$ form a $C_{3-10}$ cycloalkyl ring or three to ten membered heterocyclic ring.

In some embodiments, the $X_1$ is a cyclic or acyclic linker having a molecular weight less than 250 g/mol.

In some embodiments, the $X_1$ comprises one or more fragments selected from the group consisting of —C(O)—NH—, —$C_{1-6}$ alkylene, —S—, —O—, —$(CH_2)_{0-6}$—NH—, —CH(OH)—, —C(CN)═CH—, —CH═N—, optionally substituted phenylene, optionally substituted four to ten membered heterocyclylene, and optionally substituted five to ten membered heteroarylene.

In some embodiments, the $X_2$ comprises one or more fragments selected from the group consisting of —C(O)—NH—, —$C_{1-6}$ alkylene, —S—, —O—, —$(CH_2)_{0-6}$—NH—, —CH(OH)—, —C(CN)═CH—, and —CH═N—, and $X_2$ has a molecular weight that is in the range of 10 g/mol to about 250 g/mol.

The compound described herein have microtubule depolymerizing activity and can be effective chemotherapeutic agents. In some embodiments, the compounds described herein can reside in a deeper position in β-tubulin, making hydrogen bonds with βE200 on S6 and βV238 on H7, and also interacting with βG237 on H7 and with αT179 on T5 via water molecules.

The colchicine domain is a big pocket surrounded by two α-helices (H7 and H8) and by strands of the two tubulin β-sheets (S1-S4-S5-S6 and S7-S10-S8-S9) from the β subunit and is capped by two loops (βT7 and αT5). In some embodiments, βS7 paired with both βS6 and βS10 via its N-terminus and C-terminus, respectively, thus bridging the two β-sheets into a super β-sheet.

In some embodiments, the compound described herein includes a pharmacophore that comprise two or three hydrophobic moieties and at least two hydrogen bond moieties $L_C$ and $L_F$ (either hydrogen bond acceptor or donor). In some embodiments, the compound comprises a large hydrophobic group fitting into the hydrophobic core of the colchicine domain. In some embodiments, two extended hydrophobic pockets in the colchicine domain accommodate two other hydrophobic moieties: one is buried deeply in b-tubulin and the other one is located at the interface of the α/β tubulin heterodimer. In some embodiments, the hydrophilic groups (e.g., $L_C$ and $L_F$) may form hydrogen bonds with tubulin. In some embodiments, the pharmacophore can include two additional hydrogen bond moieties $L_D$ and $L_G$ that may form hydrogen bond with tubulin.

The compounds described herein may bind to β-tubulin. β-tubulin isotypes have a varied distribution in different cell types and modulate the cell sensitivity to chemotherapeutic drugs. Tumor cells may show differences in the expression of tubulin isotypes. The compounds described herein targeting tubulin may differentiate between different cell types, thus the undesirable side effects associated with current chemotherapeutic treatments may be reduced.

Regulation of the actin cytoskeleton by microtubules is mediated by the Rho family GTPases. The Rho guanine nucleotide exchange factor (GEF-H1) is regulated by an interaction with microtubules. GEF-H1 mutants that are deficient in microtubule binding have higher activity levels than microtubule-bound forms. These mutants also induce Rho-dependent changes in cell morphology and actin organization. Furthermore, drug-induced microtubule depolymerization induces changes in cell morphology and gene expression that are similar to the changes induced by the expression of active forms of GEF-H1. Furthermore, these effects may be inhibited by dominant-negative versions of GEF-H1. Thus, GEF-H1 links may change in microtubule integrity to Rho-dependent regulation of the actin cytoskeleton.

GEF-H1 is a microtubule-associated nucleotide exchange factor that is a member of the Dbl family of proteins. The N- or C-terminal portions of GEF-H1 may be involved in the interaction with microtubules and/or MAPs. A combination of N- or C-terminal protein domains may be necessary for microtubule binding. In some embodiments, the zinc finger domain may be involved in the interaction of GEF-H1 with microtubules. In some embodiments, the PH domain may be involved in the interaction of GEF-H1 with microtubules.

In some embodiments, GEF-H1 is inactive when bound to microtubules or tubulins and becomes activated when microtubules or tubulins are depolymerized, either as a result of inherent instability or after treatment with microtubule-depolymerizing drugs. Activated GEF-H1 promotes the binding of GTP to Rho, resulting in the activation of Rho, which in turn induces the upregulation of myosin II contractility, stress fiber assembly and SRE-regulated gene expression.

The expression of GEF-H1 constructs deficient in microtubule binding may induce changes in cell morphology, including cell retraction and the formation of actin stress fibers. This may be reminiscent of the changes induced by constitutively active RhoA. The expression of non-microtubule-associated GEF-H1 may result in the activation of RhoA. GEF-H1 can promote nucleotide exchange on RhoA, but not Rac or Cdc4, in cells expressing GEF-H1 constructs. GEF-H1 is a nucleotide exchange factor for Rho and are in a good agreement with the observation that Lfc, the mouse homologue of GEF-H1, is also specific for Rho25. The effects of GEF-H1 on cell morphology and gene expression are mediated by Rho, but not by Rac or Cdc42.

Microtubule depolymerization can activate Rho by increasing the amount of free, active GEF-H1, whereas microtubule assembly downregulates Rho by sequestering and inactivating GEF-H1. In migrating cells, microtubule depolymerization may locally activate Rho in the cell body, resulting in high myosin II activity and thus promoting tail retraction during locomotion. The prevalence of growing microtubules near the leading edge would result in low Rho activity at the front of the cell, allowing expansion of the leading edge to proceed without being hindered by myosin contractility. The inactivation of GEF-H1 by microtubule polymerization caused by the compounds described herein may also be utilized for treating proliferative disorders and other types of diseases or conditions described herein.

In some embodiments, the distance between the tubulin βE200 oxygen atom and the hydrogen bonding atom of the $L_C$ moiety is less than about 2 Å, 2.5 Å, 2.8 Å, 3 Å, 3.2 Å, 3.5 Å, 4 Å, 5 Å, 6 Å, 7 Å, 8 Å, 9 Å, or 10 Å. In some embodiments, the distance between the tubulin βE200 oxygen atom and the hydrogen bonding atom of the $L_C$ moiety is greater than about 0.5 Å, 1 Å, 1.25 Å, 1.5 Å, 1.8 Å, 2 Å, 2.5 Å, 2.8 Å, 3 Å, 3.2 Å, 3.5 Å, 4 Å, 5 Å, or 6 Å. In some embodiments, the tubulin βE200 distance between the oxygen atom and the hydrogen bonding atom of the $L_C$ moiety is about 2 Å, 2.1 Å, 2.2 Å, 2.3 Å, 2.4 Å, 2.5 Å, 2.6 Å, 2.7 Å, 2.8 Å, 2.9 Å, 3 Å, 3.2 Å, 3.5 Å, 4 Å, 5 Å, 6 Å, or 7 Å. In some embodiments, the tubulin βE200 distance between the oxygen atom and the hydrogen bonding atom of the $L_C$ moiety is in the range of about 0.5 Å-10 Å, 0.5 Å-9 Å, 0.5 Å-8 Å, 0.5 Å-7 Å, 0.5 Å-6 Å, 0.5 Å-5 Å, 0.5 Å-4 Å, 0.5 Å-3 Å, 0.5 Å-2.8 Å, 0.5 Å-2.5 Å, 0.5 Å-2 Å, 1 Å-10, 1 Å-9 Å, 1 Å-8 Å, 1 Å-7 Å, 1 Å-6 Å, 1 Å-5 Å, 1 Å-4 Å, 1 Å-3 Å, 1 Å-2.8 Å, 1 Å-2.5 Å, 1 Å-2 Å, 1.5 Å-10 Å, 1.5 Å-9 Å, 1.5 Å-8 Å, 1.5 Å-7 Å, 1.5 Å-6 Å, 1.5 Å-5 Å, 1.5 Å-4 Å, 1.5 Å-3 Å, 1.5 Å-2.8 Å, 1.5 Å-2.5 Å, 1.5 Å-2 Å, 2 Å-10 Å, 2 Å-9 Å, 2 Å-8 Å, 2 Å-7 Å, 2 Å-6 Å, 2 Å-5 Å, 2 Å-4 Å, 2 Å-3 Å, 2 Å-2.8 Å, 2 Å-2.5 Å, 2.5 Å-10 Å, 2.5 Å-9 Å, 2.5 Å-8 Å, 2.5 Å-7 Å, 2.5 Å-6 Å, 2.5 Å-5 Å, 2.5 Å-4 Å, 2.5 Å-3 Å, or 2.5 Å-2.8 Å. In some embodiments, the tubulin βE200 oxygen atom is an oxygen on the carboxyl group of the Glutamic acid side chain.

In some embodiments, the distance between the tubulin βV238 oxygen and the hydrogen bonding atom of the $L_D$ moiety is less than about 2 Å, 2.5 Å, 2.8 Å, 3 Å, 3.2 Å, 3.5 Å, 4 Å, 5 Å, 6 Å, 7 Å, 8 Å, 9 Å, or 10 Å. In some embodiments, the distance between the tubulin βV238 oxygen and the hydrogen bonding atom of the $L_D$ moiety is greater than about 0.5 Å, 1 Å, 1.25 Å, 1.5 Å, 1.8 Å, 2 Å, 2.5 Å, 2.9 Å, 3 Å, 3.2 Å, 3.5 Å, 4 Å, 5 Å, or 6 Å. In some embodiments, the distance between the tubulin βV238 oxygen and the hydrogen bonding atom of the $L_D$ moiety is about 2 Å, 2.1 Å, 2.2 Å, 2.3 Å, 2.4 Å, 2.5 Å, 2.6 Å, 2.7 Å, 2.8 Å, 2.9 Å, 3 Å, 3.2 Å, 3.5 Å, 4 Å, 5 Å, 6 Å, or 7 Å. In some embodiments, the distance between the tubulin βV238 oxygen and the hydrogen bonding atom of the $L_D$ moiety is in the range of about 0.5 Å-10 Å, 0.5 Å-9 Å, 0.5 Å-8 Å, 0.5 Å-7 Å, 0.5 Å-6 Å, 0.5 Å-5 Å, 0.5 Å-4 Å, 0.5 Å-3 Å, 0.5 Å-2.9 Å, 0.5 Å-2.5 Å, 0.5 Å-2 Å, 1 Å-10 Å, 1 Å-9 Å, 1 Å-8 Å, 1 Å-7 Å, 1 Å-6 Å, 1 Å-5 Å, 1 Å-4 Å, 1 Å-3 Å, 1 Å-2.9 Å, 1 Å-2.5 Å, 1 Å-2 Å, 1.5 Å-10 Å, 1.5 Å-9 Å, 1.5 Å-8 Å, 1.5 Å-7 Å, 1.5 Å-6 Å, 1.5 Å-5 Å, 1.5 Å-4 Å, 1.5 Å-3 Å, 1.5 Å-2.9 Å, 1.5 Å-2.5 Å, 1.5 Å-2 Å, 2 Å-10 Å, 2 Å-9 Å, 2 Å-8 Å, 2 Å-7 Å, 2 Å-6 Å, 2 Å-5 Å, 2 Å-4 Å, 2 Å-3 Å, 2 Å-2.9 Å, 2 Å-2.5 Å, 2.5 Å-10 Å, 2.5 Å-9 Å, 2.5 Å-8 Å, 2.5 Å-7 Å, 2.5 Å-6 Å, 2.5 Å-5 Å, 2.5 Å-4 Å, 2.5 Å-3 Å, or 2.5 Å-2.9 Å. In some embodiments, the tubulin βV238 oxygen atom is the oxygen atom of the amide group. In some embodiments, the amide group is part of the peptide backbone.

In some embodiments, the distance between the oxygen of the tubulin αT179 and the hydrogen bonding atom of $L_F$ is less than 8 Å. In some embodiments, the distance between the oxygen of the tubulin αT179 and the hydrogen bonding atom of $L_F$ is less than about 2 Å, 2.5 Å, 2.8 Å, 3 Å, 3.2 Å, 3.5 Å, 3.8 Å, 4 Å, 4.2 Å, 4.5 Å, 4.8 Å, 5 Å, 5.2 Å, 5.5 Å, 5.8 Å, 6 Å, 6.2 Å, 6.5 Å, 6.8 Å, 7 Å, 8 Å, 9 Å, or 10 Å. In some embodiments, the distance between the oxygen of the tubulin αT179 and the hydrogen bonding atom of $L_F$ is greater than about 0.5 Å, 1 Å, 1.25 Å, 1.5 Å, 1.8 Å, 2 Å, 2.5 Å, 2.9 Å, 3 Å, 3.2 Å, 3.5 Å, 4 Å, 5 Å, or 6 Å. In some embodiments, the distance between the oxygen of the tubulin αT179 and the hydrogen bonding atom of $L_F$ is in the range of about 0.5 Å-10 Å, 0.5 Å-9 Å, 0.5 Å-8 Å, 0.5 Å-7 Å, 0.5 Å-6 Å, 0.5 Å-5 Å, 0.5 Å-4.5 Å, 0.5 Å-4 Å, 0.5 Å-3.5 Å, 0.5 Å-3 Å, 0.5 Å-2 Å, 1 Å-10 Å, 1 Å-9 Å, 1 Å-8 Å, 1 Å-7 Å, 1 Å-6 Å, 1 Å-5.5 Å, 1 Å-5 Å, 1 Å-4.5 Å, 1 Å-4 Å, 1 Å-3

Å, 1 Å-2 Å, 1.5 Å-10 Å, 1.5 Å-9 Å, 1.5 Å-8 Å, 1.5 Å-7 Å, 1.5 Å-6 Å, 1.5 Å-5.5 Å, 1.5 Å-5 Å, 1.5 Å-4.5 Å, 1.5 Å-4 Å, 1.5 Å-3 Å, 1.5 Å-2 Å, 2 Å-10 Å, 2 Å-9 Å, 2 Å-8 Å, 2 Å-7 Å, 2 Å-6 Å, 2 Å-5.5 Å, 2 Å-5 Å, 2 Å-4.5 Å, 2 Å-4 Å, 2 Å-3.5 Å, 2 Å-3 Å, 2.5 Å-10 Å, 2.5 Å-9 Å, 2.5 Å-8 Å, 2.5 Å-7 Å, 2.5 Å-6 Å, 2.5 Å-5.5 Å, 2.5 Å-5 Å, 2.5 Å-4 Å, 2.5 Å-3 Å, 3 Å-10 Å, 3 Å-9 Å, 3 Å-8 Å, 3 Å-7 Å, 3 Å-6 Å, 3 Å-5.5 Å, 3 Å-5 Å, 3 Å-4.5 Å, 3 Å-4 Å, 3 Å-3.5 Å, 3.5 Å-10 Å, 3.5 Å-9 Å, 3.5 Å-8 Å, 3.5 Å-7 Å, 3.5 Å-6 Å, 3.5 Å-5.5 Å, 3.5 Å-5 Å, 3.5 Å-4 Å, 3.5 Å-3 Å, 4 Å-10 Å, 4 Å-9 Å, 4 Å-8 Å, 4 Å-7 Å, 4 Å-6 Å, 4 Å-5.5 Å, 4 Å-5 Å, or 4 Å-4.5 Å. In some embodiments, the oxygen of the tubulin αT179 is the oxygen of the amide group. In some embodiments, the amide group is part of the peptide backbone.

In some embodiments, the distance between the oxygen of the tubulin βG237 and the hydrogen bonding atom of $L_G$ is less than 8. In some embodiments, the distance between the oxygen of the tubulin βG237 and the hydrogen bonding atom of $L_G$ is less than 2 Å, 2.5 Å, 2.8 Å, 3 Å, 3.2 Å, 3.5 Å, 3.8 Å, 4 Å, 4.2 Å, 4.5 Å, 4.8 Å, 5 Å, 5.2 Å, 5.5 Å, 5.8 Å, 6 Å, 6.2 Å, 6.5 Å, 6.8 Å, 7 Å, 8 Å, 9 Å, or 10 Å. In some embodiments, the distance between the oxygen of the tubulin βG237 and the hydrogen bonding atom of $L_G$ is greater than about 0.5 Å, 1 Å, 1.25 Å, 1.5 Å, 1.8 Å, 2 Å, 2.5 Å, 2.9 Å, 3 Å, 3.2 Å, 3.5 Å, 4 Å, 5 Å, or 6 Å. In some embodiments, the distance between the oxygen of the tubulin βG237 and the hydrogen bonding atom of $L_G$ is in the range of about 0.5 Å-10 Å, 0.5 Å-9 Å, 0.5 Å-8 Å, 0.5 Å-7 Å, 0.5 Å-6 Å, 0.5 Å-5 Å, 0.5 Å-4.5 Å, 0.5 Å-4 Å, 0.5 Å-3.5 Å, 0.5 Å-3 Å, 0.5 Å-2 Å, 1 Å-10 Å, 1 Å-9 Å, 1 Å-8 Å, 1 Å-7 Å, 1 Å-6 Å, 1 Å-5.5 Å, 1 Å-5 Å, 1 Å-4.5 Å, 1 Å-4 Å, 1 Å-3 Å, 1 Å-2 Å, 1.5 Å-10 Å, 1.5 Å-9 Å, 1.5 Å-8 Å, 1.5 Å-7 Å, 1.5 Å-6 Å, 1.5 Å-5.5 Å, 1.5 Å-5 Å, 1.5 Å-4.5 Å, 1.5 Å-4 Å, 1.5 Å-3 Å, 1.5 Å-2 Å, 2 Å-10 Å, 2 Å-9 Å, 2 Å-8 Å, 2 Å-7 Å, 2 Å-6 Å, 2 Å-5.5 Å, 2 Å-5 Å, 2 Å-4.5 Å, 2 Å-4 Å, 2 Å-3.5 Å, 2 Å-3 Å, 2.5 Å-10 Å, 2.5 Å-9 Å, 2.5 Å-8 Å, 2.5 Å-7 Å, 2.5 Å-6 Å, 2.5 Å-5.5 Å, 2.5 Å-5 Å, 2.5 Å-4 Å, 2.5 Å-3 Å, 3 Å-10 Å, 3 Å-9 Å, 3 Å-8 Å, 3 Å-7 Å, 3 Å-6 Å, 3 Å-5.5 Å, 3 Å-5 Å, 3 Å-4.5 Å, 3 Å-4 Å, 3 Å-3.5 Å, 3.5 Å-10 Å, 3.5 Å-9 Å, 3.5 Å-8 Å, 3.5 Å-7 Å, 3.5 Å-6 Å, 3.5 Å-5.5 Å, 3.5 Å-5 Å, 3.5 Å-4 Å, 3.5 Å-3 Å, 4 Å-10 Å, 4 Å-9 Å, 4 Å-8 Å, 4 Å-7 Å, 4 Å-6 Å, 4 Å-5.5 Å, 4 Å-5 Å, or 4 Å-4.5 Å. In some embodiments, the oxygen of the tubulin βG237 is the oxygen of the amide group. In some embodiments, the amide group is part of the peptide backbone.

In some embodiments, $L_C$ is a hydrophilic atom or hydrophilic functional group having a molecular weight or less than 200, 150, 100, 80, or between 14 and 200 g/mol. In some embodiments, $L_C$ is a nitrogen atom or a functional group containing at least one nitrogen atom.

In some embodiments, $L_D$ is a hydrophilic atom or hydrophilic functional group having a molecular weight or less than 200, 150, 100, 80, or between 14 and 200 g/mol. In some embodiments, $L_D$ is an oxygen atom or a functional group containing at least one oxygen atom.

In some embodiments, $L_F$ is a hydrophilic atom or hydrophilic functional group having a molecular weight or less than 200, 150, 100, 80, or between 14 and 200 g/mol. In some embodiments, $L_F$ is a nitrogen atom or a functional group containing at least one nitrogen atom.

In some embodiments, $L_G$ is a hydrophilic atom or hydrophilic functional group having a molecular weight or less than 200, 150, 100, 80, or between 14 and 200 g/mol. In some embodiments, $L_G$ is a nitrogen atom or a functional group containing at least one nitrogen atom.

In some embodiments, the hydrophilic atom or functional group within $L_C$, $L_D$, $L_F$, or $L_G$ is selected from C(O), NH, N, CHX, CH2X, CX2, CX3, OH, SO2, SH, C(S), SO3, and PO3, wherein each X is independently a halogen.

In some embodiments, the hydrogen bond between $L_F$ and the tubulin αT179 comprises a water bridge ($L_F$ hydrogen bonds with a water molecule and the water molecule in turn hydrogen bonds with the tubulin αT179).

In some embodiments, the hydrogen bond between $L_G$ and the tubulin βG237 comprises a water bridge ($L_G$ hydrogen bonds with a water molecule and the water molecule in turn hydrogen bonds with the tubulin βG237).

In some embodiments, the hydrogen bond between $L_D$ and βV238 comprises a water bridge. In some embodiments, the hydrogen bond of $L_D$ does not have a water bridge.

In some embodiments, the hydrogen bond between $L_D$ and the tubulin βE200 comprises a water bridge. In some embodiments, the hydrogen bond of $L_D$ does not comprise a water bridge.

In some embodiments, the compound described herein further comprises a hydrophobic moiety. In some embodiments, the hydrophobic moiety can be a $C_{1-20}$ alkyl; $C_{2-6}$ alkenyl; $C_{2-6}$ alkynyl; $C_{1-6}$ heteroalkyl; $C_{3-7}$ carbocyclyl; 4-10 membered heterocyclyl; $C_{6-10}$ aryl; 3-10 membered heteroaryl, each optionally substituted with one or more substituents. In some embodiments, the hydrophobic moiety can be a $C_{6-10}$ aryl optionally substituted with one or more substituents. In some embodiments, the hydrophobic moiety can be an optionally substituted phenyl group. In some embodiments, the hydrophobic moiety is selected from $C_{3-10}$ alkyl, $C_{3-10}$ carbocyclyl, phenyl, benzyl, and benzylidene.

In some embodiments, the compound described herein further comprises a first moiety that interacts with one or more domains of GEF-H1.

In some embodiments, the tubulin, upon binding of the compound, comprises a second moiety that interacts with one or more domains of GEF-H1.

In some embodiments, the tubulin, upon binding of the compound, activates the GEF-H1.

In some embodiments, the first moiety of the compound interacts with a N-terminal zinc finger domain of the GEF-H1. In some embodiments, the compound interacts with C53 of the GEF-H1.

In some embodiments, the second moiety of the tubulin interacts with a N-terminal zinc finger domain of the GEF-H1. In some embodiments, the tubulin interacts with C53 of the GEF-H1.

In some embodiments, the first moiety of the compound interacts with a C-terminal of the GEF-H1.

In some embodiments, the second moiety of the tubulin interacts with a C-terminal of the GEF-H1.

In some embodiments, the compound has a structure of formula (II)

(II)

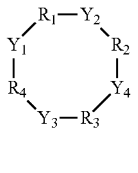

or a pharmaceutically acceptable salt, prodrug, ester thereof, wherein:

$Y_1$ is $L_C$ or

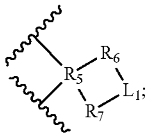

$Y_2$ is $L_D$ or

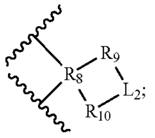

$Y_3$ is $L_F$ or

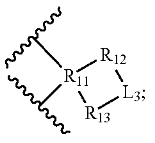

$Y_4$ is $L_G$ or

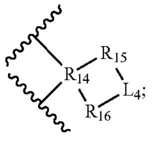

each of $R_1$, $R_2$, $R_3$, $R_4$, $R_6$, $R_7$, $R_9$, $R_{10}$, $R_{12}$, $R_{13}$, $R_{15}$, and $R_{16}$ is independently a bond or an organic moiety having a molecular weight between 14 g/mol and 200 g/mol; and each of $R_5$, $R_8$, $R_{11}$, and $R_{14}$, is independently an organic moiety having a molecular weight between 14 g/mol and 200 g/mol.

In some embodiments, the compound has the structure of formula (II):

(III)

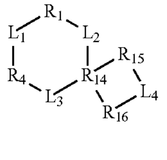

or a pharmaceutically acceptable salt, prodrug, ester thereof.

In some embodiments, one or more of $R_1$, $R_2$, $R_3$, $R_4$, $R_6$, $R_7$, $R_9$, $R_{10}$, $R_{12}$, $R_{13}$, $R_{15}$, and $R_{16}$ is a hydrophobic moiety. In some embodiments, $R^4$ and $R^{16}$ are hydrophobic moieties.

In some embodiments, one or more of $R_1$, $R_2$, $R_3$, $R_4$, $R_6$, $R_7$, $R_9$, $R_{10}$, $R_{12}$, $R_{13}$, $R_{15}$, and $R_{16}$ is a moiety that interacts with one or more domains of GEF-H1. In some embodiments, the one or more domains is a zinc finger domain. In some embodiments, one or more of $R_1$, $R_2$, $R_3$, $R_4$, $R_6$, $R_7$, $R_9$, $R_{10}$, $R_{12}$, $R_{13}$, $R_{15}$, and $R_{16}$ is a moiety that interacts with $C_{53}$ of GEF-H1.

In some embodiments, the compound described herein comprises the proviso that the compound is not a compound having the structure of formula (III)

(IV)

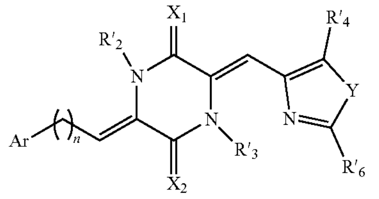

Wherein:

$R'_2$ and $R'_3$ are each separately selected from the group consisting of a hydrogen atom; a halogen atom; mono-substituted; poly-substituted or unsubstituted, straight or branched chain variants of the following residues: $C_1$-$C_{12}$ alkyl, $C_2$-$C_{12}$ alkenyl, and alkoxy; and mono-substituted, poly-substituted or unsubstituted variants of the following residues: cycloalkyl, cycloalkoxy, aryl, heteroaryl, amino, and nitro;

$R'_4$ and $R'_6$ are each separately selected from the group consisting of hydrogen; halogen; hydroxyl; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, alkoxy, arylalkyl, heteroarylalkyl, alkyloxycarbonyloxy, alkylcarbonyloxyalkyl, arylcarbonyloxyalkyl, arylalkoxy, alkoxy, and alkylthio; mono-substituted, poly-substituted or unsubstituted variants of the following residues: aryloxycarbonyloxy, cycloalkyl, cycloalkenyl, cycloalkoxy, aryl, heteroaryl, aryloxy, arylcarbonyl, heterocycloalkyl, amino, aminocarbonyl, amide, aminocarbonyloxy, nitro, azido, phenyl, hydroxyl, thio, alkylthio, arylthio, thiophenyl, carboxy, and cyano;

$X_1$ and $X_2$ are separately selected from the group consisting of an oxygen atom, a sulfur atom, and a nitrogen atom substituted with a $R'_5$ group;

$R'_5$ is selected from the group consisting of a hydrogen atom, a halogen atom, and saturated $C_1$-$C_{12}$ alkyl, unsaturated $C_2$-$C_{12}$ alkenyl, cycloalkyl, alkoxy, cycloalkoxy, aryl, substituted aryl, heteroaryl, substituted heteroaryl, amino, substituted amino, nitro, and substituted nitro groups;

Y is selected from the group consisting of an oxygen atom, a sulfur atom, an oxidized sulfur atom, and a nitrogen atom substituted with an $R'_5$ group;

n is 0, 1, 2, 3, or 4; and

Ar is a cyclic or polycyclic aryl or heteroaryl ring system comprising between one and three rings, wherein:

each ring in said system is separately a 5, 6, 7, or 8 membered ring;

each ring in said system separately comprises 0, 1, 2, 3, or 4 heteroatoms selected from the group consisting of oxygen, sulfur, and nitrogen; and each ring in said system is optionally substituted with one or more substituents selected from the group consisting of hydrogen; halogen; hydroxyl; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, alkoxy, arylalkyl, heteroarylalkyl, alkyloxycarbonyloxy, alkylcarbonyloxyalkyl, arylcarbonyloxyalkyl, arylalkoxy, alkoxy, and alkylthio; mono-substituted, poly-substituted or unsubstituted variants of the following residues: aryloxycarbonyloxy, cycloalkyl, cycloalkenyl, cycloalkoxy, aryl, heteroaryl, aryloxy, arylcarbonyl, heterocycloalkyl, amino, aminocarbonyl, amide, aminocarbonyloxy, nitro, azido, phenyl, hydroxyl, thio, alkylthio, arylthio, thiophenyl, carboxy, and cyano; and an optionally substituted fused ring selected from the group consisting of dioxole, dithiole, oxathiole, dioxine, dithiine, and oxathiine.

In some embodiments, the compound described herein is not plinabulin. In some embodiments, the compound is not dehydrophenylahistin, phenylahistin, or t-butyl-phenylahistin. In some embodiments, the compound is not a dehydrophenylahistin, or phenylahistin derivatives.

In some embodiments, the compound described herein is not any of the compounds listed in Table A or Table B below.

TABLE A

| Phenylahistin and dehydrophenylahistin derivatives | |
|---|---|
| Structure | Chemical name |
| 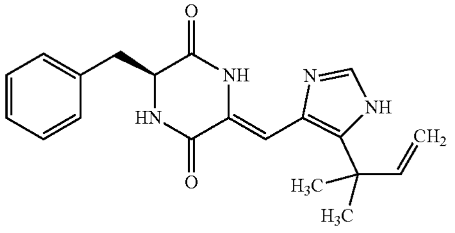 [SMILES: C=CC(C)(C)c1[nH]cnc1/C=C1\NC(=O)[C@H](Cc2ccccc2)NC1=O] | (−)-(S)-Halimide, (−)-(S)-Phenylahistin, (−)-(S)-PLH |
| 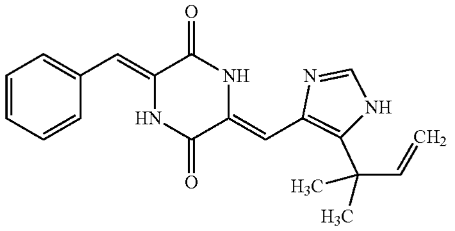 [SMILES: C=CC(C)(C)c1[nH]cnc1/C=c1\[nH]c(=O)/c(=C/c2ccccc2)[nH]c1=O] | Dehydrophenylahistin, delta-PLH, KPU-1 |
| 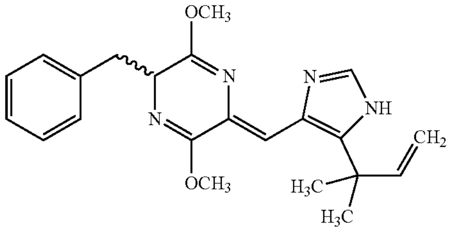 [SMILES: C=CC(C)(C)c1[nH]cnc1/C=C1\N=C(OC)C(Cc2ccccc2)N=C1OC] | KPU-4, D,L-bislactim-PLH |
| 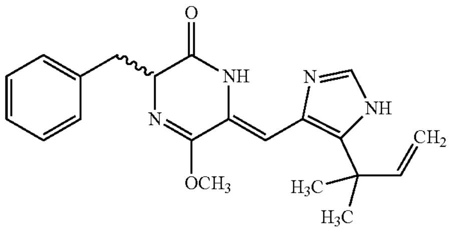 [SMILES: C=CC(C)(C)c1[nH]cnc1/C=C1\NC(=O)C(Cc2ccccc2)N=C1OC] | KPU-5, D,L-monolactim-PLH |
| 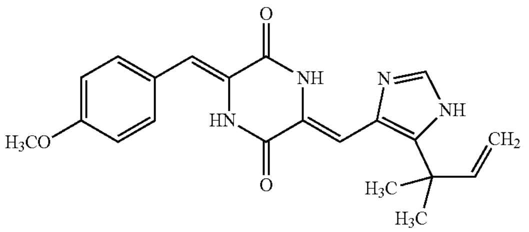 [SMILES: C=CC(C)(C)c1[nH]cnc1/C=c1\[nH]c(=O)/c(=C/c2ccc(OC)cc2)[nH]c1=O] | KPU-6 |

TABLE A-continued
| Phenylahistin and dehydrophenylahistin derivatives | |
|---|---|
| Structure | Chemical name |
| 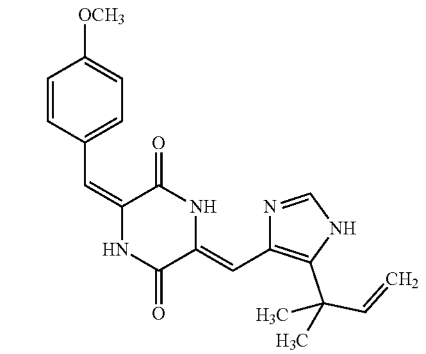 [SMILES: C=CC(C)(C)c1[nH]cnc1/C=c1\[nH]c(=O)/c(=C\c2ccc(OC)cc2)[nH]c1=O] | KPU-7 |
| 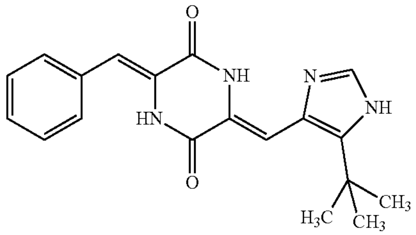 [SMILES: CC(C)(C)c1[nH]cnc1/C=c1\[nH]c(=O)/c(=C/c2ccccc2)[nH]c1=O] | t-butyl-delta-PLH, KPU-2 |
| 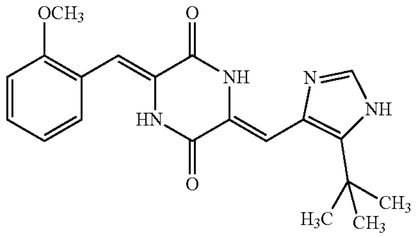 [SMILES: COc1ccccc1/C=c1\[nH]c(=O)/c(=C/c2nc[nH]c2C(C)(C)C)[nH]c1=O] | KPU-8 |
| 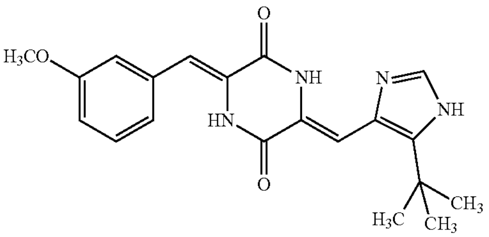 [SMILES: COc1cccc(/C=c2\[nH]c(=O)/c(=C/c3nc[nH]c3C(C)(C)C)[nH]c2=O)c1] | KPU-9 |
| 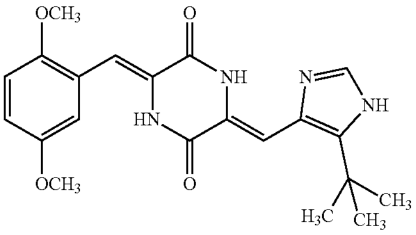 [SMILES: COc1ccc(OC)c(/C=c2\[nH]c(=O)/c(=C/c3nc[nH]c3C(C)(C)C)[nH]c2=O)c1] | KPU-10 |

TABLE A-continued
| Phenylahistin and dehydrophenylahistin derivatives | |
|---|---|
| Structure | Chemical name |
| 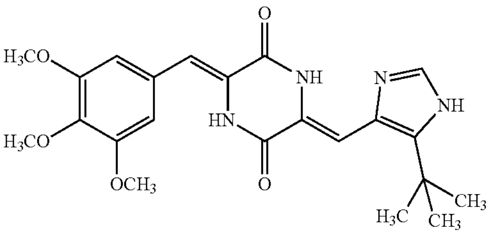 [SMILES: COc1cc(/C=c2\[nH]c(=O)/c(=C/c3nc[nH]c3C(C)(C)C)[nH]c2=O)cc(OC)c1OC] | KPU-11 |
| 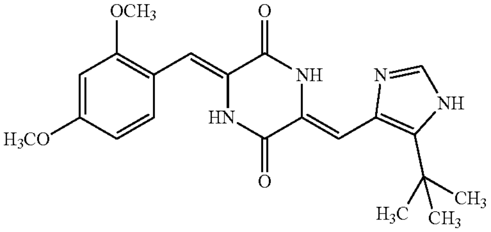 [SMILES: COc1ccc(/C=c2\[nH]c(=O)/c(=C/c3nc[nH]c3C(C)(C)C)[nH]c2=O)c(OC)c1] | KPU-12 |
| 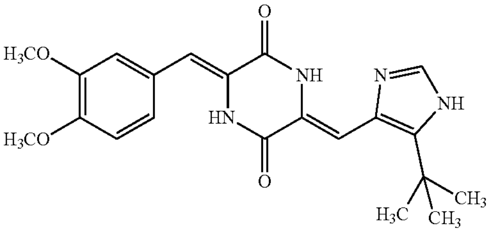 [SMILES: COc1ccc(/C=c2\[nH]c(=O)/c(=C/c3nc[nH]c3C(C)(C)C)[nH]c2=O)cc1OC] | KPU-13 |
| 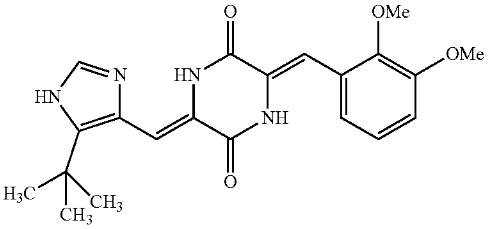 | KPU-14, tBu-delta-PLH-2,3-diOMe |
| 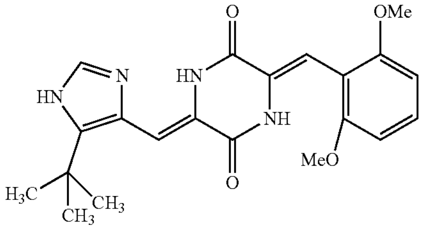 [SMILES: COc1cccc(OC)c1/C=c1\[nH]c(=O)/c(=C/c2nc[nH]c2C(C)(C)C)[nH]c1=O] | KPU-15, tBu-delta-PLH-2,6-diOMe |
| 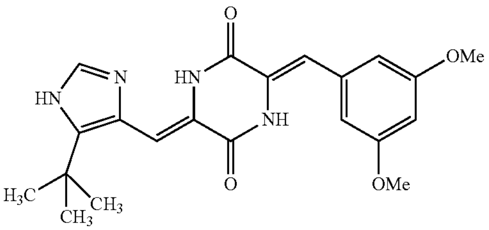 [SMILES: COc1cc(/C=c2\[nH]c(=O)/c(=C/c3nc[nH]c3C(C)(C)C)[nH]c2=O)cc(OC)c1] | KPU-16, tBu-delta-3,5-diOMe |

TABLE A-continued
| Phenylahistin and dehydrophenylahistin derivatives | |
|---|---|
| Structure | Chemical name |
| 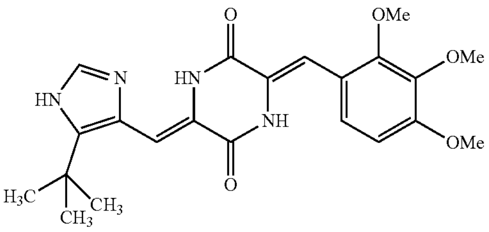 [SMILES: COc1ccc(/C=c2\[nH]c(=O)/c(=C/c3nc[nH]c3C(C)(C)C)[nH]c2=O)c(OC)c1OC] | KPU-17, tBu-delta-PLH-2,3,4-triOMe |
| 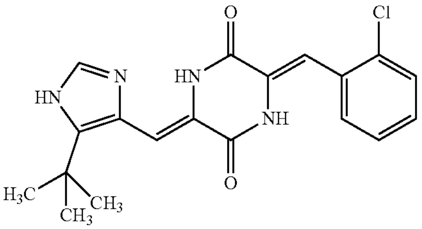 [SMILES: CC(C)(C)c1[nH]cnc1/C=c1\[nH]c(=O)/c(=C/c2ccccc2Cl)[nH]c1=O] | KPU-18, tBu-delta-PLH-o-Cl |
| 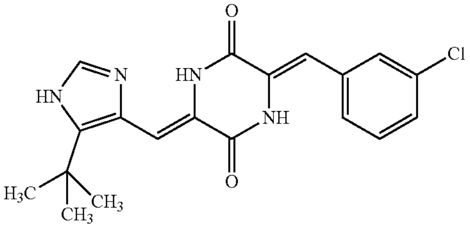 | KPU-19, tBu-delta-PLH-m-Cl |
| 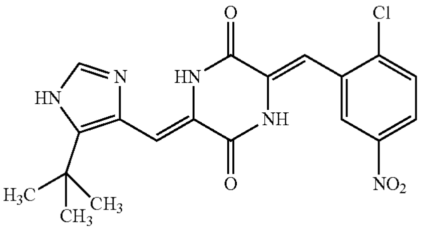 [SMILES: CC(C)(C)c1[nH]cnc1/C=c1\[nH]c(=O)/c(=C/c2cc([N+](=O)[O-])ccc2Cl)[nH]c1=O] | KPU-21, tBu-delta-PLH-2-Cl-5-NO2 |
| 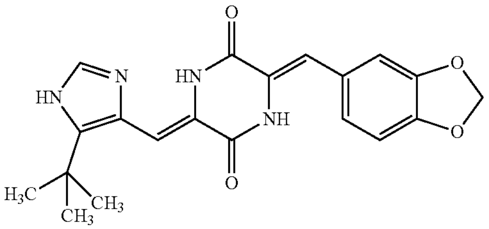 [SMILES: CC(C)(C)c1[nH]cnc1/C=c1\[nH]c(=O)/c(=C/c2ccc3c(c2)OCO3)[nH]c1=O] | KPU-22, tBu-delta-PLH-3,4-methylene-dioxy |
| 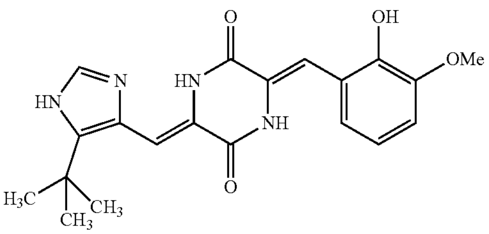 [SMILES: COc1cccc(/C=c2\[nH]c(=O)/c(=C/c3nc[nH]c3C(C)(C)C)[nH]c2=O)c1O] | KPU-23, tBu-delta-PLH-2-OH-3-OMe (o-vanillin) |

TABLE A-continued
| Phenylahistin and dehydrophenylahistin derivatives | |
|---|---|
| Structure | Chemical name |
| 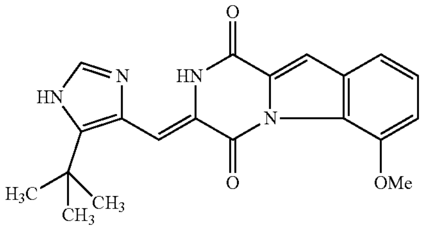 [SMILES: COc1cccc2cc3c(=O)[nH]/c(=C\c4nc[nH]c4C(C)(C)C)c(=O)n3c12] | KPU-24, tBu-delta-PLH-cyclized-3-MeO |
| 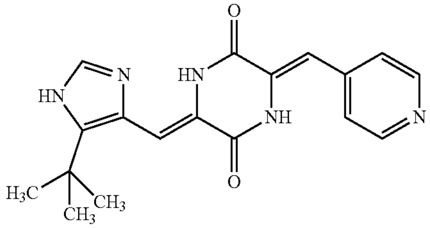 [SMILES: CC(C)(C)c1[nH]cnc1/C=c1\[nH]c(=O)/c(=C/c2ccncc2)[nH]c1=O] | KPU-25, tBu-delta-PLH-4-pyridyl |
| 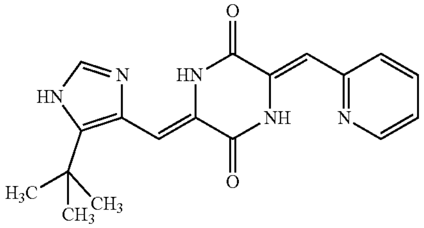 | KPU-28, tBu-delta-PLH-2-pyridyl |
| 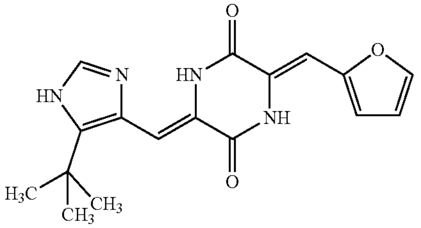 [SMILES: CC(C)(C)c1[nH]cnc1/C=c1\[nH]c(=O)/c(=C/c2ccco2)[nH]c1=O] | KPU-26, tBu-delta-PLH-2-furyl |
| 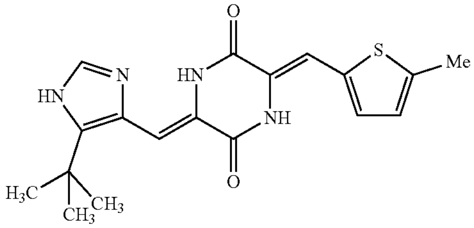 [SMILES: Cc1ccc(/C=c2\[nH]c(=O)/c(=C/c3nc[nH]c3C(C)(C)C)[nH]c2=O)s1] | KPU-27, tBu-delta-PLH-5-Me-2-thienyl |
| 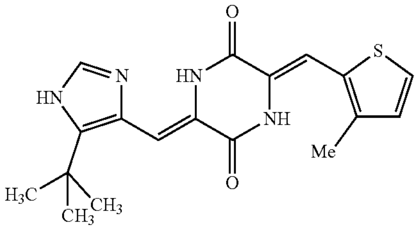 [SMILES: Cc1ccsc1/C=c1\[nH]c(=O)/c(=C/c2nc[nH]c2C(C)(C)C)[nH]c1=O] | KPU-29, tBu-delta-PLH-3-Me-2-thienyl |

TABLE A-continued
| Phenylahistin and dehydrophenylahistin derivatives | |
|---|---|
| Structure | Chemical name |
| 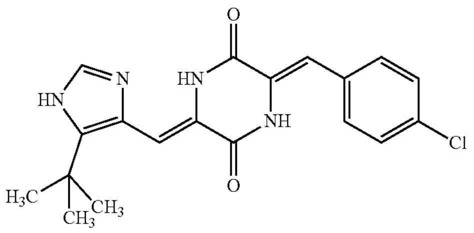 +TFA | KPU-20; t-butyl-delta-PLH-p-Cl + TFA salt (MW: 484) |
| 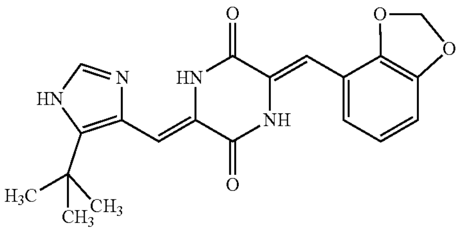 [SMILES: CC(C)(C)c1[nH]cnc1/C=c1\[nH]c(=O)/c(=C/c2cccc3c2OCO3)[nH]c1=O] | KPU-30, tBu-delta-PLH-2,3-methylendioxy; TFA salt (MW: 494.42) |
| 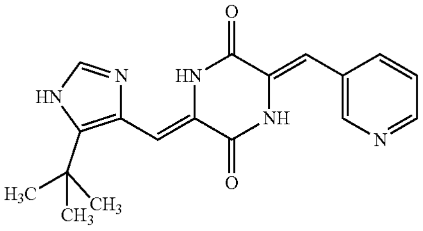 [SMILES: CC(C)(C)c1[nH]cnc1/C=c1\[nH]c(=O)/c(=C/c2cccnc2)[nH]c1=O] | KPU-31, tBu-delta-PLH-3-pyridyl; 2TFA salt (MW 565.42) |
| 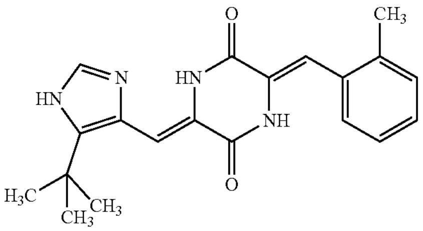 | KPU-32, tBu-delta-PLH-o-Me; TFA salt (MW: 464.44) |
| 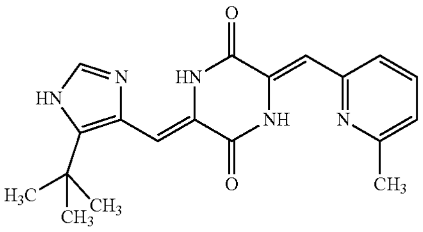 [SMILES: Cc1cccc(/C=c2\[nH]c(=O)/c(=C/c3nc[nH]c3C(C)(C)C)[nH]c2=O)n1] | KPU-33, tBu-delta-PLH-3-Me-2-pyridyl; 2TFA salt (MW: 579.45) |
| 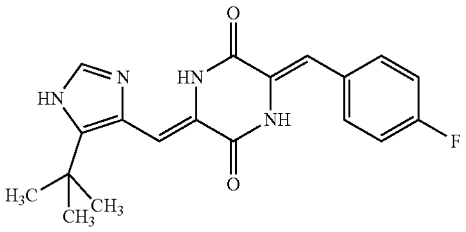 [SMILES: CC(C)(C)c1[nH]cnc1/C=c1\[nH]c(=O)/c(=C/c2ccc(F)cc2)[nH]c1=O] | KPU-34, tBu-delta-PLH-4-F; TFA salt (MW: 468.40) |

TABLE A-continued
| Phenylahistin and dehydrophenylahistin derivatives | |
|---|---|
| Structure | Chemical name |
| 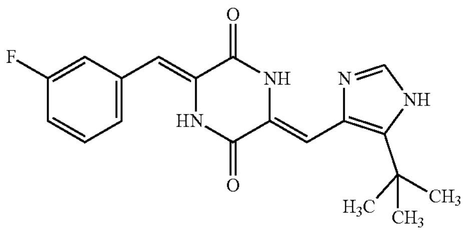 [SMILES: CC(C)(C)c1[nH]cnc1/C=c1\[nH]c(=O)/c(=C/c2cccc(F)c2)[nH]c1=O] | KPU-35, tBu-delta-PLH-m-F; TFA salt (MW: 468.40) |
| 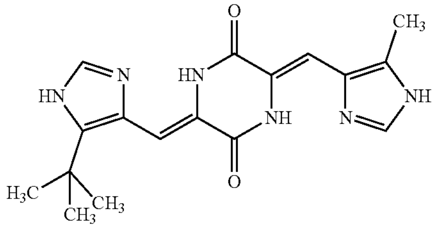 [SMILES: Cc1[nH]cnc1/C=c1\[nH]c(=O)/c(=C/c2nc[nH]c2C(C)(C)C)[nH]c1=O] | KPU-36, tBu-delta-PLH-5-Me-4-im; 2TFA salt (MW: 584.47) |
| 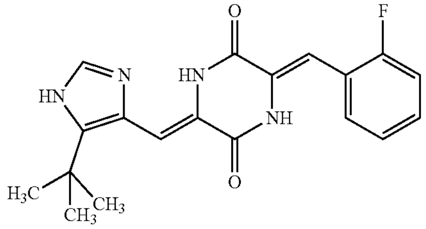 | KPU-37, tBu-delta-PLH-o-F, TFA salt (MW: 468.40) |
| 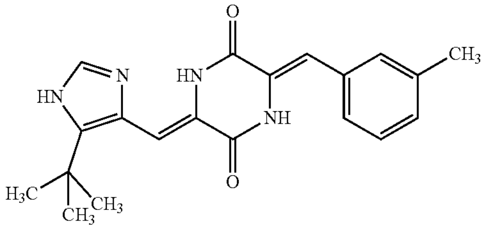 [SMILES: Cc1cccc(/C=c2\[nH]c(=O)/c(=C/c3nc[nH]c3C(C)(C)C)[nH]c2=O)c1] | KPU-38, tBu-delta-PLH-m-Me; TFA salt (MW: 464.44) |
| 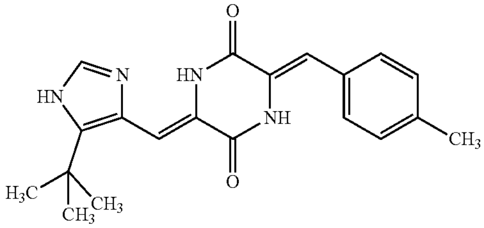 [SMILES: Cc1ccc(/C=c2\[nH]c(=O)/c(=C/c3nc[nH]c3C(C)(C)C)[nH]c2=O)cc1] | KPU-39, tBu-delta-PLH-p-Me; TFA Salt (MW: 464.44) |
| 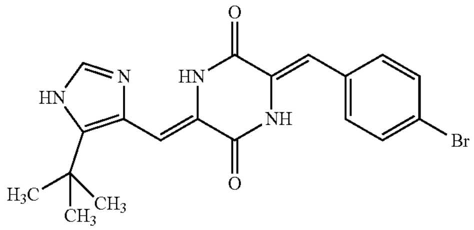 [SMILES: CC(C)(C)c1[nH]cnc1/C=c1\[nH]c(=O)/c(=C/c2ccc(Br)cc2)[nH]c1=O] | KPU-40, tBu-delta-PLH-p-Br; TFA Salt (MW: 529.31) |

TABLE A-continued
| Phenylahistin and dehydrophenylahistin derivatives | |
|---|---|
| Structure | Chemical name |
| 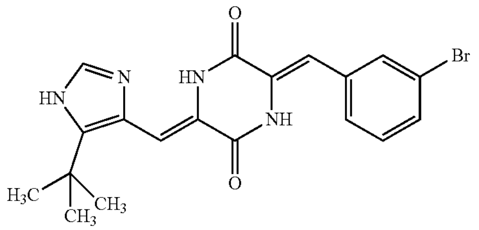 [SMILES: CC(C)(C)c1[nH]cnc1/C=c1\[nH]c(=O)/c(=C/c2cccc(Br)c2)[nH]c1=O] | KPU-41, tBu-delta-PLH-m-Br; TFA Salt (MW: 529.31) |
| 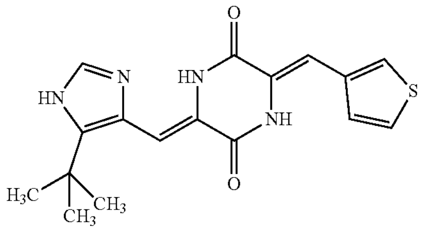 [SMILES: CC(C)(C)c1[nH]cnc1/C=c1\[nH]c(=O)/c(=C/c2ccsc2)[nH]c1=O] | KPU-42, tBu-delta-PLH-3-thienyl; TFA Salt (MW: 456.44) |
| 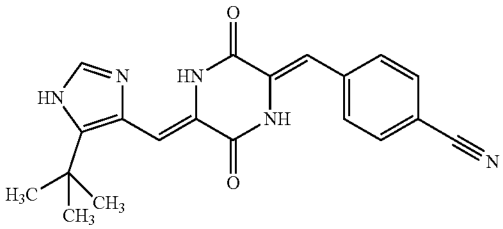 [SMILES: CC(C)(C)c1[nH]cnc1/C=c1\[nH]c(=O)/c(=C/c2ccc(C#N)cc2)[nH]c1=O] | KPU-43, tBu-delta-PLH-p-CN; TFA Salt (MW: 475.42) |
| 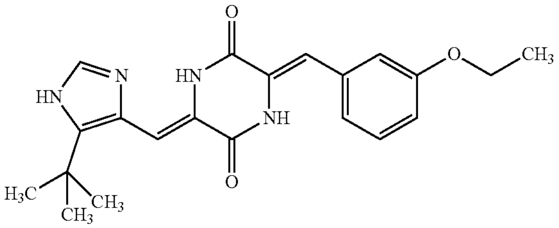 [SMILES: CCOc1cccc(/C=c2\[nH]c(=O)/c(=C/c3nc[nH]c3C(C)(C)C)[nH]c2=O)c1] | KPU-44, tBu-delta-PLH-m-EtO; TFA Salt (MW: 494.46) |
| 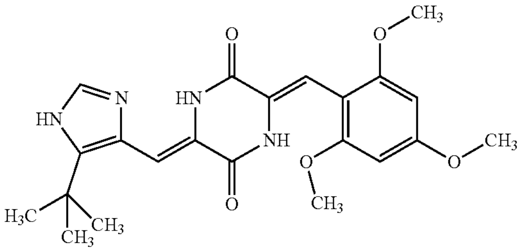 [SMILES: COc1cc(OC)c(/C=c2\[nH]c(=O)/c(=C/c3nc[nH]c3C(C)(C)C)[nH]c2=O)c(OC)c1] | KPU-45, tBu-delta-PLH-2,4,6-TriOMe; TFA Salt (MW: 540.49) |
| 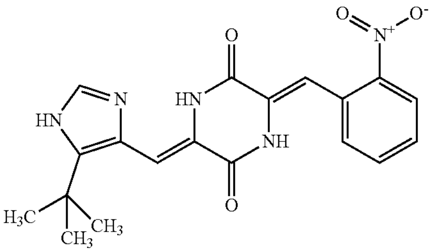 [SMILES: CC(C)(C)c1[nH]cnc1/C=c1\[nH]c(=O)/c(=C/c2ccccc2[N+](=O)[O-])[nH]c1=O] | KPU-46, tBu-delta-PLH-o-NO2; TFA Salt (MW: 495.41) |

TABLE A-continued
| Phenylahistin and dehydrophenylahistin derivatives | |
|---|---|
| Structure | Chemical name |
| 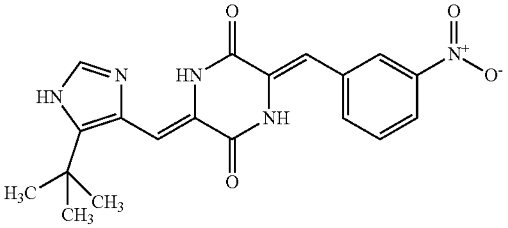 [SMILES: CC(C)(C)c1[nH]cnc1/C=c1\[nH]c(=O)/c(=C/c2cccc([N+](=O)[O-])c2)[nH]c1=O] | KPU-47, tBu-delta-PLH-m-NO2; TFA Salt (MW: 495.41) |
| 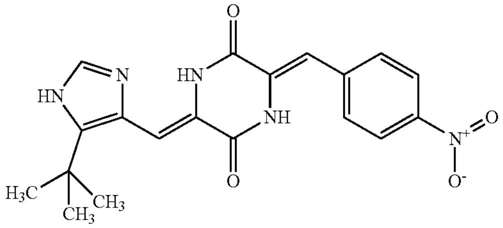 [SMILES: CC(C)(C)c1[nH]cnc1/C=c1\[nH]c(=O)/c(=C/c2ccc([N+](=O)[O-])cc2)[nH]c1=O] | KPU-48, tBu-delta-PLH-p-NO2; TFA Salt (MW: 495.41) |
| 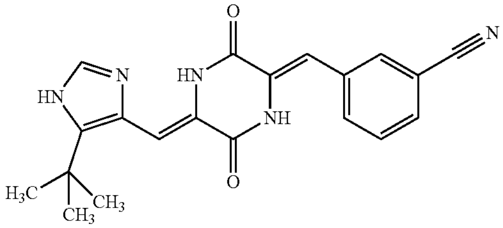 [SMILES: CC(C)(C)c1[nH]cnc1/C=c1\[nH]c(=O)/c(=C/c2cccc(C#N)c2)[nH]c1=O] | KPU-49, tBu-delta-PLH-m-CN; TFA Salt (MW: 475.42) |
| 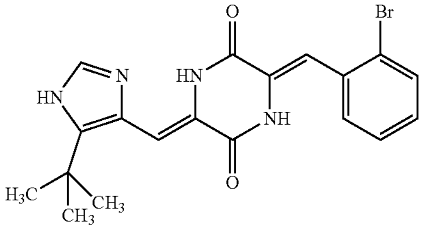 | KPU-50, tBu-delta-PLH-o-Br; TFA Salt (MW: 529.31) |
| 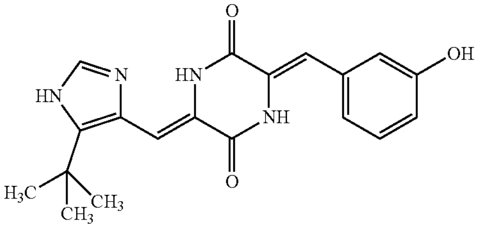 [SMILES: CC(C)(C)c1[nH]cnc1/C=c1\[nH]c(=O)/c(=C/c2cccc(O)c2)[nH]c1=O] | KPU-51, tBu-delta-PLH-m-OH; TFA Salt (MW: 466.41) |
| 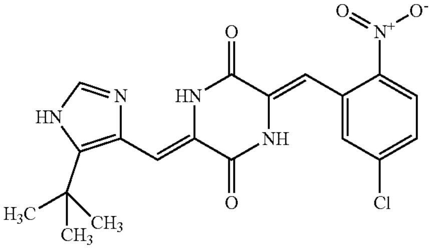 [SMILES: CC(C)(C)c1[nH]cnc1/C=c1\[nH]c(=O)/c(=C/c2cc(Cl)ccc2[N+](=O)[O-])[nH]c1=O] | KPU-52, tBu-delta-PLH-2-NO2-5-Cl; TFA salt (MW: 529.85) |

TABLE A-continued
| Phenylahistin and dehydrophenylahistin derivatives | |
|---|---|
| Structure | Chemical name |
| 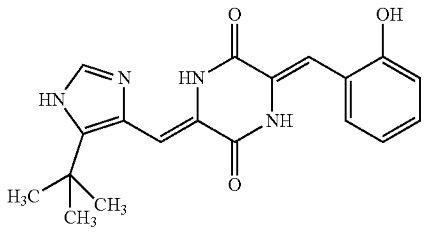 [SMILES: CC(C)(C)c1[nH]cnc1/C=c1\[nH]c(=O)/c(=C/c2ccccc2O)[nH]c1=O] | KPU-53, tBu-delta-PLH-o-OH; TFA Salt (MW: 466.41) |
| 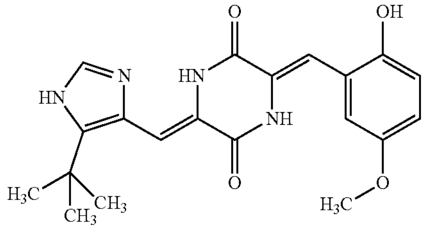 [SMILES: COc1ccc(O)c(/C=c2\[nH]c(=O)/c(=C/c3nc[nH]c3C(C)(C)C)[nH]c2=O)c1] | KPU-54, tBu-delta-PLH-2-OH-5-OMe; TFA Salt (MW: 496.44) |
| 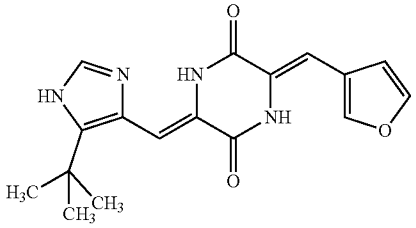 [SMILES: CC(C)(C)c1[nH]cnc1/C=c1\[nH]c(=O)/c(=C/c2ccoc2)[nH]c1=O] | KPU-55, tBu-delta-PLH-3-furanyl; TFA Salt (MW: 440.37) |
| 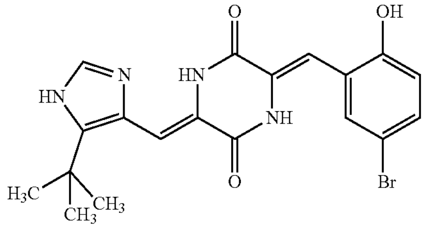 [SMILES: CC(C)(C)c1[nH]cnc1/C=c1\[nH]c(=O)/c(=C/c2cc(Br)ccc2O)[nH]c1=O] | KPU-56, tBu-delta-PLH-2-OH-5-Br; TFA Salt (MW: 545.31) |
| 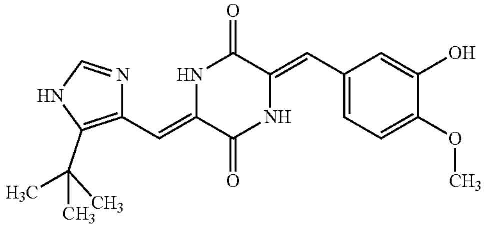 [SMILES: COc1ccc(/C=c2\[nH]c(=O)/c(=C/c3nc[nH]c3C(C)(C)C)[nH]c2=O)cc1O] | KPU-57, tBu-delta-PLH-3-OH-4-OMe; TFA Salt (MW: 496.44) |
| 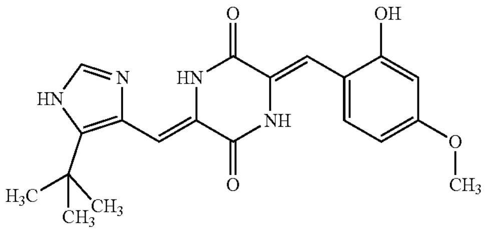 [SMILES: COc1ccc(/C=c2\[nH]c(=O)/c(=C/c3nc[nH]c3C(C)(C)C)[nH]c2=O)c(O)c1] | KPU-58, tBu-delta-PLH-2-OH-4-OMe; TFA Salt (MW: 496.44) |

TABLE A-continued
| Phenylahistin and dehydrophenylahistin derivatives | |
|---|---|
| Structure | Chemical name |
| 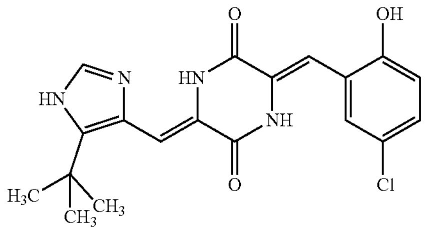 | KPU-59, tBu-delta-PLH-2-OH-5-Cl; TFA Salt (MW: 500.86) |
| 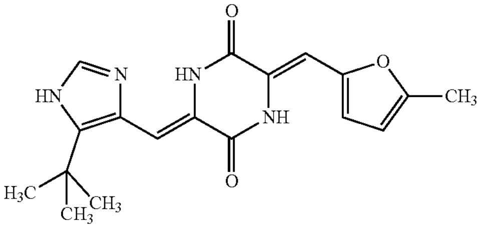 [SMILES: Cc1ccc(/C=c2\[nH]c(=O)/c(=C/c3nc[nH]c3C(C)(C)C)[nH]c2=O)o1] | KPU-60, tBu-delta-PLH-5-Me-2-furanyl; TFA Salt (MW: 454.40) |
| 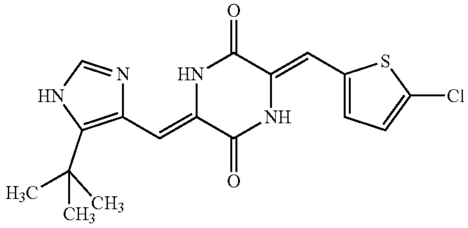 [SMILES: CC(C)(C)c1[nH]cnc1/C=c1\[nH]c(=O)/c(=C/c2ccc(Cl)s2)[nH]c1=O] | KPU-61, tBu-delta-PLH-5-Cl-2-thionyl; TFA Salt (MW: 490.88) |
| 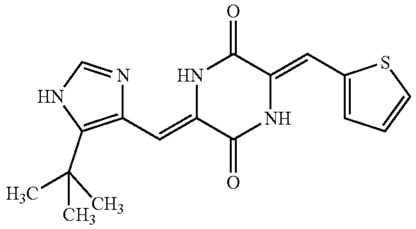 [SMILES: CC(C)(C)c1[nH]cnc1/C=c1\[nH]c(=O)/c(=C/c2cccs2)[nH]c1=O] | KPU-62, tBu-delta-PLH-2-thionyl; TFA Salt (MW: 456.44) |
| 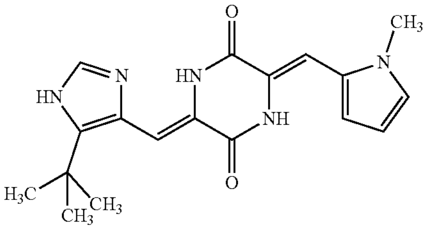 [SMILES: Cn1cccc1/C=c1\[nH]c(=O)/c(=C/c2nc[nH]c2C(C)(C)C)[nH]c1=O] | KPU-63, tBu-delta-PLH-N-Me-2-pyrrole; TFA Salt (MW: 453.42) |
| 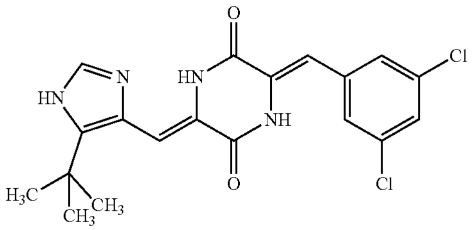 [SMILES: CC(C)(C)c1[nH]cnc1/C=c1\[nH]c(=O)/c(=C/c2cc(Cl)cc(Cl)c2)[nH]c1=O] | KPU-64, tBu-delta-PLH-3,5-diCl; TFA Salt (MW 519.30) |

TABLE A-continued
| Phenylahistin and dehydrophenylahistin derivatives | |
|---|---|
| Structure | Chemical name |
| 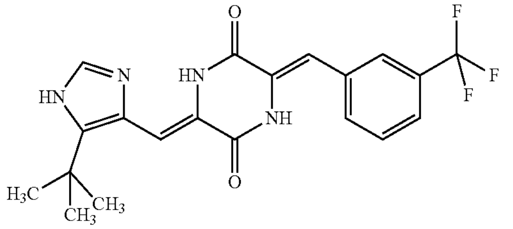 [SMILES: CC(C)(C)c1[nH]cnc1/C=c1\[nH]c(=O)/c(=C/c2cccc(C(F)(F)F)c2)[nH]c1=O] | KPU-65, tBu-delta-PLH-m-CF3; TFA Salt (MW 518.41) |
| 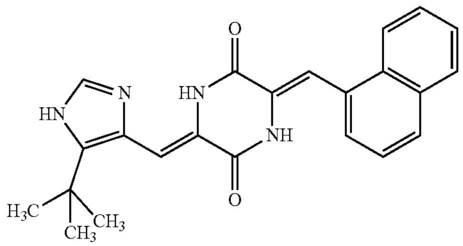 [SMILES: CC(C)(C)c1[nH]cnc1/C=c1\[nH]c(=O)/c(=C/c2cccc3ccccc23)[nH]c1=O] | KPU-66, tBu-delta-PLH-1-napthalene; TFA Salt (MW 500.47) |
| 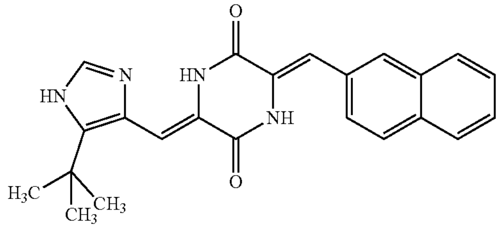 [SMILES: CC(C)(C)c1[nH]cnc1/C=c1\[nH]c(=O)/c(=C/c2ccc3ccccc3c2)[nH]c1=O] | KPU-67, tBu-delta-PLH-2-napthalene; TFA Salt (MW 500.47) |
| 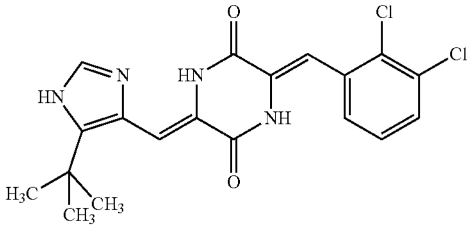 [SMILES: CC(C)(C)c1[nH]cnc1/C=c1\[nH]c(=O)/c(=C/c2cccc(Cl)c2Cl)[nH]c1=O] | KPU-68, tBu-delta-PLH-2,3-diCl; TFA Salt (MW 519.30) |
| 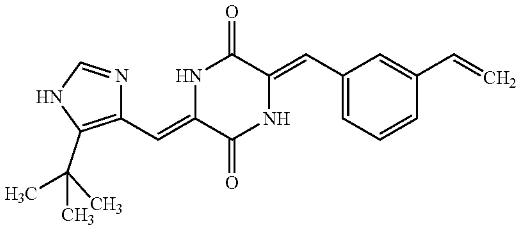 [SMILES: C=Cc1cccc(/C=c2\[nH]c(=O)/c(=C/c3nc[nH]c3C(C)(C)C)[nH]c2=O)c1] | KPU-69, tBu-delta-PLH-m-Vinyl; TFA Salt (MW 476.45) |
| 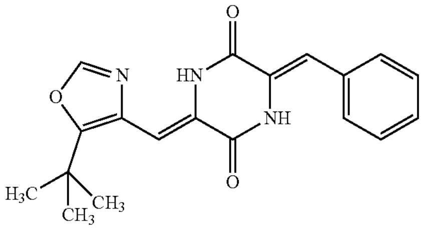 | KPU-70, tBu-delta-PLH-oxazole; TFA Salt (MW 451.40) |

TABLE A-continued
| Phenylahistin and dehydrophenylahistin derivatives | |
|---|---|
| Structure | Chemical name |
| 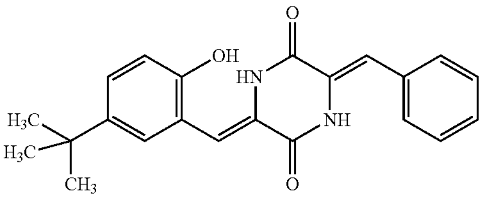 [SMILES: CC(C)(C)c1ccc(O)c(/C=c2\[nH]c(=O)/c(=C/c3ccccc3)[nH]c2=O)c1] | KPU-71, tBu-delta-PLH-2-Hydroxybenzyl; TFA Salt (MW 495.91) |
| 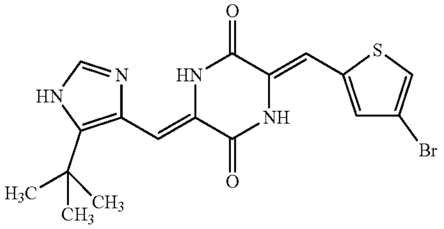 [SMILES: CC(C)(C)c1[nH]cnc1/C=c1\[nH]c(=O)/c(=C/c2cc(Br)cs2)[nH]c1=O] | KPU-72, tBu-delta-PLH-4-Br-2-thionyl; TFA Salt (MW 484.49) |
| 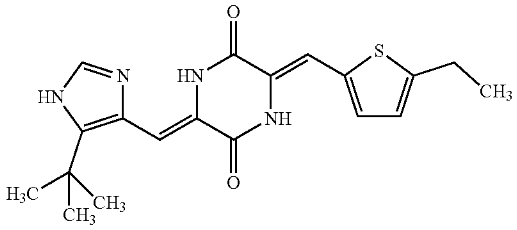 | KPU-73, tBu-delta-PLH-5-Et-2-thionyl; TFA Salt (MW 535.34) |
| 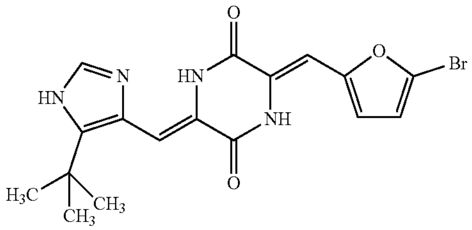 [SMILES: CC(C)(C)c1[nH]cnc1/C=c1\[nH]c(=O)/c(=C/c2ccc(Br)o2)[nH]c1=O] | KPU-74, tBu-delta-PLH-5-Br-2-furyl; TFA Salt (MW 519.27) |
| 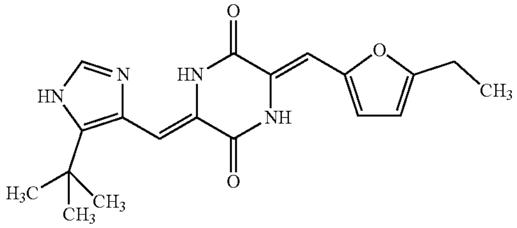 [SMILES: CCc1ccc(/C=c2\[nH]c(=O)/c(=C/c3nc[nH]c3C(C)(C)C)[nH]c2=O)o1] | KPU-75, tBu-delta-PLH-5-Et-2-furyl; TFA Salt (MW 468.43) |
| 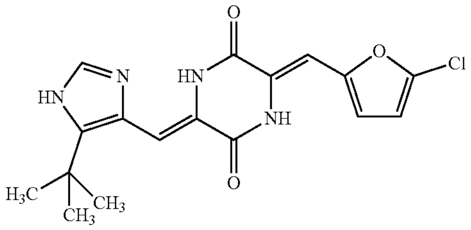 [SMILES: CC(C)(C)c1[nH]cnc1/C=c1\[nH]c(=O)/c(=C/c2ccc(Cl)o2)[nH]c1=O] | KPU-76, tBu-delta-PLH-5-Cl-2-furyl; TFA Salt (MW 474.82) |

TABLE A-continued
| Phenylahistin and dehydrophenylahistin derivatives | |
|---|---|
| Structure | Chemical name |
| 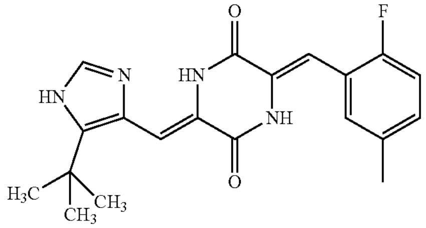 [SMILES: Cc1ccc(F)c(/C=c2\[nH]c(=O)/c(=C/c3nc[nH]c3C(C)(C)C)[nH]c2=O)c1] | KPU-77, tBu-delta-PLH-2-F-5-I; TFA Salt (MW 594.30) |
| 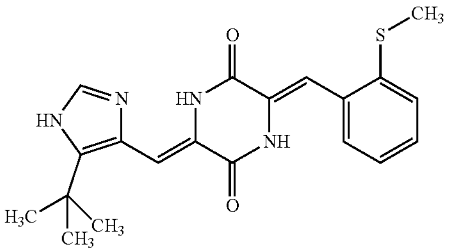 [SMILES: CSc1ccccc1/C=c1\[nH]c(=O)/c(=C/c2nc[nH]c2C(C)(C)C)[nH]c1=O] | KPU-79, tBu-delta-PLH-2-(Methylthio); TFA Salt (MW 496.50) |
| 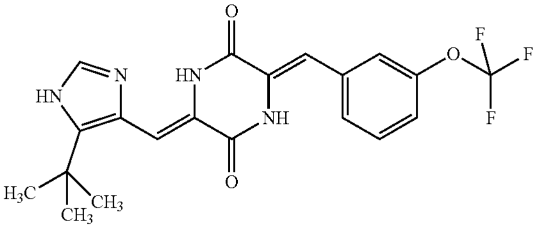 | KPU-80, tBu-delta-PLH-m-OCF3; TFA Salt (MW) |
| 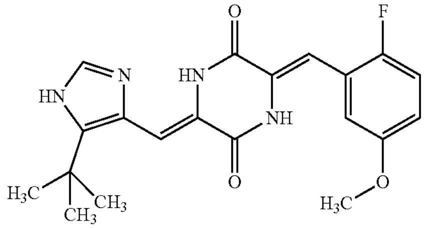 [SMILES: COc1ccc(F)c(/C=c2\[nH]c(=O)/c(=C/c3nc[nH]c3C(C)(C)C)[nH]c2=O)c1] | KPU-81, tBu-delta-PLH-2-F5-OMe; TFA Salt (MW) |
| 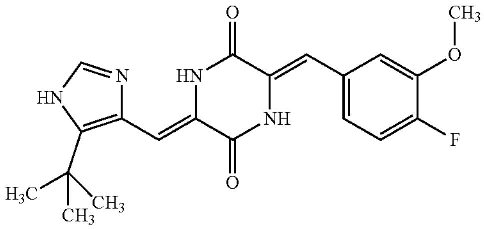 [SMILES: COc1cc(/C=c2\[nH]c(=O)/c(=C/c3nc[nH]c3C(C)(C)C)[nH]c2=O)ccc1F] | KPU-82, tBu-delta-PLH-4-F-3-OMe; TFA Salt (MW) |
| 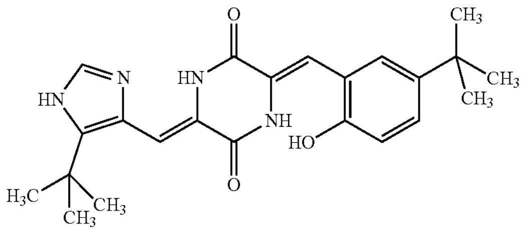 [SMILES: CC(C)(C)c1ccc(O)c(/C=c2\[nH]c(=O)/c(=C/c3nc[nH]c3C(C)(C)C)[nH]c2=O)c1] | KPU-83, tBu-delta-PLH-2-OH-5-tBU; TFA Salt (MW) |

TABLE A-continued
| Phenylahistin and dehydrophenylahistin derivatives | |
|---|---|
| Structure | Chemical name |
| 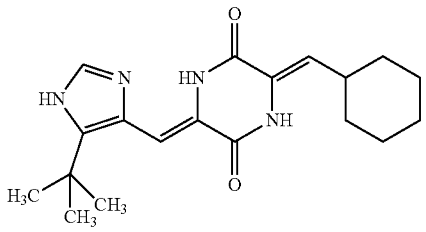 [SMILES: CC(C)(C)c1[nH]cnc1/C=c1\[nH]c(=O)/c(=C/C2CCCCC2)[nH]c1=O] | KPU-84, tBu-delta-PLH-cyclohexane; TFA Salt (MW) |
| 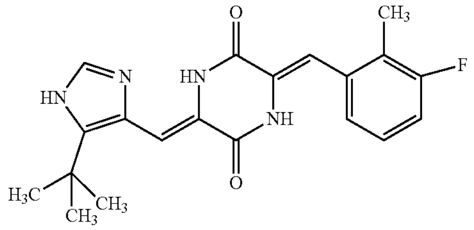 [SMILES: Cc1c(F)cccc1/C=c1\[nH]c(=O)/c(=C/c2nc[nH]c2C(C)(C)C)[nH]c1=O] | KPU-86, tBu-delta-PLH-2-Me-3-F; TFA Salt (MW) |
| 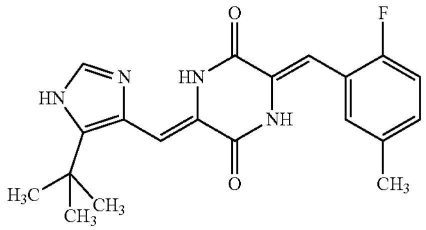 [SMILES: Cc1ccc(F)c(/C=c2\[nH]c(=O)/c(=C/c3nc[nH]c3C(C)(C)C)[nH]c2=O)c1] | KPU-87, tBu-delta-PLH-2-F-5-Me; TFA Salt (MW) |
| 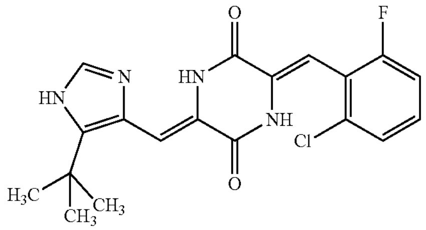 [SMILES: CC(C)(C)c1[nH]cnc1/C=c1\[nH]c(=O)/c(=C/c2c(F)cccc2Cl)[nH]c1=O] | KPU-88, tBu-delta-PLH-2-Cl-6-F; TFA Salt (MW) |
| 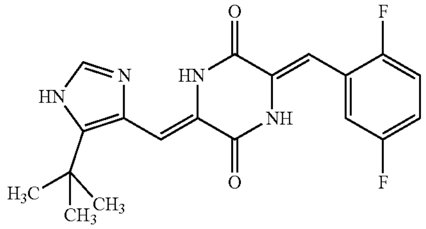 | KPU-89, tBu-delta-PLH-2,5-di-F; TFA Salt (MW) |
| 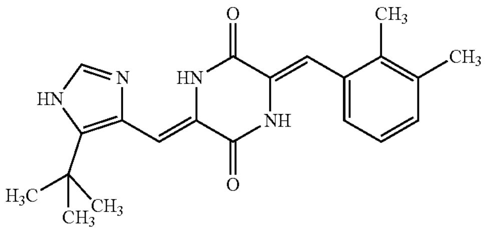 | KPU-90, tBu-delta-PLH-2,3-di-Me; TFA Salt (MW) |

TABLE A-continued
| Phenylahistin and dehydrophenylahistin derivatives | |
|---|---|
| Structure | Chemical name |
| 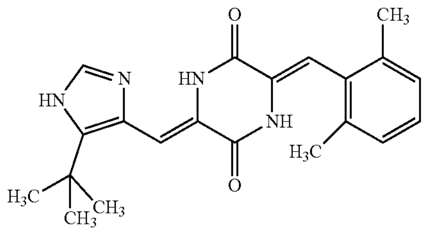 [SMILES: Cc1cccc(C)c1/C=c1\[nH]c(=O)/c(=C/c2nc[nH]c2C(C)(C)C)[nH]c1=O] | KPU-91, tBu-delta-PLH-2,6-di-Me; TFA Salt (MW) |
| 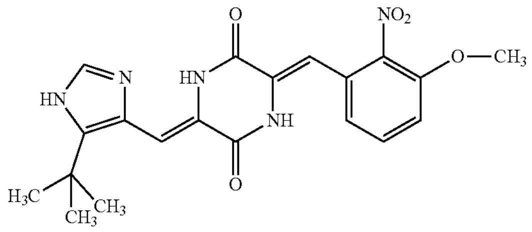 [SMILES: COc1cccc(/C=c2\[nH]c(=O)/c(=C/c3nc[nH]c3C(C)(C)C)[nH]c2=O)c1[N+](=O)[O-]] | KPU-92, tBu-delta-PLH-2-NO2-3-OMe; TFA Salt (MW) |
| 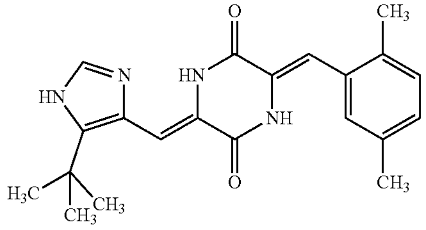 | KPU-93, tBu-delta-PLH-2,5-diMe; TFA Salt (MW) |
| 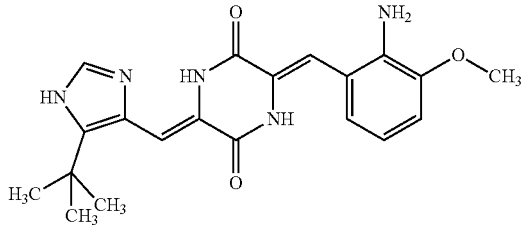 [SMILES: COc1cccc(/C=c2\[nH]c(=O)/c(=C/c3nc[nH]c3C(C)(C)C)[nH]c2=O)c1N] | KPU-94, tBu-delta-PLH-2-NH2-3-OMe; TFA Salt |
| 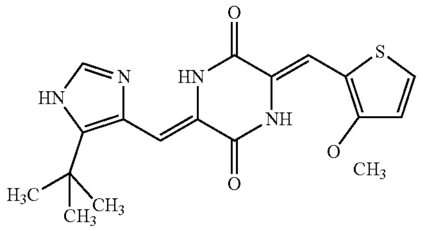 | KPU-95, tBu-delta-PLH-3-OMe-2-furyl; TFA Salt |
| 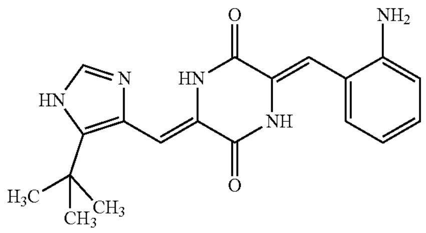 | KPU-96, tBu-delta-PLH-2-NH2; TFA Salt |

TABLE A-continued
| Phenylahistin and dehydrophenylahistin derivatives | |
|---|---|
| Structure | Chemical name |
| 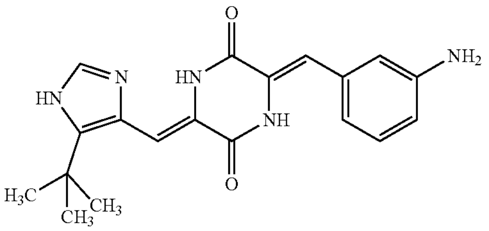 | KPU-97, tBu-delta-PLH-m-NH2; TFA Salt |
| 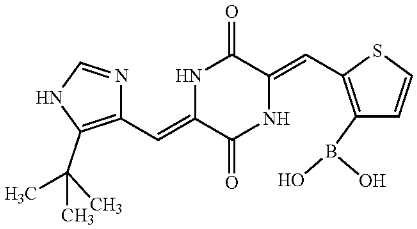 [SMILES: CC(C)(C)c1[nH]cnc1/C=c1\[nH]c(=O)/c(=C/c2sccc2B(O)O)[nH]c1=O] | KPU-98, tBu-delta-PLH-3-B(OH)2-2-thienyl; TFA Salt |
| 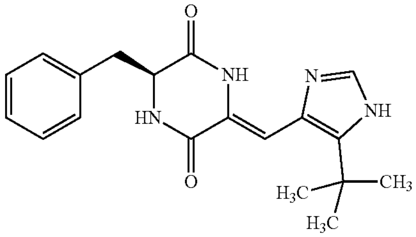 [SMILES: CC(C)(C)c1[nH]cnc1/C=C1\NC(=O)[C@H](Cc2ccccc2)NC1=O] | (−)-tBu-PLH |
TABLE B
| Additional dehydrophenylahistin derivatives | |
|---|---|
| Structure | Chemical name |
| 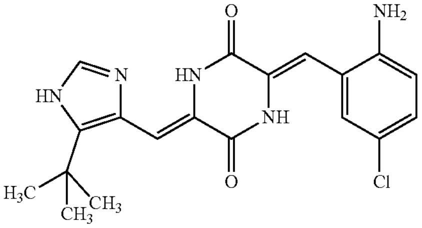 | KPU-99; tBu-delta-PLH-5-Cl-2-NH2; TFA Salt |
| 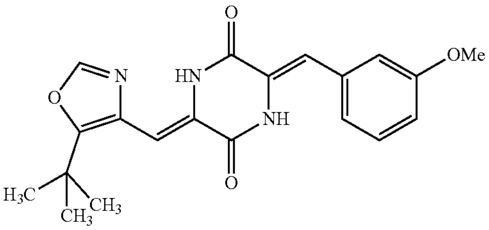 [SMILES: COc1cccc(/C=c2\[nH]c(=O)/c(=C/c3ncoc3C(C)(C)C)[nH]c2=O)c1] | KPU-201; tBu-Oxadelta-PLH-m-OMe |

TABLE B-continued
| Additional dehydrophenylahistin derivatives | |
|---|---|
| Structure | Chemical name |
| 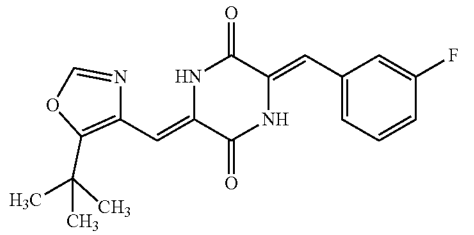 [SMILES: CC(C)(C)c1ocnc1/C=c1\[nH]c(=O)/c(=C/c2cccc(F)c2)[nH]c1=O] | KPU-202; tBu-Oxadelta-PLH-m-F |
| 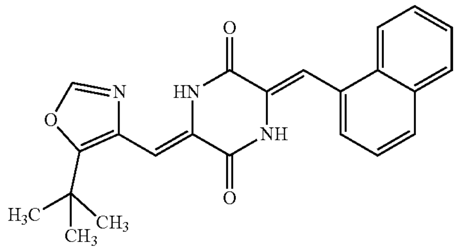 [SMILES: CC(C)(C)c1ocnc1/C=c1\[nH]c(=O)/c(=C/c2cccc3ccccc23)[nH]c1=O] | KPU-203; tBu-Oxadelta-PLH-1-naphth |
| 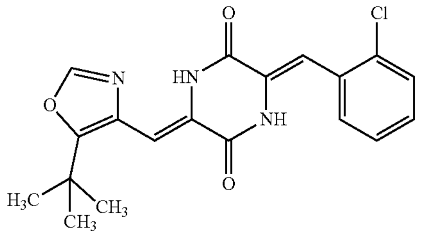 [SMILES: CC(C)(C)c1ocnc1/C=c1\[nH]c(=O)/c(=C/c2ccccc2Cl)[nH]c1=O] | KPU-204; tBu-Oxadelta-PLH-2-Cl |
| 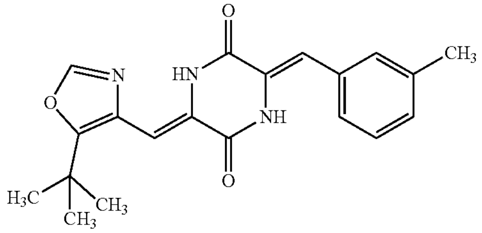 [SMILES: Cc1cccc(/C=c2\[nH]c(=O)/c(=C/c3ncoc3C(C)(C)C)[nH]c2=O)c1] | KPU-205; tBu-Oxadelta-PLH-3-CH3 |
| 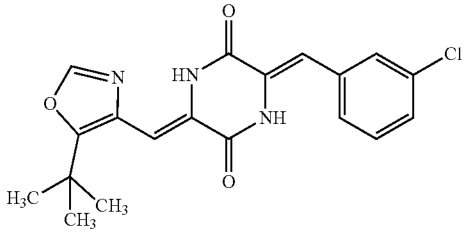 | KPU-206; tBu-Oxadelta-PLH-3-Cl |
| 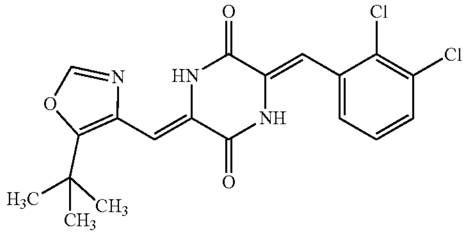 [SMILES: CC(C)(C)c1ocnc1/C=c1\[nH]c(=O)/c(=C/c2cccc(Cl)c2Cl)[nH]c1=O] | KPU-207; tBu-Oxadelta-PLH-2,3-diCl |

TABLE B-continued
| Additional dehydrophenylahistin derivatives | |
|---|---|
| Structure | Chemical name |
| 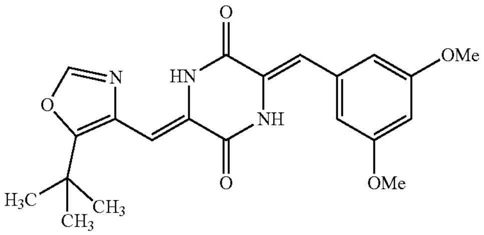 [SMILES: COc1cc(/C=c2\[nH]c(=O)/c(=C/c3ncoc3C(C)(C)C)[nH]c2=O)cc(OC)c1] | KPU-208; tBu-Oxadelta-PLH-3,5-diOMe |
| 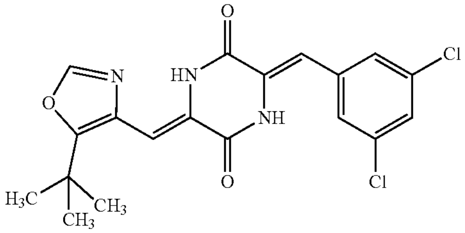 [SMILES: CC(C)(C)c1ocnc1/C=c1\[nH]c(=O)/c(=C/c2cc(Cl)cc(Cl)c2)[nH]c1=O] | KPU-209; tBu-Oxadelta-PLH-3,5-diCl |
| 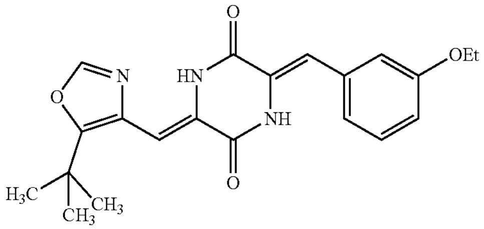 | KPU-210; tBu-Oxadelta-PLH-m-OEt |
| 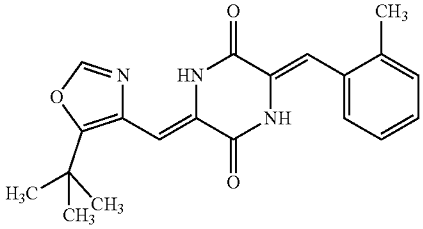 [SMILES: Cc1ccccc1/C=c1\[nH]c(=O)/c(=C/c2ncoc2C(C)(C)C)[nH]c1=O] | KPU-211; tBu-Oxadelta-PLH-o-Me |
| 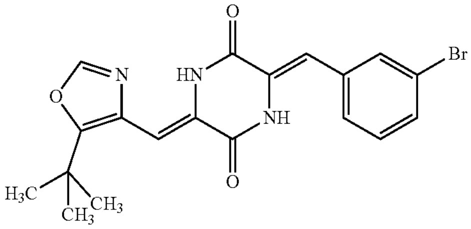 [SMILES: CC(C)(C)c1ocnc1/C=c1\[nH]c(=O)/c(=C/c2cccc(Br)c2)[nH]c1=O] | KPU-212; tBu-Oxadelta-PLH-3-Br |
| 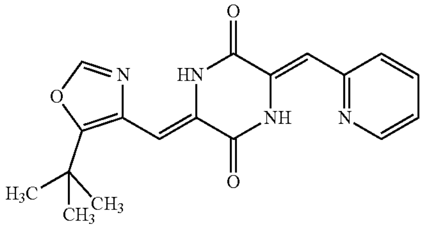 [SMILES: CC(C)(C)c1ocnc1/C=c1\[nH]c(=O)/c(=C/c2ccccn2)[nH]c1=O] | KPU-213; tBu-Oxadelta-PLH-2-Py |

TABLE B-continued
| Additional dehydrophenylahistin derivatives | |
|---|---|
| Structure | Chemical name |
| 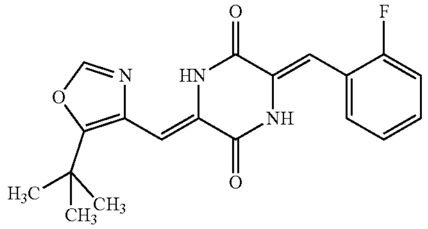 [SMILES: CC(C)(C)c1ocnc1/C=c1\[nH]c(=O)/c(=C/c2ccccc2F)[nH]c1=O] | KPU-214; tBu-Oxadelta-PLH-2-F |
| 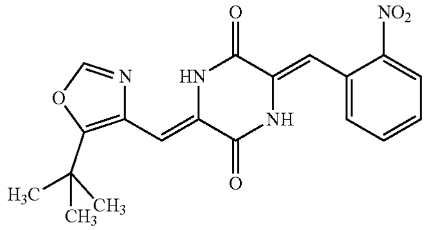 | KPU-215; tBu-Oxadelta-PLH-2-NO2 |
| 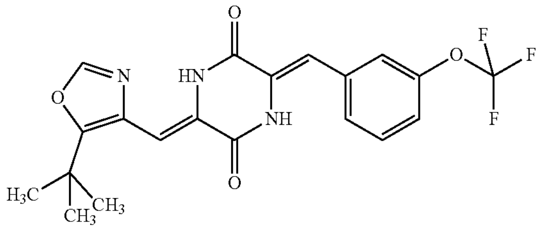 [SMILES: CC(C)(C)c1ocnc1/C=c1\[nH]c(=O)/c(=C/c2cccc(OC(F)(F)F)c2)[nH]c1=O] | KPU-216; tBu-Oxadelta-PLH-m-OCF3 |
| 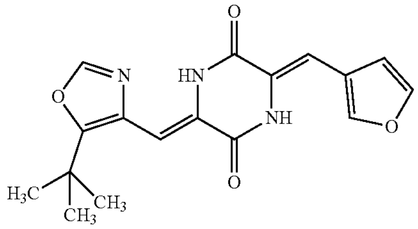 [SMILES: CC(C)(C)c1ocnc1/C=c1\[nH]c(=O)/c(=C/c2ccoc2)[nH]c1=O] | KPU-217; tBu-Oxadelta-PLH-3-furanyl |
| 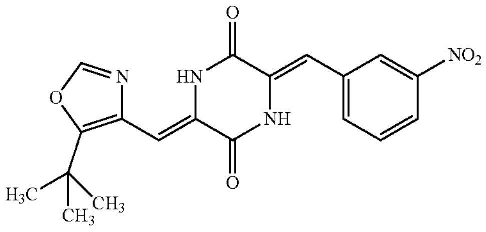 [SMILES: CC(C)(C)c1ocnc1/C=c1\[nH]c(=O)/c(=C/c2cccc([N+](=O)[O-])c2)[nH]c1=O] | KPU-218; tBu-Oxadelta-PLH-m-NO2 |
| 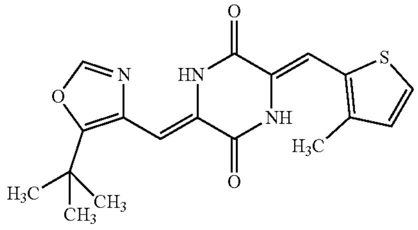 [SMILES: Cc1ccsc1/C=c1\[nH]c(=O)/c(=C/c2ncoc2C(C)(C)C)[nH]c1=O] | KPU-219; tBu-Oxadella-PLH-3-Me-2-thienyl |

TABLE B-continued
| Additional dehydrophenylahistin derivatives | |
|---|---|
| Structure | Chemical name |
| 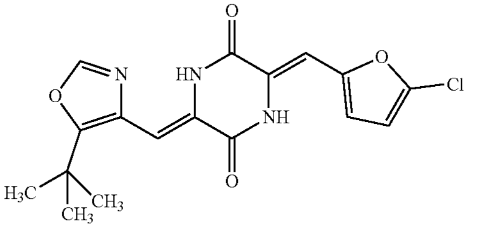 | KPU-220; tBu-Oxadelta-PLH-5-Cl-2-furyl |
| 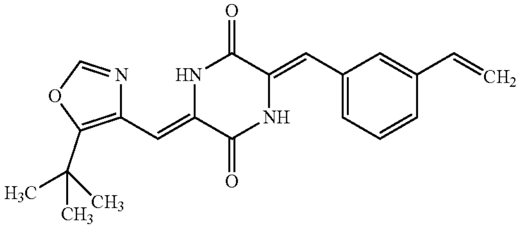 [SMILES: C=Cc1cccc(/C=c2\[nH]c(=O)/c(=C/c3ncoc3C(C)(C)C)[nH]c2=O)c1] | KPU-221; tBu-Oxadelta-PLH-m-vinyl |
| 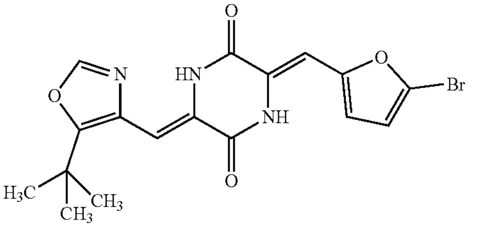 [SMILES: CC(C)(C)c1ocnc1/C=c1\[nH]c(=O)/c(=C/c2ccc(Br)o2)[nH]c1=O] | KPU-222; tBu-Oxadelta-PLH-5-Br-2-furyl |
| 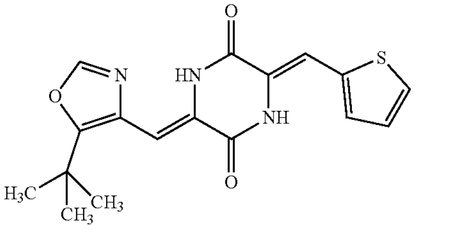 [SMILES: CC(C)(C)c1ocnc1/C=c1\[nH]c(=O)/c(=C/c2cccs2)[nH]c1=O] | KPU-223; tBu-Oxadelta-PLH-2-thienyl |
| 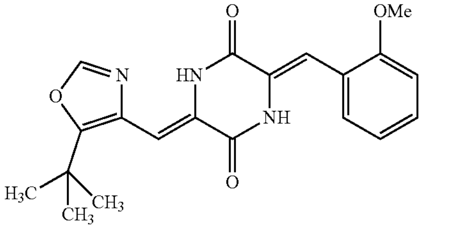 | KPU-224; tBu-Oxadelta-PLH-2-OMe |
| 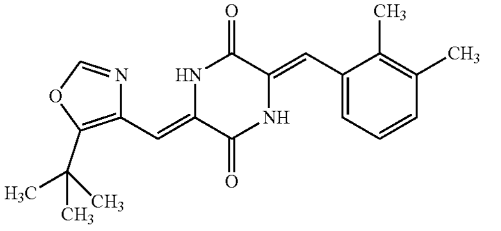 [SMILES: Cc1cccc(/C=c2\[nH]c(=O)/c(=C/c3ncoc3C(C)(C)C)[nH]c2=O)c1C] | KPU-225; tBu-Oxadelta-PLH-2,3-diMe |

TABLE B-continued
| Structure | Chemical name |
|---|---|
| 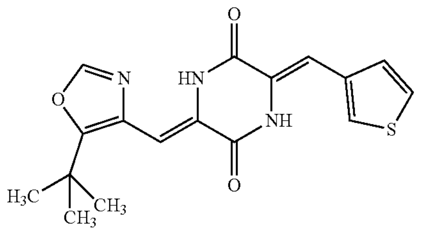 | KPU-226; tBu-Oxadelta-PLH-3-thienyl |
| 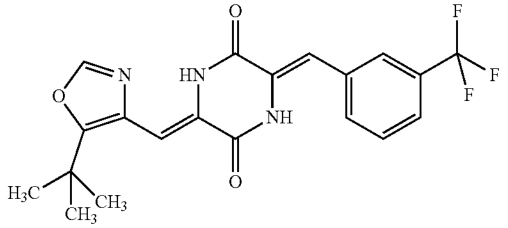 [SMILES: CC(C)(C)c1ocnc1/C=c1\[nH]c(=O)/c(=C/c2cccc(C(F)(F)F)c2)[nH]c1=O] | KPU-227; tBu-Oxadelta-PLH-m-CF3 |
| 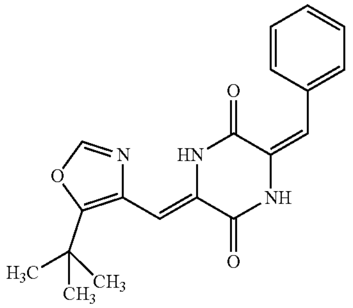 [SMILES: CC(C)(C)c1ocnc1/C=c1\[nH]c(=O)/c(=C\c2ccccc2)[nH]c1=O] | KPU-85; (E)-tBu-delta-PLH |
| 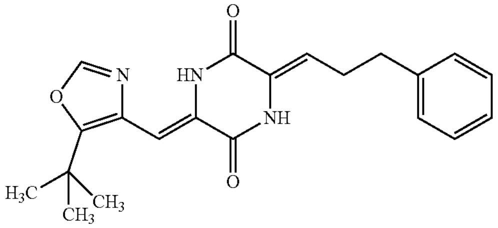 [SMILES: CC(C)(C)c1ocnc1/C=c1\[nH]c(=O)/c(=C/CCc2ccccc2)[nH]c1=O] | KPU-228; tBu-oxadelta-PLH-Ph-pr |
| 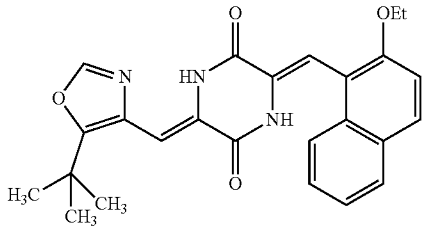 [SMILES: CCOc1ccc2ccccc2c1/C=c1\[nH]c(=O)/c(=C/c2ncoc2C(C)(C)C)[nH]c1=O] | KPU-229; tBu-oxadelta-PLH-2-OEt-1-naphth |
| 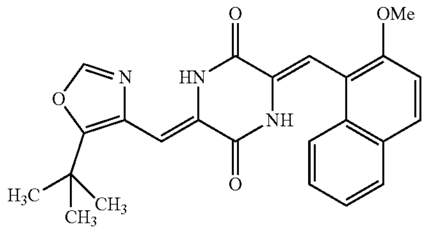 | KPU-230; tBu-oxadelta-PLH-2-OMe-1-naphth |
Additional dehydrophenylahistin derivatives TABLE B-continued
| Additional dehydrophenylahistin derivatives | |
|---|---|
| Structure | Chemical name |
| 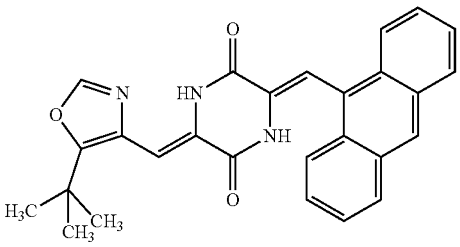 [SMILES: CC(C)(C)c1ocnc1/C=c1\[nH]c(=O)/c(=C/c2c3ccccc3cc3ccccc23)[nH]c1=O] | KPU-231; tBu-oxadelta-PLH-9-anth |
| 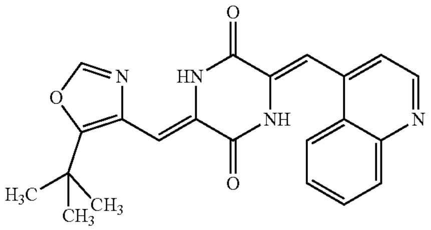 [SMILES: CC(C)(C)c1ocnc1/C=c1\[nH]c(=O)/c(=C/c2ccnc3ccccc23)[nH]c1=O] | KPU-232; tBu-oxadelta-PLH-4-quinoline |
| 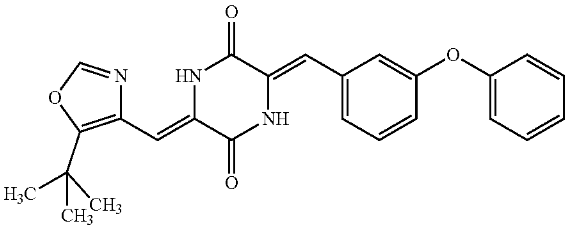 [SMILES: CC(C)(C)c1ocnc1/C=c1\[nH]c(=O)/c(=C/c2cccc(Oc3ccccc3)c2)[nH]c1=O] | KPU-233; tBu-oxadelta-PLH-3-phenoxy |
| 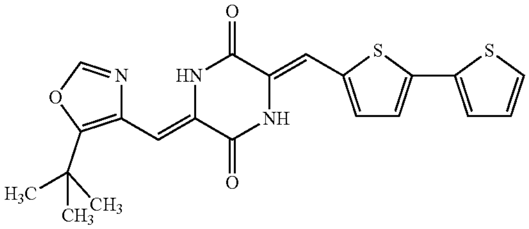 [SMILES: CC(C)(C)c1ocnc1/C=c1\[nH]c(=O)/c(=C/c2ccc(-c3cccs3)s2)[nH]c1=O] | KPU-234; tBu-oxadelta-PLH-2,2'-bitio |
| 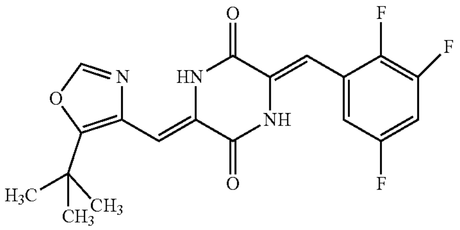 [SMILES: CC(C)(C)c1ocnc1/C=c1\[nH]c(=O)/c(=C/c2cc(F)cc(F)c2F)[nH]c1=O] | KPU-235; tBu-oxadelta-PLH-2,3,5-trifluoro |
| 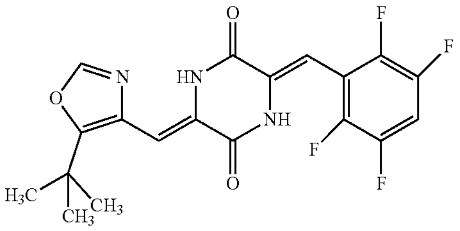 [SMILES: CC(C)(C)c1ocnc1/C=c1\[nH]c(=O)/c(=C/c2c(F)c(F)cc(F)c2F)[nH]c1=O] | KPU-236; tBu-oxadelta-PLH-2,3,5,6-tetrafluoro |

TABLE B-continued
| Additional dehydrophenylahistin derivatives | |
|---|---|
| Structure | Chemical name |
| 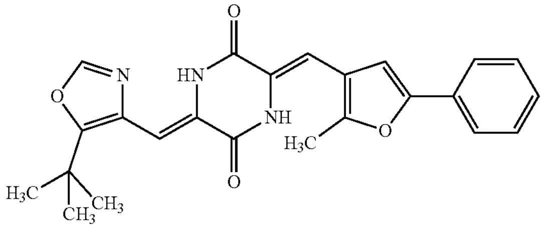 [SMILES: Cc1oc(-c2ccccc2)cc1/C=c1\[nH]c(=O)/c(=C/c2ncoc2C(C)(C)C)[nH]c1=O] | KPU-237; tBu-oxadelta-PLH-2-Me-5-Ph-3-furyl |
| 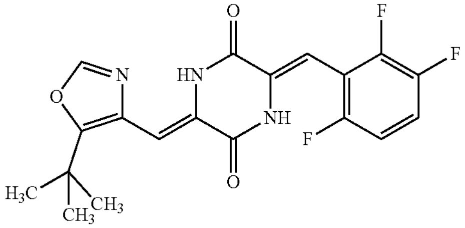 [SMILES: CC(C)(C)c1ocnc1/C=c1\[nH]c(=O)/c(=C/c2c(F)ccc(F)c2F)[nH]c1=O] | KPU-238; tBu-oxadelta-PLH-2,3,6-trifluoro |
| 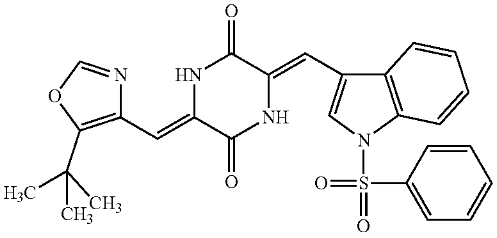 [SMILES: CC(C)(C)c1ocnc1/C=c1\[nH]c(=O)/c(=C/c2cn(S(=O)(=O)c3ccccc3)c3ccccc23)[nH]c1=O] | KPU-239; tBu-oxadelta-PLH-1-(Ph-sulfo)-3-indole |
| 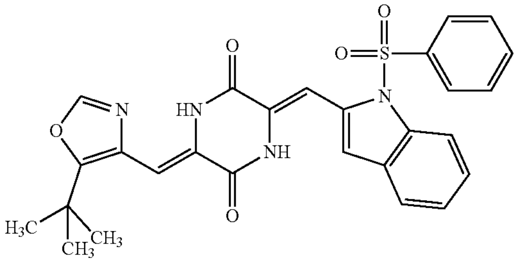 [SMILES: CC(C)(C)c1ocnc1/C=c1\[nH]c(=O)/c(=C/c2cc3ccccc3n2S(=O)(=O)c2ccccc2)[nH]c1=O] | KPU-240; tBu-oxadelta-PLH-1-(Ph-sulfo)-2-indole |
| 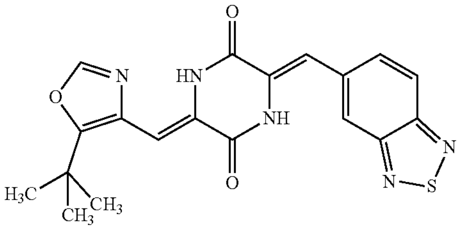 [SMILES: CC(C)(C)c1ocnc1/C=c1\[nH]c(=O)/c(=C/c2ccc3nsnc3c2)[nH]c1=O] | KPU-241; tBu-oxadelta-PLH-2,1,3-benzothiadiazole |
| 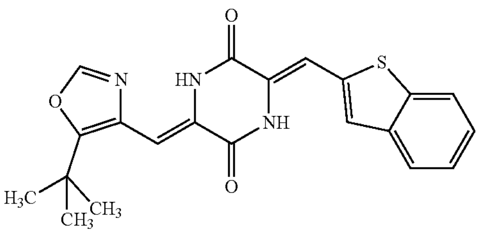 [SMILES: CC(C)(C)c1ocnc1/C=c1\[nH]c(=O)/c(=C/c2cc3ccccc3s2)[nH]c1=O] | KPU-242; tBu-oxadelta-PLH-2-benzothiophen |

TABLE B-continued

| Additional dehydrophenylahistin derivatives | |
|---|---|
| Structure | Chemical name |
| 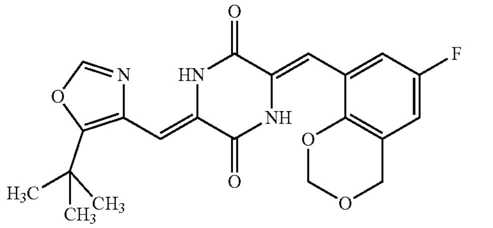 [SMILES: CC(C)(C)c1ocnc1/C=c1\[nH]c(=O)/c(=C/c2cc(F)cc3c2OCOC3)[nH]c1=O] | KPU-243; tBu-oxadelta-PLH-7-fluoro-2,4-benzodioxine |
| 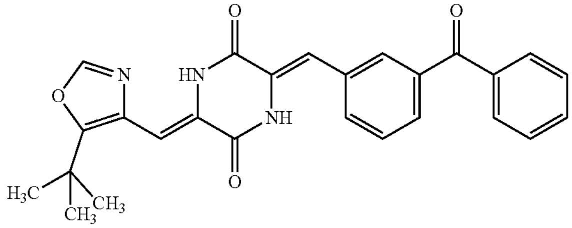 [SMILES: CC(C)(C)c1ocnc1/C=c1\[nH]c(=O)/c(=C/c2cccc(C(=O)c3ccccc3)c2)[nH]c1=O] | KPU-244; tBu-oxadelta-PLH-3-benzoyl |
| 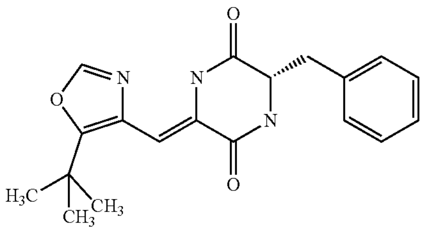 [SMILES: CC(C)(C)c1ocnc1/C=C1\NC(=O)[C@H](Cc2ccccc2)NC1=O] | KPU-245; tBu-oxa-PLH |

More examples of phenylahistin and dehydrophenylahistin derivatives can be found in US 20050090667, which is incorporated herein for reference for this purpose in its entirety.

Some embodiments relate to a compound having a structure of formula (IV)

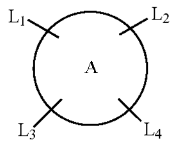

(IV)

or a pharmaceutically acceptable salt, prodrug, ester thereof, wherein A is selected from $C_{1-20}$ alkyl; $C_{2-6}$ alkenyl; $C_{2-6}$ alkynyl; $C_{1-6}$ heteroalkyl; $C_{3-7}$ carbocyclyl; 4-10 membered heterocyclyl; $C_{6-10}$ aryl; 3-10 membered heteroaryl; $C_1$-$C_6$ alkoxy($C_1$-$C_6$)alkyl; aryloxy; or sulfhydryl; each optionally substituted with one or more substituents.

Pharmaceutical Composition and Administration

Some embodiments relate to a pharmaceutical composition comprising the compound described herein.

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof, and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

In some embodiments, the composition can further include one or more pharmaceutically acceptable diluents. In some embodiments, the pharmaceutically acceptable diluent can include Kolliphor HS15® (Polyoxyl (15)-hydroxystearate). In some embodiments, the pharmaceutically acceptable diluent can include propylene glycol. In some embodiments, the pharmaceutically acceptable diluents can include kolliphor and propylene glycol. In some embodiments, the pharmaceutically acceptable diluents can include kolliphor and propylene glycol, wherein the kolliphor is about 40% by weight and propylene glycol is about 60% by weight based on the total weight of the diluents. In some embodiments, the composition can further include one or more other pharmaceutically acceptable excipients.

Standard pharmaceutical formulation techniques can be used to make the pharmaceutical compositions described herein, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of the compound described herein or pharmaceutically acceptable salts thereof, (b) a pharmaceutically acceptable carrier, diluent, excipient or combination thereof.

The actual dose of the active compounds described herein depends on the specific compound, and on the condition to be treated; the selection of the appropriate dose is well within the knowledge of the skilled artisan. In some embodiments, a daily dose of the compound described herein may be from about 0.01 mg/kg to about 250 mg/kg of body weight, from about 0.1 mg/kg to about 200 mg/kg of body weight, from about 0.25 mg/kg to about 120 mg/kg of body weight, from about 0.5 mg/kg to about 70 mg/kg of body weight, from about 1.0 mg/kg to about 50 mg/kg of body weight, from about 1.0 mg/kg to about 15 mg/kg of body weight, from about 2.0 mg/kg to about 15 mg/kg of body weight, from about 3.0 mg/kg to about 12 mg/kg of body weight, or from about 5.0 mg/kg to about 10 mg/kg of body weight. In some embodiments, a daily dose of the compound described herein may be about 15 mg/kg, 12 mg/kg, 10 mg/kg, 8 mg/kg, 5 mg/kg, 2.5 mg/kg, 1.5 mg/kg, 1.0 mg/kg, 0.8 mg/kg, 0.5 mg/kg, or 0.1 mg·kg of body weight. Thus, for administration to a 70 kg person, the dosage range may be from about 17 mg per day to about 8000 mg per day, from about 35 mg per day or less to about 7000 mg per day or more, from about 70 mg per day to about 6000 mg per day, from about 70 mg per day to about 1000 mg per day, from about 70 mg to about 800 mg per day, from about 350 mg to about 700 mg per day.

In some embodiments, a daily dose of the compound described herein may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range may be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day.

Method of Treatment

Some embodiments relate to a method of treating a proliferative disease, disorder, or condition comprising administering to a subject in need thereof the compound or the composition described herein.

Some embodiments relate to a method of treating a cancer comprising administering to a subject in need thereof the compound or the composition described herein.

Some embodiments relate to a use of a therapeutically effective amount of a compound or the composition described herein in the preparation of a medicament for treating or inhibiting progression of cancer.

Some embodiments relate to a therapeutically effective amount of a compound of a therapeutically effective amount of a compound or for use in the treatment of or inhibition of progression of cancer.

In some embodiments, the cancer is head and neck cancer, lung cancer, stomach cancer, colon cancer, pancreatic cancer, prostate cancer, breast cancer, kidney cancer, bladder cancer, ovary cancer, cervical cancer, melanoma, glioblastoma, myeloma, lymphoma, or leukemia. In some embodiments, the cancer is renal cell carcinoma, malignant melanoma, non-small cell lung cancer (NSCLC), ovarian cancer, Hodgkin's lymphoma or squamous cell carcinoma. In some embodiments, the cancer is selected from breast cancer, colon cancer, rectal cancer, lung cancer, prostate cancer, melanoma, leukemia, ovarian cancer, gastric cancer, renal cell carcinoma, liver cancer, pancreatic cancer, lymphomas and myeloma. In some embodiments, the cancer is a solid tumor or hematological cancer.

In some embodiments, the cancer is selected from breast cancer, colon cancer, rectal cancer, lung cancer, prostate cancer, melanoma, leukemia, ovarian cancer, gastric cancer, renal cell carcinoma, liver cancer, pancreatic cancer, lymphomas and myeloma. In some embodiments, the cancer is a solid tumor or hematological cancer. In some embodiments, the cancer is the cancer is selected from colon cancer, breast cancer, lung cancer, pancreas cancer, prostate cancer, colorectal adenocarcinoma, a non-small cell lung cancer, a melanoma, a pancreatic cancer, leukemia, ovarian cancer, gastric cancer, renal cell carcinoma, liver cancer, pancreatic cancer, lymphomas and myeloma.

In some embodiments, the subject is a mammal. In some embodiments, the subject is a human.

EXAMPLES

Example 1

Figure 2:
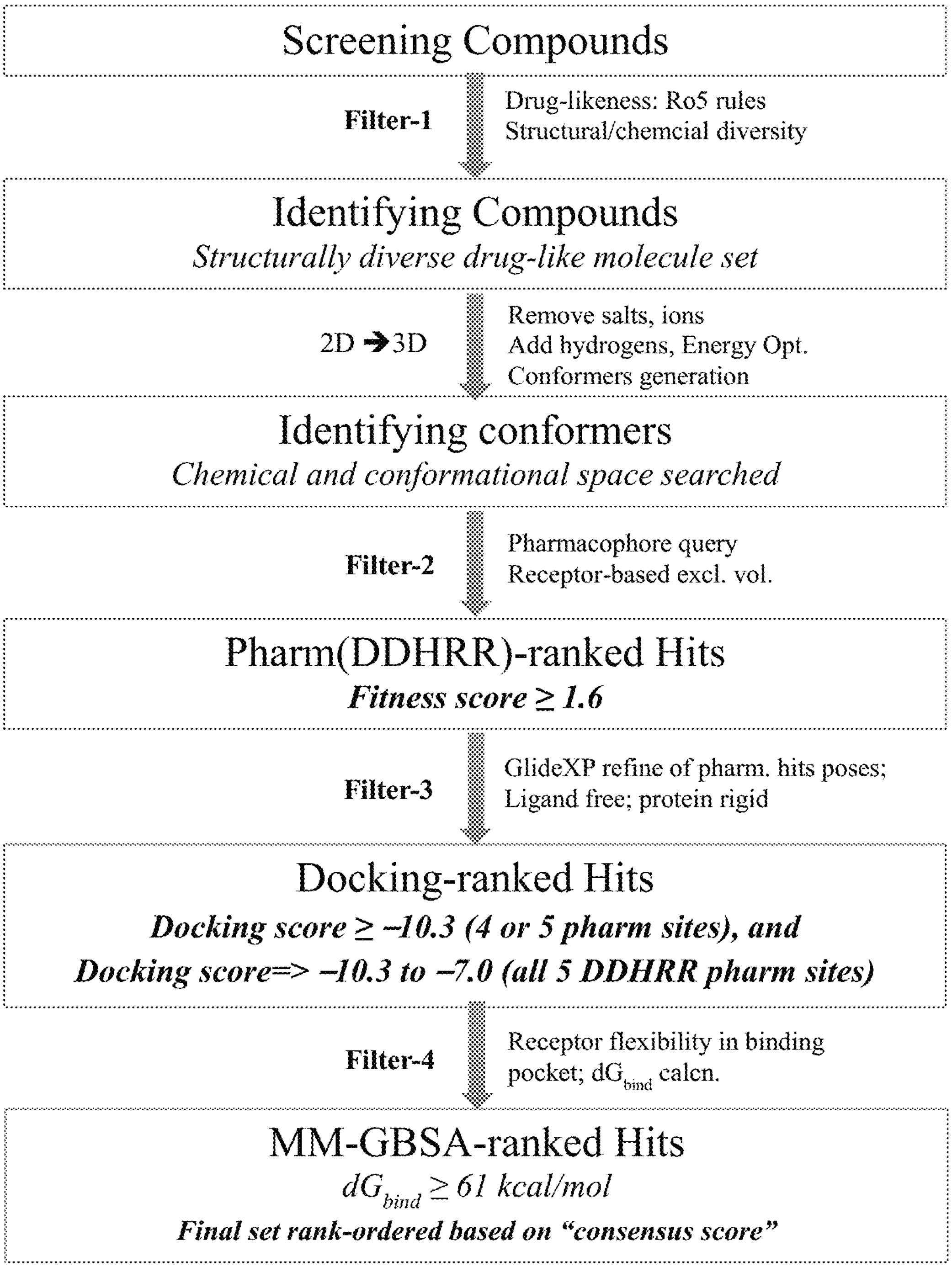
FIG. 2 is a flowchart showing the steps for screening compounds that can bind to tubulin based on the pharmacophore model.

Screening Protocols: Molecular modeling and screening operations were performed in the Maestro modeling suite (v11.4; Schrödinger), running on iMac workstations running macOS v10.13. A set of over 35 million purchasable compounds from MCULE (https://mcule.com), was curated based on drug-likeness (rule of five parameters) and structural diversity criteria. After curation, approximately 1 million compounds remained (Mcule_Purchasable_In_Stock_Ro5_Diverse_1M_8Dec-2016 v1), of which half were used for first virtual screening campaign. The 2D SMILES of the compounds were converted into 3D structures after adding hydrogens, and energy optimized using LigPrep program. This process generated approximately 15 million conformers. The steps for screening the compounds based on this pharmacophore is shown in FIG. 2.

A pharmacophore query was generated to capture sites or features (binding interactions) present in a set of known active molecules (Plinabulin and its more potent analogs), for use in virtual screening to bias the screening towards these 'active interaction' extracted from known active molecules.

FIG. 1 shows the structure of the pharmacophore used for screening. In FIG. 1, the residues around Residues around R11 (Phenyl ring in Plinabulin) includes: 3 Å residues: N167, T239, L242, L252; and 4 Å residues: 14, Y52, Q136, F169, E200, Y202, V238; Residues around Right R10 (Imidazole ring in Plinabulin): 3 Å residues: L255, M259, A316; and 4 Å residues: T179 (A chain), N258, 1318, K352; Residues around H8 (t-butyl on Imidazole ring of Plinabulin): 3 Å residues: T179 (A chain), T353; and 4 Å residues: S241, L248, L255, K352, A354, A316, A317, 1318; Residues around D4/D6H-bond donor sites (Central piperazinedione ring in Plinabulin): 3 Å residues: S241, V238 (backbone), 1318, L255, E200, Y202; and 4 Å residues: L242, M259, F268, A316, 1378. The bold residues indicate possible hydrophobic (including pi-) and H-bond interactions with particular pharmacophore site.

Plinabulin analogs were sketched within Plinabulin/Colchicine binding site of tubulin from 1.5 Å resolution crystal structure (see Example 2) and energy optimized to relieve additional functional groups on core Plinabulin structure within binding pocket. Visual inspection of the tubulin-plinabulin complex structure indicated that plinabulin may bind stronger to beta3-tubulin where betaCys241 is substituted by a serine residue; the side chain of a serine at position 241 may allow for the formation of a stronger hydrogen bond with the O20 atom of plinabulin compared to the one of cysteine. Additionally, excluded volume based on actual receptor's binding site residues was used to help restrict the hits' exploration space to actual ligand binding site boundary, which can be useful during next step of structure-based screening workflow. The conformers of every molecule were generated on-the-fly during the pharmacophore screen using the DDHRR pharmacophore query, which represented 2 terminal aromatic rings (RR), 2 hydrogen-bond donors (DD), and a hydrophobic site (H). A 'fitness score' from pharmacophore screen was used as a ranking parameter, which consists of an alignment score, vector score and volume score. Only hits that matched at least 4 out of 5 sites (hits matching more sites are better), and a fitness score equal to, or greater than 1.6 were considered for structure-based docking screen. The pharmacophore screening led to approximately 9,000 hits that passed the above criteria and were evaluated in the tubulin binding pocket.

Structure-based virtual screening (SBVS) was conducted on the approximately 9,000 hits. Docking screened was performed using 'refine only' as ligand sampling method in Glide's extra-precision (XP) scoring in which a quick optimization of each ligand from its input coordinates is performed. This was used to relieve any steric clashes of 'pharmacophore-aligned ligand-pose' with binding site residues, and form additional hydrogen bonding and hydrophobic interactions with nearby residues. In this step the ligand was free to move, while the protein was treated as rigid, except for hydroxyl groups in Serine residues which were flexible. The energy optimized ligand-receptor complexes were then scored using the more accurate Glide XP scoring function, which was reported to filter out false positive hits and enrich the success of screening campaign (Glide score is an estimate of the binding affinity, but it is only accurate to a few kcal/mol). Out of 9,000 pharmacophore hits evaluated in this step, there were 1,212 hits with a docking score higher than −10.3, which matched either 4 or 5 pharmacophore sites, or had lower docking score between −10.3 and −7.0, but matched all 5 pharmacophore sites.

Binding energy prediction for rank-ordering of potential hits: Prime MM-GBSA involves molecular mechanics optimization of ligand-protein complexes, in which the ligand and 5 Å binding site residues are flexible during energy optimization. The MM-GBSA dGbind score is expected to agree reasonably well with ranking based on experimental binding affinity, and has been developed for rank-ordering congeneric series of ligands (MM-GBSA binding energies are approximate free energies of binding, a more negative value indicates stronger binding). Plinabulin and two of its nanomolar analogs were included in this evaluation as positive controls, and all hits with dGbind better than Plinabulin's dGbind score were selected for further analysis. Out of 1,212 hits evaluated in this computationally highly expensive step, 353 hits ranked better than Plinabulin, and their binding poses were visually inspected. Further analysis of 353 hits revealed that only 51 hits as shown in Table 1 matched all the five (DDHRR) pharmacophore sites, 293 hits as shown Table 2 matched only four (DHRR) sites (one of the H-bond donors missing), and 9 hits as shown in Table 3 matched (DDRR) sites (hydrophobic site missing).

Finally, a consensus score (CSCORE) based on fitness score, GlideXP docking score, and MM-GBSA dGbind score was developed, with 0.5, 0.5, and 1.0 weightage respectively, so that more accurate dGbind scoring got full weightage, while uniquely important but less accurate pharmacophore and docking scores received half weightage:

$$CSCORE=(0.5*DockingScore)-(0.5*FitnessScore)+(1.0*dGbindScore).$$

Note: Negative sign to FitnessScore was applied to maintain the overall analysis that lower (i.e., more −ve) the score value better will be its ranking, because FitnessScore is the only +ve score (better +ve valuer, higher the ranking) among the scores.

Example 2

The 1.5 Å resolution crystal structure of the tubulin-plinabulin complex was solved. Proteins and crystals of the TD1 complex (a protein complex containing one αβ-tubulin dimer and the tubulin-binding Darpin D1), as described in Pecqueur, L., et al., *Proc. Natl. Acad. Sci.* (2012) 109, 12011-12016 (coordinates deposited in the Protein Data Bank (PDB ID 4DRX)), both of which are incorporated herein for reference in their entireties, were prepared (the amino acid residue numbering used herein for β-tubulin differs by two relative to that in PDB ID 4DRX). Briefly, co-crystallization experiments were performed by diluting a freshly prepared 50 mM plinabulin stock solution (in 100% DMSO) to 5 mM with the crystallization solution (100 mM Bis-TrisMethane pH 5.5, 200 mM Ammonium Sulfate, 25% PEG3350). 1 μL of TD1 at 15 mg/mL was mixed to 1 μL of the 5 mM plinabulin solution and equilibrated against 400 μL of the crystallization solution (hanging drop method).

Crystals appeared overnight and were flash frozen in liquid nitrogen and used directly for Xray diffraction experiments at 100K at the X06DA beamline of the Swiss Light Source (Paul Scherrer Institut, Villigen, Switzerland). Data processing was performed using the XDS software package. The TD1-plinabulin complex crystallized in space group P1211 with a single complex in the asymmetric unit. Structure solution was performed by molecular replacement method using the tubulin-darpin complex structure (PDB ID 4DRX) in the absence of any ligands and solvent as a model using the PHASER program in the PHENIX software package. Plinabulin was added to the model using eLBOW in PHENIX. The resulting model was improved through iterative rounds of model rebuilding in Coot and refinement in PHENIX. The quality of the structure was assessed with MolProbity. Data collection and refinement statistics are presented in Table 4. Figures were prepared using PyMOL (The PyMOL Molecular Graphics System, Version 1.4.1. Schrödinger).

TABLE 4

X-ray data collection and refinement statistics

| Data Collection[a] | |
|---|---|
| Wavelength, Å | 1 |
| Space group | P 1 21 1 |
| Resolution range, Å | 45.02-1.519 (1.574-1.519) |
| Unit cell a, b, c, (Å) | 73.565 91.351 83.221 |
| α, β, γ (°) | 90 96.851 90 |
| No. of observed reflections | 1127765 (103861) |
| No. of unique reflections | 166365 (15828) |
| Mean I/sigma(I) | 16.43 (1.21) |
| R-merge | 0.05515 (1.52) |
| R-meas | 0.05971 (1.648) |
| CC1/2[b] | 0.999 (0.683) |
| CC* | 1 (0.901) |
| Refinement | |
| R-work | 0.1937 (0.3736) |
| R-free | 0.2080 (0.3647) |
| Macromolecules | 7937 |

TABLE 4-continued

| X-ray data collection and refinement statistics | |
|---|---|
| Ligands | 86 |
| Protein residues | 1014 |
| RMS (bonds) (Å) | 0.016 |
| RMS (angles) (°) | 1.71 |
| Ramachandran favored (%)[c] | 98.30 |
| Ramachandran outliers (%)[c] | 0 |
| B-factors | |
| Average B-factor | 35.80 |
| Macromolecules | 34.67 |
| Ligands | 28.13 |
| Solvent | 45.77 |

[a]Highest resolution shell statistics are in parentheses.
[b]As defined by Karplus and Diederichs (Karplus and Diedrichs, 2012).
[c]As defined by MolProbity (Chen et al., 2010).

Figure 3:
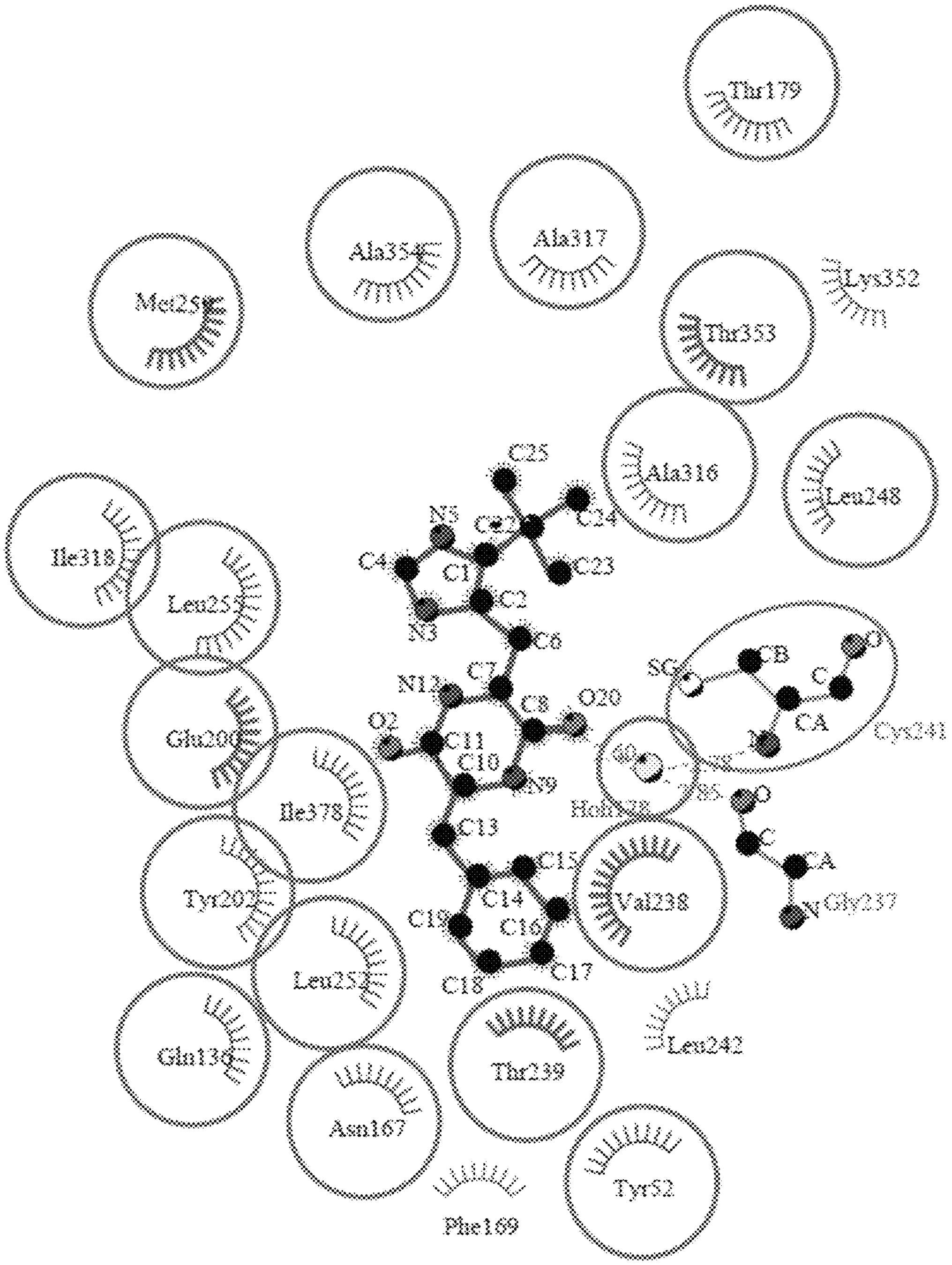
FIG. 3 shows the interacting residues seen in the tubulin-plinabulin complex.

The TD1-plinabulin complex structure was determined at 1.5 Å resolution. Unambiguous difference electron density for plinabulin was observed on the β-tubulin subunits in the TD1-plinabulin complex allowing the modeling of the plinabulin. Plinabulin binds at the colchicine site on tubulin, which is located at the interface between the α- and β-tubulin subunits. It was formed by strands βS1, βS4, βS6, βS7, βS8, βS9, and βS10, loop βT7, and helices βH7 and βH8 of β-tubulin, as well as the loop αT5 of α-tubulin. The overall structure of tubulin in the TD1-plinabulin complex could be readily superimposed with the one obtained in the absence of any ligand (PDB ID 4DRX, rmsd of 0.28 Å over 684 Cα atoms). This result suggested that binding of plinabulin did not affect the global conformation of the tubulin dimer. The interacting residues seen in the tubulin-plinabulin complex is shown in FIG. 3.

Plinabulin binding was established by hydrogen bond interactions with βE200 and βV238 and with βG237, βC241 and αT179 mediated via water molecules. Interestingly, the side chain of βC241 was present in two alternate conformations, one of which makes a hydrogen bond with plinabulin. The additional β-tubulin residues lining the plinabulin binding site (residues within 4 Å of plinabulin) are: 14, βY52, βQ136, βY202, βF169, βN167, βL252, βL255, βM259, βF268, 1376, βL242, βT239, βA316, βA317, 1318, βA354, βL248, βT353, 1378 and βK352.

A comparison of the β-tubulin subunit between apo TD1 and TD1-plinabulin shows that the βT7 loop residues βL248 and βN249 occupy the plinabulin-binding site in the apo structure. Therefore, to accommodate plinabulin in its binding site the βT7 loop has to flip outwards. Similar conformational changes have been observed upon binding of other colchicine site ligands to tubulin. However, in contrast to the colchicine bound tubulin, αT5 loop of α-tubulin in the TD1-plinabulin complex structure maintains its conformation similar to apo tubulin. Since plinabulin belongs to the class of colchicine site binders that are structurally unrelated to colchicine, the beta tubulin from T2R-TTL-colchicine structure (PDB ID 402B) was superimposed onto the TD1-plinabulin structure. The overall conformation of beta tubulin remained unchanged between the two structures (rmsd of 0.37 over 370 Cα atoms). Despite sharing the same binding pocket, plinabulin binds at a site with little overlap with colchicine but with a partial overlap with nocodazole. We compared the binding mode of plinabulin with tubulin to the crystal structures of other known colchicine site binding ligands using LigPlot. Almost all the tubulin residues lining the tubulin dimer in the TD1-plinabulin structure assumes the "curved" conformation characteristic of free tubulin, in contrast with the "straight" tubulin structure that is found in microtubules. To assess whether the binding of plinabulin is compatible with the straight tubulin conformation present in microtubules, we compared the structures of tubulin in the curved and straight conformational states.

In straight tubulin, the plinabulin binding site was occluded by the βT7 loop of β-tubulin, resulting in severe clashes between the βT7 loop residues with the plinabulin molecule in the straight tubulin structure. Therefore, the plinabulin-binding site was not accessible in the straight tubulin subunits incorporated into the microtubule lattice. Plinabulin thus acts as microtubule destabilizer by binding to curved tubulin in solution and/or microtubule ends and preventing the "curved to-straight" structural transition required for microtubule formation. Table 5 lists the binding distance within 4 Å of plinabulin in tubulin structure.

TABLE 5

Distances within 4 Å of plinabulin in TD1 structure

| Plinabulin atom | Tubulin chain (A or B) or solvate (S) | Binding Residue | Residue position | Binding residue side chain atom | Distance/Å |
|---|---|---|---|---|---|
| C1 | B | LEU | 255 | CD2: | 3.778 |
| C1 | B | ALA | 316 | CB: | 3.808 |
| C2 | B | LEU | 255 | CD2: | 3.627 |
| C2 | B | ALA | 316 | CB: | 3.393 |
| N3 | B | LEU | 255 | CD2: | 3.696 |
| N3 | B | MET | 259 | CG: | 3.604 |
| N3 | B | ALA | 316 | CB: | 3.494 |
| C4 | S | HOH | 243 | O: | 3.198 |
| C4 | S | HOH | 511 | O: | 3.569 |
| C4 | B | LEU | 255 | CD2: | 3.873 |
| C4 | B | MET | 259 | CG: | 3.688 |
| C4 | B | MET | 259 | SD: | 4 |
| C4 | B | ALA | 316 | CB: | 3.97 |
| N5 | S | HOH | 243 | O: | 2.85 |
| N5 | B | LEU | 255 | CD2: | 3.919 |
| C6 | B | ALA | 316 | CB: | 3.68 |
| C6 | B | ILE | 318 | CD1: | 3.764 |
| C7 | B | ILE | 378 | CD1: | 3.746 |
| C8 | S | HOH | 178 | O: | 3.658 |
| C8 | B | VAL | 238 | O: | 3.281 |
| C8 | B | CYS | 241 | SG: | 3.59 |
| C8 | B | ILE | 378 | CDL | 3.583 |
| N9 | B | TYR | 202 | OH: | 3.853 |
| N9 | B | VAL | 238 | C: | 3.655 |
| N9 | B | VAL | 238 | O: | 2.59 |
| N9 | B | VAL | 238 | CG2: | 3.389 |
| N9 | B | VAL | 238 | CG1: | 3.755 |
| N9 | B | ILE | 378 | CD1: | 3.908 |
| C10 | B | TYR | 202 | OH: | 3.206 |
| C10 | B | VAL | 238 | O: | 3.726 |
| C10 | B | VAL | 238 | CG2: | 3.842 |
| C11 | B | TYR | 202 | OH: | 3.59 |
| C11 | B | LEU | 255 | CB: | 3.657 |
| C11 | B | LEU | 255 | CD1: | 3.751 |
| N12 | B | LEU | 255 | CB: | 3.556 |
| N12 | B | LEU | 255 | CG: | 3.958 |
| N12 | B | LEU | 255 | CD1: | 3.759 |
| C13 | B | GLU | 200 | OE1: | 3.342 |
| C13 | B | TYR | 202 | OH: | 3.03 |
| C13 | B | VAL | 238 | CG2: | 3.859 |
| C14 | B | TYR | 202 | OH: | 3.897 |
| C14 | B | VAL | 238 | O: | 3.832 |
| C14 | B | VAL | 238 | CG2: | 3.722 |
| C14 | B | VAL | 238 | CG1: | 3.742 |
| C14 | B | LEU | 252 | CD2: | 3.819 |
| C15 | B | VAL | 238 | O: | 3.209 |
| C15 | B | LEU | 242 | CD2: | 3.581 |
| C15 | B | LEU | 252 | CD2: | 3.56 |
| C16 | B | TYR | 52 | OH: | 3.749 |
| C16 | B | VAL | 238 | O: | 3.727 |
| C16 | B | THR | 239 | CA: | 3.796 |
| C16 | B | THR | 239 | CB: | 3.992 |
| C16 | B | THR | 239 | CG2: | 3.43 |

TABLE 5-continued

Distances within 4 Å of plinabulin in TD1 structure

| Plinabulin atom | Tubulin chain (A or B) or solvate (S) | Binding Residue | Residue position | Binding residue side chain atom | Distance/ Å |
|---|---|---|---|---|---|
| C16 | B | LEU | 242 | CD2: | 3.8 |
| C16 | B | LEU | 252 | CD2: | 3.735 |
| C17 | B | TYR | 52 | OH: | 3.461 |
| C17 | B | GLN | 136 | OE1: | 3.272 |
| C17 | B | THR | 239 | CG2: | 3.4 |
| C18 | B | GLN | 136 | OE1: | 3.802 |
| C18 | B | PHE | 169 | CE1: | 3.892 |
| C18 | B | PHE | 169 | CZ: | 3.778 |
| C19 | B | ASN | 167 | ND2: | 3.427 |
| C19 | B | TYR | 202 | CE1: | 3.811 |
| C19 | B | VAL | 238 | CG1: | 3.93 |
| O20 | S | HOH | 178 | O: | 2.599 |
| O20 | B | VAL | 238 | C: | 3.871 |
| O20 | B | VAL | 238 | O: | 3.084 |
| O20 | B | CYS | 241 | SG: | 3.295 |
| O20 | B | ILE | 318 | CG1: | 3.786 |
| O20 | B | ILE | 318 | CD1: | 3.621 |
| O20 | B | ILE | 378 | CD1: | 3.84 |
| O21 | B | GLU | 200 | CD: | 3.53 |
| O21 | B | GLU | 200 | OE1: | 3.327 |
| O21 | B | GLU | 200 | OE2: | 2.957 |
| O21 | B | TYR | 202 | OH: | 3.765 |
| O21 | B | LEU | 255 | CB: | 3.325 |
| C23 | A | THR | 179 | CB: | 3.859 |
| C23 | A | THR | 179 | CG2: | 3.626 |
| C24 | B | ALA | 316 | CB: | 3.983 |
| C24 | B | ALA | 317 | O: | 3.69 |
| C24 | B | ILE | 318 | CD1: | 3.395 |
| C24 | B | LYS | 352 | O: | 3.824 |
| C24 | B | THR | 353 | CA: | 3.963 |
| C24 | B | THR | 353 | C: | 3.866 |
| C24 | B | ALA | 354 | N: | 3.805 |
| C24 | B | ALA | 354 | CB: | 3.867 |
| C25 | B | CYS | 241 | SG: | 3.567 |
| C25 | B | LEU | 248 | CD2: | 3.71 |
| C25 | B | ILE | 318 | CD1: | 3.941 |
| C25 | B | ALA | 354 | CB: | 3.831 |
| H1 | B | ALA | 316 | CB: | 3.517 |
| H1 | B | ILE | 318 | CG1: | 3.814 |
| H1 | B | ILE | 318 | CD1: | 2.898 |
| H2 | S | HOH | 243 | O: | 2.912 |
| H2 | S | HOH | 511 | O: | 2.896 |
| H2 | B | LEU | 255 | O: | 3.638 |
| H2 | B | ASN | 258 | CB: | 3.78 |
| H2 | B | MET | 259 | CG: | 3.233 |
| H2 | B | MET | 259 | SD: | 3.677 |
| H3 | S | HOH | 243 | O: | 3.531 |
| H3 | A | THR | 179 | CB: | 3.688 |
| H3 | A | THR | 179 | CG2: | 3.532 |
| H3 | B | LYS | 352 | C: | 3.902 |
| H3 | B | LYS | 352 | CB: | 3.197 |
| H4 | S | HOH | 243 | O: | 3.763 |
| H4 | A | THR | 179 | CB: | 3.407 |
| H4 | A | THR | 179 | CG2: | 3.462 |
| H4 | A | THR | 179 | OG1: | 3.885 |
| H5 | A | THR | 179 | CB: | 3.888 |
| H5 | A | THR | 179 | CG2: | 3.294 |
| H5 | B | THR | 353 | C: | 3.763 |
| H5 | B | THR | 353 | O: | 3.501 |
| H5 | B | ALA | 354 | CB: | 3.702 |
| H6 | B | ALA | 316 | CB: | 3.873 |
| H6 | B | ALA | 317 | N: | 3.776 |
| H6 | B | ALA | 317 | O: | 3.638 |
| H6 | B | LYS | 352 | C: | 3.187 |
| H6 | B | LYS | 352 | O: | 2.928 |
| H6 | B | LYS | 352 | CB: | 3.983 |
| H6 | B | THR | 353 | N: | 3.381 |
| H6 | B | THR | 353 | CA: | 3.302 |
| H6 | B | THR | 353 | C: | 3.466 |
| H6 | B | THR | 353 | O: | 3.995 |
| H6 | B | ALA | 354 | N: | 3.704 |
| H7 | B | ALA | 317 | O: | 3.275 |
| H7 | B | ILE | 318 | CD1: | 3.021 |

TABLE 5-continued

Distances within 4 Å of plinabulin in TD1 structure

| Plinabulin atom | Tubulin chain (A or B) or solvate (S) | Binding Residue | Residue position | Binding residue side chain atom | Distance/ Å |
|---|---|---|---|---|---|
| H7 | B | THR | 353 | CA: | 3.721 |
| H7 | B | THR | 353 | C: | 3.348 |
| H7 | B | THR | 353 | O: | 3.952 |
| H7 | B | ALA | 354 | N: | 3.037 |
| H7 | B | ALA | 354 | CA: | 3.571 |
| H7 | B | ALA | 354 | CB: | 2.95 |
| H8 | B | ALA | 316 | CA: | 3.846 |
| H8 | B | ALA | 316 | C: | 3.965 |
| H8 | B | ALA | 316 | CB: | 3.278 |
| H8 | B | ALA | 317 | N: | 3.601 |
| H8 | B | ALA | 317 | C: | 3.986 |
| H8 | B | ALA | 317 | O: | 3.572 |
| H8 | B | ILE | 318 | CD1: | 2.898 |
| H8 | B | LYS | 352 | O: | 3.987 |
| H9 | B | CYS | 241 | SG: | 3.103 |
| H9 | B | LEU | 248 | CD2: | 3.576 |
| H9 | B | ILE | 318 | CD1: | 3.583 |
| H9 | B | ALA | 354 | CB: | 2.902 |
| H10 | B | CYS | 241 | SG: | 3.926 |
| H10 | B | LEU | 248 | CG: | 3.928 |
| H10 | B | LEU | 248 | CD1: | 3.569 |
| H10 | B | LEU | 248 | CD2: | 3.09 |
| H10 | B | LEU | 255 | CD2: | 3.588 |
| H11 | B | CYS | 241 | CB: | 3.85 |
| H11 | B | CYS | 241 | CB: | 3.883 |
| H11 | B | CYS | 241 | SG: | 3.198 |
| H11 | B | CYS | 241 | SG: | 3.482 |
| H11 | B | LEU | 248 | CD2: | 3.949 |
| H11 | B | LEU | 255 | CD2: | 3.751 |
| H11 | B | ILE | 318 | CD1: | 3.584 |
| H12 | S | HOH | 243 | O: | 2.18 |
| H12 | S | HOH | 511 | O: | 3.824 |
| H12 | B | LYS | 352 | CB: | 3.865 |
| H13 | S | HOH | 178 | O: | 3.917 |
| H13 | B | VAL | 238 | CA: | 3.725 |
| H13 | B | VAL | 238 | CA: | 3.746 |
| H13 | B | VAL | 238 | C: | 2.879 |
| H13 | B | VAL | 238 | O: | 1.798 |
| H13 | B | VAL | 238 | CB: | 3.905 |
| H13 | B | VAL | 238 | CG2: | 2.898 |
| H13 | B | VAL | 238 | CG1: | 3.195 |
| H13 | B | THR | 239 | N: | 3.968 |
| H14 | B | LEU | 255 | CB: | 3.211 |
| H14 | B | LEU | 255 | CG: | 3.827 |
| H14 | B | LEU | 255 | CD1: | 3.945 |
| H14 | B | LEU | 255 | CD2: | 3.918 |
| H14 | B | MET | 259 | CG: | 3.832 |
| H15 | B | ASN | 167 | ND2: | 3.661 |
| H15 | B | GLU | 200 | CD: | 3.356 |
| H15 | B | GLU | 200 | OE1: | 2.424 |
| H15 | B | GLU | 200 | OE2: | 3.598 |
| H15 | B | TYR | 202 | CE1: | 3.886 |
| H15 | B | TYR | 202 | CZ: | 3.789 |
| H15 | B | TYR | 202 | OH: | 2.842 |
| H17 | B | VAL | 238 | C: | 3.969 |
| H17 | B | VAL | 238 | O: | 2.862 |
| H17 | B | LEU | 242 | CG: | 3.863 |
| H17 | B | LEU | 242 | CD2: | 2.892 |
| H17 | B | LEU | 252 | CD2: | 3.756 |
| H18 | B | TYR | 52 | OH: | 3.272 |
| H18 | B | VAL | 238 | O: | 3.778 |
| H18 | B | THR | 239 | CA: | 3.342 |
| H18 | B | THR | 239 | CB: | 3.485 |
| H18 | B | THR | 239 | CG2: | 3.213 |
| H18 | B | LEU | 242 | CG: | 3.48 |
| H18 | B | LEU | 242 | CD2: | 3.315 |
| H19 | B | TYR | 52 | OH: | 2.683 |
| H19 | B | GLN | 136 | CD: | 3.618 |
| H19 | B | GLN | 136 | OE1: | 2.405 |
| H19 | B | THR | 239 | CG2: | 3.155 |
| H20 | B | GLN | 136 | CB: | 3.914 |
| H20 | B | GLN | 136 | OE1: | 3.477 |
| H20 | B | ASN | 167 | CB: | 3.828 |

TABLE 5-continued

Distances within 4 Å of plinabulin in TD1 structure

| Plinabulin atom | Tubulin chain (A or B) or solvate (S) | Binding Residue | Residue position | Binding residue side chain atom | Distance/ Å |
|---|---|---|---|---|---|
| H20 | B | PHE | 169 | CE1: | 3.257 |
| H20 | B | PHE | 169 | CZ: | 3.413 |
| H21 | B | ASN | 167 | CB: | 3.74 |
| H21 | B | ASN | 167 | CG: | 3.735 |
| H21 | B | ASN | 167 | ND2: | 3.051 |
| H21 | B | GLU | 200 | OE1: | 3.362 |
| H21 | B | TYR | 202 | CE1: | 3.074 |
| H21 | B | TYR | 202 | CZ: | 3.727 |
| H21 | B | TYR | 202 | OH: | 3.625 |

Example 3

A microtubule pelleting assay is used to test in vitro the direct effect of the tubulin binding compounds described herein such as the compounds listed in Tables 1, 2, and 3. The effect of the test compounds in Tables 1, 2, and 3 are compared with several microtubulin depolymerizing agents (MDA) (plinabulin, colchicine and ansamitocin) and one MSA (taxol). Freshly polymerised/depolymerised bovine brain tubulin is supplemented with 3400 Glycerol and 1 mM GTP and adjusted to a concentration of 4 mg/mL. Polymerization into microtubule is achieved by incubating the tubulin at 37° C. for 30 min.

To assess the effect of the compounds tested, a final concentration of 100 μM is added to the warm microtubules diluted at 2 mg/mL and after a 30 min incubation at 37° C., the reaction mixture is added on top of a glycerol cushion. After high speed centrifugation at 80,000 rpm for 15 min, the microtubule pellet fractions are separated from the supernatant fractions and analyzed by SDS-PAGE. In the presence of the 3 MDAs, the tubulin band is observed in the pellet fractions, which indicates the depolymerizing effect of these compounds. In contrast, taxol, which has a strong stabilizing effect on microtubules, increases the amount of tubulin observed in the pellet fraction. The test compounds generally show destabilizing effect on microtubules.

What is claimed is:

1. A method of treating or inhibiting the progression of cancer selected from the group consisting of breast cancer, colon cancer, rectal cancer, lung cancer, prostate cancer, melanoma, leukemia, ovarian cancer, gastric cancer, renal cell carcinoma, liver cancer, pancreatic cancer, lymphomas and myeloma, the method comprising:

administering to a subject in need thereof a compound selected from the group consisting of:

B-2

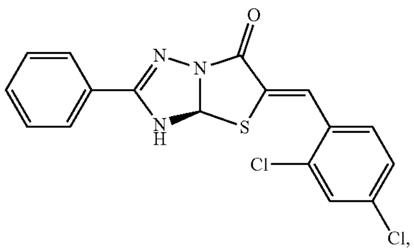

-continued

B-3

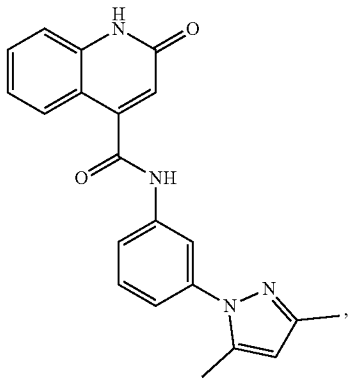

B-5

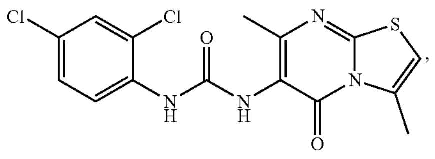

B-6

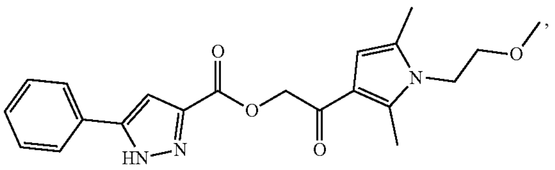

B-7

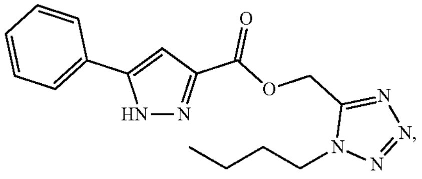

B-8

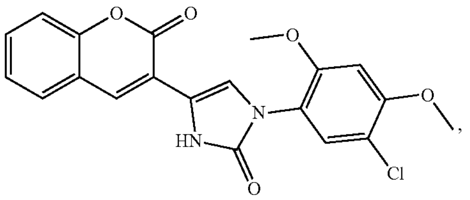

B-9

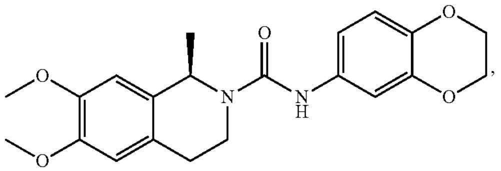

and

B-10

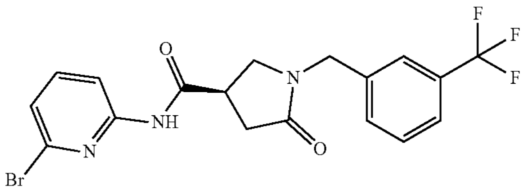

or a pharmaceutically acceptable salt thereof.

2. A pharmaceutical composition comprising a pharmaceutically acceptable excipient, and a compound selected from the group consisting of:
B-2
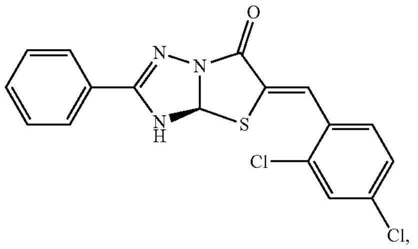
B-3
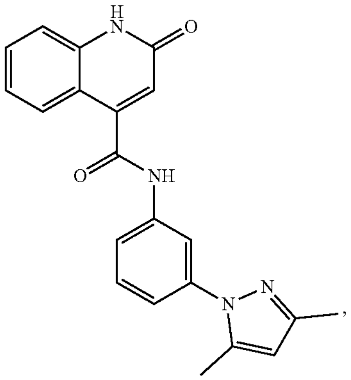
B-5
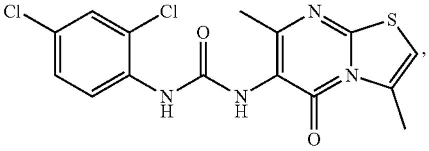
B-6
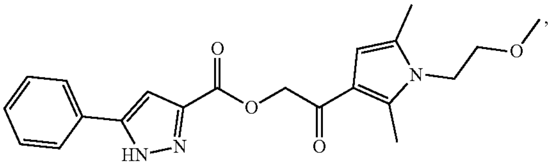
-continued
B-7
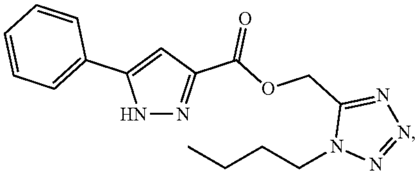
B-8
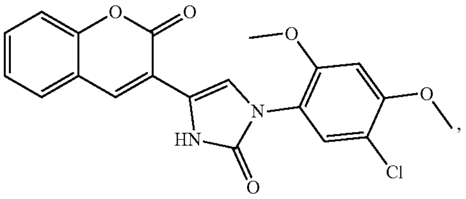
B-9
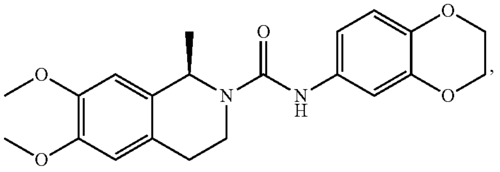
and
B-10
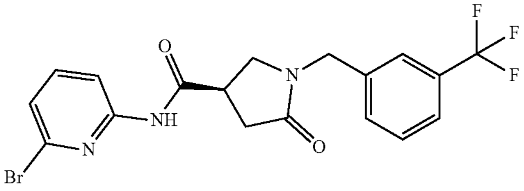
or a pharmaceutically acceptable salt thereof.
* * * * *